(12) United States Patent
Bao

(10) Patent No.: US 11,713,341 B1
(45) Date of Patent: Aug. 1, 2023

(54) ANTIMICROBIAL NCR13 VARIANT PEPTIDES

(71) Applicant: Vestaron Corporation, Kalamazoo, MI (US)

(72) Inventor: Lin Bao, Portage, MI (US)

(73) Assignee: Vestaron Corporation, Durham, NC (US)

( * ) Notice: Subject to any disclaimer, the term of this patent is extended or adjusted under 35 U.S.C. 154(b) by 0 days.

(21) Appl. No.: 17/843,866

(22) Filed: Jun. 17, 2022

(51) Int. Cl.
    *C07K 14/47* (2006.01)
    *A61K 38/00* (2006.01)

(52) U.S. Cl.
    CPC .......... *C07K 14/4723* (2013.01); *A61K 38/00* (2013.01)

(58) Field of Classification Search
    None
    See application file for complete search history.

(56) References Cited

U.S. PATENT DOCUMENTS

| | | |
|---|---|---|
| 4,554,101 A | 11/1985 | Hopp |
| 5,459,235 A | 10/1995 | Selsted et al. |
| 6,300,489 B1 | 10/2001 | Oh et al. |
| 9,044,020 B2 | 6/2015 | Chang et al. |
| 9,567,381 B2 | 2/2017 | Kennedy et al. |
| 9,925,223 B2 | 3/2018 | Kaznessis et al. |
| 10,231,450 B2 | 3/2019 | Van Der Weerden et al. |
| 10,470,459 B2 | 11/2019 | Schwarz |
| 11,535,653 B2 | 12/2022 | Carlson et al. |
| 2002/0162135 A1 | 10/2002 | Daniell |
| 2004/0087771 A1 | 5/2004 | Lamberty et al. |
| 2011/0010802 A1 | 1/2011 | Shah et al. |
| 2014/0086865 A1 | 3/2014 | Neff et al. |
| 2015/0045287 A1 | 2/2015 | Chen et al. |
| 2016/0279175 A1 | 9/2016 | Kaznessis et al. |
| 2018/0327461 A1 | 11/2018 | Durvasula et al. |
| 2019/0040407 A1 | 2/2019 | Guerineau et al. |
| 2019/0144510 A1 | 5/2019 | Shih et al. |

FOREIGN PATENT DOCUMENTS

| | | | |
|---|---|---|---|
| EP | 2702070 A1 | 3/2014 | |
| WO | 2006080032 A2 | 8/2006 | |
| WO | 2013134734 A2 | 9/2013 | |
| WO | WO2020146360 A1 * | 7/2020 | ............... A01H 6/46 |

OTHER PUBLICATIONS

Hashimoto, Y. et al. "Location and Nucleotide Sequence of the Gene Encoding the Viral Enhancing Factor of the Trichoplusia Ni Granulosis Vrus" Journal of General Virology, 1991, 72, 2645-2651.
Kyte and Doolittle, "A Simple Method for Displaying the Hydropathic Character of a Protein", J Mol Biol. 1982, 157(1):105-32.
Young, T.S. and Schultz P. G., "Beyond the Canonical 20 Amino Acids: Expanding the Genetic Lexicon," J. Biol. Chem. 2010, 285, pp. 11039-11044.
Conrad et al., "Compartment-specific Accumulation of Recombinant Immunoglobulins in Plant Cells: an Essential Tool for Antibody Production and Immunomodulation of Physiological Functions and Pathogen Activity", Plant Mol. Biol., 1998 38:101-109.
Stoger et al., "Cereal Crops as Viable Production and Storage Systems for Pharmaceutical scFv Antibodies", Plant Mol. Biol. 2000, 42:583-590.
Kramer, K.J. et al. "Sequence of a cDNA and Expression of the Gene Encoding Epidermal and Gut Chitinases of Manduca Sexta" Insect Biochemistry and Molecular Biology, Sep. 1993, vol. 23, Issue 6, pp. 691-701.
Uniprot Accession No. A0A0U8TEW4. Nodule Cysteine-rich Protein 7, Sep. 12, 2018. See https://www.uniprot.org/uniprotkb/A0A0U8TEW4/entry.
Lima, R. et al., "Legume Plant Peptides as Sources of Novel Antimicrobial Molecules Against Human Pathogens", Frontiers in Mol. Biosci., Jun. 9, 2022, vol. 9, pp. 1-12.
PCT International Search Report for PCT/US2020/012550 dated Jan. 7, 2019.
Montiel et al., "Terminal Bacteroid Differentiation is Associated with Variable Morphological Changes in Legume Species Belonging to the Inverted Repeat-Lacking Clade", MPMI 2016, vol. 29, No. 3, pp. 210-219.
Isozumi et al., Structure and Antimicrobial Activity of NCR169, a Nodule-specific Cysteine-rich Peptide of Medicago truncatula, Nature Sci. Rep., May 10, 2021, 11:9923.
Haag et al., Role of Cysteine Residues and Disulfide Bonds in the Activity of a Legume Root Nodule-specific, Cysteine-rich Peptide, J. Bio. Chem., Mar. 30, 2012, vol. 287, No. 14, pp. 10791-10798.
Farkas et al., Antimicrobial Activity of NCR Plant Peptides Strongly Depends on the Test Assays, Frontiers in Microbiology, Oct. 2018, vol. 9, Article 2600, pp. 1-10.
Balogh et al., Anti-chlamydial Effect of Plant Peptides, Acta Microbiol Immunol Hung. Jun. 2014; 61(2): 229-39.
Sagaram et al., Structure-activity Determinants in Antifungal Plant Defensins MsDef1 and MtDef4 with Different Modes of Action Against Fusarium graminearum, PLoS ONE, Apr. 2011, vol. 6, Issue 4, e18550.
Kereszt et al., Impact of Plant Peptides on Symbiotic Nodule Development and Functioning, Frontiers in Plant Sci. Jul. 17, 2018, vol. 9, Article 1026.
Ordogh et al., Symbiotic Plant Peptides Eliiminate Candida albicans Both in Vitro and in an Epithelial Infection Model and Inhibit the Proliferation of Immortalized Human Cells, BioMed Res. Intl. Aug. 28, 2014, vol. 2014, No. 320796.
Sagaram et al., Structural and Functional Studies of a Phosphatidic Acid-binding Antifungal Plant Defensin MtDef4: Indentification of an RGFRRR Motif Governing Fungal Cell Entry, PLoS ONE, Dec. 2018, vol. 8, Issue 12, e82485.

(Continued)

Primary Examiner — Aradhana Sasan
Assistant Examiner — Jia-Hai Lee
(74) Attorney, Agent, or Firm — Honigman LLP; Fernando Alberdi; Jonathan P. O'Brien

(57) ABSTRACT

Engineered, non-naturally occurring antimicrobial NCR13 variant peptides (NVPs), or agriculturally acceptable salts thereof, are described, along with methods of making and using the same. The present disclosure is also related to and describes novel antimicrobial compositions, formulations, and methods of using the same, that are useful for the control of pathogenic microbes.

10 Claims, 11 Drawing Sheets
Specification includes a Sequence Listing.

(56) References Cited

OTHER PUBLICATIONS

Shabab et al., Disulfide Cross-linking Influences Symbiotic Activities of Nodule Peptide NCR247, PNAS, Sep. 6, 2016, vol. 113, No. 36, pp. 10157-10162.
Szerencses et al., Symbiotic NCR Peptide Fragments Affect the Viability, Morphology, and Biofilm Formation of Candida Species, Int. J. Mol. Sci. 2021, 22, 3666.

* cited by examiner

SEQUENCE LISTING

```
<160> NUMBER OF SEQ ID NOS: 66

<210> SEQ ID NO 1
<211> LENGTH: 32
<212> TYPE: PRT
<213> ORGANISM: Cicer arietinum

<400> SEQUENCE: 1

Thr Lys Pro Cys Gln Ser Asp Lys Asp Cys Lys Lys Phe Ala Cys Arg
1               5                   10                  15

Lys Pro Lys Val Pro Lys Cys Ile Asn Gly Phe Cys Lys Cys Val Arg
            20                  25                  30

<210> SEQ ID NO 2
<211> LENGTH: 33
<212> TYPE: PRT
<213> ORGANISM: Artificial Sequence
<220> FEATURE:
<223> OTHER INFORMATION: NCR13a

<400> SEQUENCE: 2

Gly Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 3
<211> LENGTH: 33
<212> TYPE: PRT
<213> ORGANISM: Artificial Sequence
<220> FEATURE:
<223> OTHER INFORMATION: NCR13M1

<400> SEQUENCE: 3

Ala Thr Lys Pro Cys Gln Ser Asp Lys Asp Cys Lys Lys Phe Ala Cys
1               5                   10                  15
```

Arg Lys Pro Lys Val Pro Lys Cys Ile Asn Gly Phe Cys Lys Cys Val
            20                  25                  30

Arg

<210> SEQ ID NO 4
<211> LENGTH: 33
<212> TYPE: PRT
<213> ORGANISM: Artificial Sequence
<220> FEATURE:
<223> OTHER INFORMATION: NCR13M2

<400> SEQUENCE: 4

Val Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 5
<211> LENGTH: 33
<212> TYPE: PRT
<213> ORGANISM: Artificial Sequence
<220> FEATURE:
<223> OTHER INFORMATION: NCR13M3

<400> SEQUENCE: 5

Leu Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 6
<211> LENGTH: 33
<212> TYPE: PRT
<213> ORGANISM: Artificial Sequence
<220> FEATURE:
<223> OTHER INFORMATION: NCR13M4

<400> SEQUENCE: 6

Ile Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 7
<211> LENGTH: 33
<212> TYPE: PRT
<213> ORGANISM: Artificial Sequence
<220> FEATURE:
<223> OTHER INFORMATION: NCR13M5

<400> SEQUENCE: 7

Met Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

```
<210> SEQ ID NO 8
<211> LENGTH: 33
<212> TYPE: PRT
<213> ORGANISM: Artificial Sequence
<220> FEATURE:
<223> OTHER INFORMATION: NCR13M6

<400> SEQUENCE: 8

Phe Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 9
<211> LENGTH: 33
<212> TYPE: PRT
<213> ORGANISM: Artificial Sequence
<220> FEATURE:
<223> OTHER INFORMATION: NCR13M7

<400> SEQUENCE: 9

Trp Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 10
<211> LENGTH: 33
<212> TYPE: PRT
<213> ORGANISM: Artificial Sequence
<220> FEATURE:
<223> OTHER INFORMATION: NCR13M8

<400> SEQUENCE: 10

Pro Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 11
<211> LENGTH: 33
<212> TYPE: PRT
<213> ORGANISM: Artificial Sequence
<220> FEATURE:
<223> OTHER INFORMATION: NCR13M9

<400> SEQUENCE: 11

Ser Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 12
<211> LENGTH: 33
<212> TYPE: PRT
<213> ORGANISM: Artificial Sequence
<220> FEATURE:
<223> OTHER INFORMATION: NCR13M10
```

```
<400> SEQUENCE: 12

Thr Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
                20                  25                  30

Arg

<210> SEQ ID NO 13
<211> LENGTH: 33
<212> TYPE: PRT
<213> ORGANISM: Artificial Sequence
<220> FEATURE:
<223> OTHER INFORMATION: NCR13M11

<400> SEQUENCE: 13

Tyr Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
                20                  25                  30

Arg

<210> SEQ ID NO 14
<211> LENGTH: 33
<212> TYPE: PRT
<213> ORGANISM: Artificial Sequence
<220> FEATURE:
<223> OTHER INFORMATION: NCR13M12

<400> SEQUENCE: 14

Asn Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
                20                  25                  30

Arg

<210> SEQ ID NO 15
<211> LENGTH: 33
<212> TYPE: PRT
<213> ORGANISM: Artificial Sequence
<220> FEATURE:
<223> OTHER INFORMATION: NCR13M13

<400> SEQUENCE: 15

Gln Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
                20                  25                  30

Arg

<210> SEQ ID NO 16
<211> LENGTH: 33
<212> TYPE: PRT
<213> ORGANISM: Artificial Sequence
<220> FEATURE:
<223> OTHER INFORMATION: NCR13M14

<400> SEQUENCE: 16

Asp Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
                20                  25                  30
```

<210> SEQ ID NO 17
<211> LENGTH: 33
<212> TYPE: PRT
<213> ORGANISM: Artificial Sequence
<220> FEATURE:
<223> OTHER INFORMATION: NCR13M15

<400> SEQUENCE: 17

Glu Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 18
<211> LENGTH: 33
<212> TYPE: PRT
<213> ORGANISM: Artificial Sequence
<220> FEATURE:
<223> OTHER INFORMATION: NCR13M16

<400> SEQUENCE: 18

Lys Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 19
<211> LENGTH: 33
<212> TYPE: PRT
<213> ORGANISM: Artificial Sequence
<220> FEATURE:
<223> OTHER INFORMATION: NCR13M17

<400> SEQUENCE: 19

His Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg

<210> SEQ ID NO 20
<211> LENGTH: 99
<212> TYPE: DNA
<213> ORGANISM: Artificial Sequence
<220> FEATURE:
<223> OTHER INFORMATION: NCR13a

<400> SEQUENCE: 20
ggaaccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 21
<211> LENGTH: 96
<212> TYPE: DNA
<213> ORGANISM: Cicer arietinum

<400> SEQUENCE: 21
accaaaccat gtcaatctga caaagattgc aagaagttcg cttgtagaaa accaaaggtc    60
cctaaatgta ttaatggttt ctgcaagtgc gtaaga                              96

<210> SEQ ID NO 22
<211> LENGTH: 99
<212> TYPE: DNA
<213> ORGANISM: Artificial Sequence
<220> FEATURE:
<223> OTHER INFORMATION: NCR13M1

<400> SEQUENCE: 22
gcaaccaaac catgtcaatc tgacaaagat tgcaagaagt tcgcttgtag aaaaccaaag    60
gtccctaaat gtattaatgg tttctgcaag tgcgtaaga                           99

<210> SEQ ID NO 23
<211> LENGTH: 99
<212> TYPE: DNA
<213> ORGANISM: Artificial Sequence
<220> FEATURE:
<223> OTHER INFORMATION: NCR13M2

<400> SEQUENCE: 23
gtaaccaaac catgtcaatc tgacaaagat tgcaagaagt tcgcttgtag aaaaccaaag    60
gtccctaaat gtattaatgg tttctgcaag tgcgtaaga                           99

<210> SEQ ID NO 24
<211> LENGTH: 99
<212> TYPE: DNA
<213> ORGANISM: Artificial Sequence
<220> FEATURE:
<223> OTHER INFORMATION: NCR13M3

<400> SEQUENCE: 24
ttaaccaaac catgtcaatc tgacaaagat tgcaagaagt tcgcttgtag aaaaccaaag    60
gtccctaaat gtattaatgg tttctgcaag tgcgtaaga                           99

<210> SEQ ID NO 25
<211> LENGTH: 99
<212> TYPE: DNA
<213> ORGANISM: Artificial Sequence
<220> FEATURE:
<223> OTHER INFORMATION: NCR13M4

<400> SEQUENCE: 25
ataaccaaac catgtcaatc tgacaaagat tgcaagaagt tcgcttgtag aaaaccaaag    60
gtccctaaat gtattaatgg tttctgcaag tgcgtaaga                           99

<210> SEQ ID NO 26
<211> LENGTH: 99
<212> TYPE: DNA
<213> ORGANISM: Artificial Sequence
<220> FEATURE:
<223> OTHER INFORMATION: NCR13M5

<400> SEQUENCE: 26
atgaccaaac catgtcaatc tgacaaagat tgcaagaagt tcgcttgtag aaaaccaaag    60
gtccctaaat gtattaatgg tttctgcaag tgcgtaaga                           99

<210> SEQ ID NO 27
<211> LENGTH: 99
<212> TYPE: DNA
<213> ORGANISM: Artificial Sequence -continued

<220> FEATURE:
<223> OTHER INFORMATION: NCR13M6

<400> SEQUENCE: 27
ttcaccaaac catgtcaatc tgacaaagat tgcaagaagt tcgcttgtag aaaaccaaag    60
gtccctaaat gtattaatgg tttctgcaag tgcgtaaga                          99

<210> SEQ ID NO 28
<211> LENGTH: 99
<212> TYPE: DNA
<213> ORGANISM: Artificial Sequence
<220> FEATURE:
<223> OTHER INFORMATION: NCR13M7

<400> SEQUENCE: 28
tggaccaaac catgtcaatc tgacaaagat tgcaagaagt tcgcttgtag aaaaccaaag    60
gtccctaaat gtattaatgg tttctgcaag tgcgtaaga                          99

<210> SEQ ID NO 29
<211> LENGTH: 99
<212> TYPE: DNA
<213> ORGANISM: Artificial Sequence
<220> FEATURE:
<223> OTHER INFORMATION: NCR13M8

<400> SEQUENCE: 29
ccaaccaaac catgtcaatc tgacaaagat tgcaagaagt tcgcttgtag aaaaccaaag    60
gtccctaaat gtattaatgg tttctgcaag tgcgtaaga                          99

<210> SEQ ID NO 30
<211> LENGTH: 99
<212> TYPE: DNA
<213> ORGANISM: Artificial Sequence
<220> FEATURE:
<223> OTHER INFORMATION: NCR13M9

<400> SEQUENCE: 30
tcaaccaaac catgtcaatc tgacaaagat tgcaagaagt tcgcttgtag aaaaccaaag    60
gtccctaaat gtattaatgg tttctgcaag tgcgtaaga                          99

<210> SEQ ID NO 31
<211> LENGTH: 99
<212> TYPE: DNA
<213> ORGANISM: Artificial Sequence
<220> FEATURE:
<223> OTHER INFORMATION: NCR13M10

<400> SEQUENCE: 31
acaaccaaac catgtcaatc tgacaaagat tgcaagaagt tcgcttgtag aaaaccaaag    60
gtccctaaat gtattaatgg tttctgcaag tgcgtaaga                          99

<210> SEQ ID NO 32
<211> LENGTH: 99
<212> TYPE: DNA
<213> ORGANISM: Artificial Sequence
<220> FEATURE:
<223> OTHER INFORMATION: NCR13M11

<400> SEQUENCE: 32
tacaccaaac catgtcaatc tgacaaagat tgcaagaagt tcgcttgtag aaaaccaaag    60
gtccctaaat gtattaatgg tttctgcaag tgcgtaaga                          99

```
<210> SEQ ID NO 33
<211> LENGTH: 99
<212> TYPE: DNA
<213> ORGANISM: Artificial Sequence
<220> FEATURE:
<223> OTHER INFORMATION: NCR13M12

<400> SEQUENCE: 33
aataccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 34
<211> LENGTH: 99
<212> TYPE: DNA
<213> ORGANISM: Artificial Sequence
<220> FEATURE:
<223> OTHER INFORMATION: NCR13M13

<400> SEQUENCE: 34
caaaccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 35
<211> LENGTH: 99
<212> TYPE: DNA
<213> ORGANISM: Artificial Sequence
<220> FEATURE:
<223> OTHER INFORMATION: NCR13M14

<400> SEQUENCE: 35
gataccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 36
<211> LENGTH: 99
<212> TYPE: DNA
<213> ORGANISM: Artificial Sequence
<220> FEATURE:
<223> OTHER INFORMATION: NCR13M15

<400> SEQUENCE: 36
gaaaccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 37
<211> LENGTH: 99
<212> TYPE: DNA
<213> ORGANISM: Artificial Sequence
<220> FEATURE:
<223> OTHER INFORMATION: NCR13M16

<400> SEQUENCE: 37
aagaccaaac catgtcaatc tgacaaagat tgcaagaagt tcgcttgtag aaaaccaaag      60
gtccctaaat gtattaatgg tttctgcaag tgcgtaaga                            99

<210> SEQ ID NO 38
<211> LENGTH: 99
<212> TYPE: DNA
<213> ORGANISM: Artificial Sequence
<220> FEATURE:
<223> OTHER INFORMATION: NCR13M17

<400> SEQUENCE: 38
```

```
cataccaaac catgtcaatc tgacaaagat tgcaagaagt tcgcttgtag aaaaccaaag    60
gtccctaaat gtattaatgg tttctgcaag tgcgtaaga                           99
```

<210> SEQ ID NO 39
<211> LENGTH: 4
<212> TYPE: PRT
<213> ORGANISM: Artificial Sequence
<220> FEATURE:
<223> OTHER INFORMATION: IGER

<400> SEQUENCE: 39

Ile Gly Glu Arg
1

<210> SEQ ID NO 40
<211> LENGTH: 5
<212> TYPE: PRT
<213> ORGANISM: Artificial Sequence
<220> FEATURE:
<223> OTHER INFORMATION: EEKKN

<400> SEQUENCE: 40

Glu Glu Lys Lys Asn
1               5

<210> SEQ ID NO 41
<211> LENGTH: 8
<212> TYPE: PRT
<213> ORGANISM: Artificial Sequence
<220> FEATURE:
<223> OTHER INFORMATION: ETMFKHGL

<400> SEQUENCE: 41

Glu Thr Met Phe Lys His Gly Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Linker

<400> SEQUENCE: 42

Ala Leu Lys Phe Leu Val
1               5

<210> SEQ ID NO 43
<211> LENGTH: 6
<212> TYPE: PRT
<213> ORGANISM: Artificial Sequence
<220> FEATURE:
<223> OTHER INFORMATION: Linker

<400> SEQUENCE: 43

Ala Leu Lys Leu Phe Val
1               5

<210> SEQ ID NO 44
<211> LENGTH: 6
<212> TYPE: PRT
<213> ORGANISM: Artificial Sequence
<220> FEATURE:
<223> OTHER INFORMATION: Linker

<400> SEQUENCE: 44

```
Ile Phe Val Arg Leu Arg
1               5

<210> SEQ ID NO 45
<211> LENGTH: 6
<212> TYPE: PRT
<213> ORGANISM: Artificial Sequence
<220> FEATURE:
<223> OTHER INFORMATION: Linker

<400> SEQUENCE: 45

Leu Phe Ala Ala Pro Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Linker

<400> SEQUENCE: 46

Ala Leu Lys Phe Leu Val Gly Ser
1               5

<210> SEQ ID NO 47
<211> LENGTH: 8
<212> TYPE: PRT
<213> ORGANISM: Artificial Sequence
<220> FEATURE:
<223> OTHER INFORMATION: Linker

<400> SEQUENCE: 47

Ala Leu Lys Leu Phe Val Gly Ser
1               5

<210> SEQ ID NO 48
<211> LENGTH: 8
<212> TYPE: PRT
<213> ORGANISM: Artificial Sequence
<220> FEATURE:
<223> OTHER INFORMATION: Linker

<400> SEQUENCE: 48

Ile Phe Val Arg Leu Arg Gly Ser
1               5

<210> SEQ ID NO 49
<211> LENGTH: 8
<212> TYPE: PRT
<213> ORGANISM: Artificial Sequence
<220> FEATURE:
<223> OTHER INFORMATION: Linker

<400> SEQUENCE: 49

Leu Phe Ala Ala Pro Phe Gly Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Linker

<400> SEQUENCE: 50
```

Leu Phe Val Arg Leu Arg Gly Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Linker

<400> SEQUENCE: 51

Leu Gly Glu Arg Gly Ser
1               5

<210> SEQ ID NO 52
<211> LENGTH: 24
<212> TYPE: PRT
<213> ORGANISM: Hordeum vulgare

<400> SEQUENCE: 52

Met Ala Asn Lys His Leu Ser Leu Ser Leu Phe Val Leu Leu Gly
1               5                   10                  15

Leu Ser Ala Ser Leu Ala Ser Gly
            20

<210> SEQ ID NO 53
<211> LENGTH: 27
<212> TYPE: PRT
<213> ORGANISM: Nicotiana plumbaginifolia

<400> SEQUENCE: 53

Glu Met Gly Lys Met Ala Ser Leu Phe Ala Ser Leu Leu Val Leu
1               5                   10                  15

Val Ser Leu Ser Leu Ala Ser Glu Ser Ser Ala
            20                  25

<210> SEQ ID NO 54
<211> LENGTH: 26
<212> TYPE: PRT
<213> ORGANISM: Nicotiana plumbaginifolia

<400> SEQUENCE: 54

Met Gly Lys Met Ala Ser Leu Phe Ala Thr Phe Leu Val Val Leu Val
1               5                   10                  15

Ser Leu Ser Leu Ala Ser Glu Ser Ser Ala
            20                  25

<210> SEQ ID NO 55
<211> LENGTH: 78
<212> TYPE: DNA
<213> ORGANISM: Nicotiana plumbaginifolia

<400> SEQUENCE: 55
atgggtaaga tggcttctct gtttgcttct ctgctggttg ttctggtttc tctgtctctg     60
gcttctgaat cttctgct                                                   78

<210> SEQ ID NO 56
<211> LENGTH: 78
<212> TYPE: DNA
<213> ORGANISM: Nicotiana plumbaginifolia

<400> SEQUENCE: 56
atgggtaaga tggcttctct gtttgctact tttctggttg ttctggtttc tctgtctctg     60

```
gcttctgaat cttctgct                                                        78
```

<210> SEQ ID NO 57
<211> LENGTH: 238
<212> TYPE: PRT
<213> ORGANISM: Aequorea victoria

<400> SEQUENCE: 57

Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 58
<211> LENGTH: 224
<212> TYPE: PRT
<213> ORGANISM: Juniperus ashei

<400> SEQUENCE: 58

Lys Phe Asp Ile Lys Asn Gln Cys Gly Tyr Thr Val Trp Ala Ala Gly
1               5                   10                  15

Leu Pro Gly Gly Gly Lys Arg Leu Asp Gln Gly Gln Thr Trp Thr Val
            20                  25                  30

Asn Leu Ala Ala Gly Thr Ala Ser Ala Arg Phe Trp Gly Arg Thr Gly
        35                  40                  45

Cys Thr Phe Asp Ala Ser Gly Lys Gly Ser Cys Gln Thr Gly Asp Cys
    50                  55                  60

Gly Gly Gln Leu Ser Cys Thr Val Ser Gly Ala Val Pro Ala Thr Leu
65                  70                  75                  80

Ala Glu Tyr Thr Gln Ser Asp Gln Asp Tyr Asp Val Ser Leu Val
            85                  90                  95

Asp Gly Phe Asn Ile Pro Leu Ala Ile Asn Pro Thr Asn Ala Gln Cys
            100                 105                 110

Thr Ala Pro Ala Cys Lys Ala Asp Ile Asn Ala Val Cys Pro Ser Glu
            115                 120                 125

Leu Lys Val Asp Gly Gly Cys Asn Ser Ala Cys Asn Val Phe Lys Thr
            130                 135                 140

Asp Gln Tyr Cys Cys Arg Asn Ala Tyr Val Asp Asn Cys Pro Ala Thr
145                 150                 155                 160

Asn Tyr Ser Lys Ile Phe Lys Asn Gln Cys Pro Gln Ala Tyr Ser Tyr
                165                 170                 175

Ala Lys Asp Asp Thr Ala Thr Phe Ala Cys Ala Ser Gly Thr Asp Tyr
            180                 185                 190

Ser Ile Val Phe Cys Met Ala Arg Val Ser Glu Leu Ala Phe Leu Leu
            195                 200                 205

Ala Ala Thr Leu Ala Ile Ser Leu His Met Gln Glu Ala Gly Val Val
            210                 215                 220

<210> SEQ ID NO 59
<211> LENGTH: 225
<212> TYPE: PRT
<213> ORGANISM: Juniperus ashei

<400> SEQUENCE: 59

Met Ala Arg Val Ser Glu Leu Ala Phe Leu Leu Ala Ala Thr Leu Ala
1               5                   10                  15

Ile Ser Leu His Met Gln Glu Ala Gly Val Val Lys Phe Asp Ile Lys
            20                  25                  30

Asn Gln Cys Gly Tyr Thr Val Trp Ala Ala Gly Leu Pro Gly Gly Gly
            35                  40                  45

Lys Arg Leu Asp Gln Gly Gln Thr Trp Thr Val Asn Leu Ala Ala Gly
        50                  55                  60

Thr Ala Ser Ala Arg Phe Trp Gly Arg Thr Gly Cys Thr Phe Asp Ala
65                  70                  75                  80

Ser Gly Lys Gly Ser Cys Gln Thr Gly Asp Cys Gly Gly Gln Leu Ser
            85                  90                  95

Cys Thr Val Ser Gly Ala Val Pro Ala Thr Leu Ala Glu Tyr Thr Gln
            100                 105                 110

Ser Asp Gln Asp Tyr Tyr Asp Val Ser Leu Val Asp Gly Phe Asn Ile
            115                 120                 125

Pro Leu Ala Ile Asn Pro Thr Asn Ala Gln Cys Thr Ala Pro Ala Cys
            130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Phe Lys Thr Asp Gln Tyr Cys Cys
                165                 170                 175

Arg Asn Ala Tyr Val Asp Asn Cys Pro Ala Thr Asn Tyr Ser Lys Ile
            180                 185                 190

Phe Lys Asn Gln Cys Pro Gln Ala Tyr Ser Tyr Ala Lys Asp Asp Thr
            195                 200                 205

Ala Thr Phe Ala Cys Ala Ser Gly Thr Asp Tyr Ser Ile Val Phe Cys
            210                 215                 220

Pro
225

<210> SEQ ID NO 60
<211> LENGTH: 22
<212> TYPE: DNA
<213> ORGANISM: Artificial Sequence
<220> FEATURE:
<223> OTHER INFORMATION: Forward primer: Taq-URA3-LB1

<400> SEQUENCE: 60
cgttcgactg atgagctatt ga                                              22

<210> SEQ ID NO 61
<211> LENGTH: 22
<212> TYPE: DNA
<213> ORGANISM: Artificial Sequence
<220> FEATURE:
<223> OTHER INFORMATION: Reverse primer: Taq-URA3-LB2

<400> SEQUENCE: 61
cgttcgactg atgagctatt ga                                              22

<210> SEQ ID NO 62
<211> LENGTH: 24
<212> TYPE: DNA
<213> ORGANISM: Artificial Sequence
<220> FEATURE:
<223> OTHER INFORMATION: Probe primer: Taq-URA3-Probe, reporter dye:
      FAM.

<400> SEQUENCE: 62
acgttgggtc catacatttg cctt                                            24

<210> SEQ ID NO 63
<211> LENGTH: 22
<212> TYPE: DNA
<213> ORGANISM: Artificial Sequence
<220> FEATURE:
<223> OTHER INFORMATION: Forward primer: Taq-pLAC4-LB1

<400> SEQUENCE: 63
catccaggcc aggtagaaat ag                                              22

<210> SEQ ID NO 64
<211> LENGTH: 22
<212> TYPE: DNA
<213> ORGANISM: Artificial Sequence
<220> FEATURE:
<223> OTHER INFORMATION: Reverse primer: Taq-pLAC4-LB2

<400> SEQUENCE: 64
gagcttaccc ttctcctctt tg                                              22

<210> SEQ ID NO 65
<211> LENGTH: 25
<212> TYPE: DNA
<213> ORGANISM: Artificial Sequence
<220> FEATURE:
<223> OTHER INFORMATION: Probe primer: Taq-pLAC4-Probe2, reportor dye:
      NED

<400> SEQUENCE: 65
tggcagcgta gtagagtagg taggt                                           25

<210> SEQ ID NO 66
<211> LENGTH: 33
<212> TYPE: PRT

```
<213> ORGANISM: Artificial Sequence
<220> FEATURE:
<223> OTHER INFORMATION: NCR13M18

<400> SEQUENCE: 66

Arg Thr Lys Pro Cys Gln Ser Asp Lys Asp Cys Lys Lys Phe Ala Cys
1               5                   10                  15

Arg Lys Pro Lys Val Pro Lys Cys Ile Asn Gly Phe Cys Lys Cys Val
            20                  25                  30

Arg
```

US 11,713,341 B1

ANTIMICROBIAL NCR13 VARIANT PEPTIDES

SEQUENCE LISTING

This application incorporates by reference in its entirety the revised Sequence Listing entitled "225312-512305_ST25.txt (23 KB), which was created on Feb. 9, 2023, at 4:19 PM and is filed electronically herewith.

TECHNICAL FIELD

Engineered, non-naturally occurring antimicrobial peptides and agricultural compositions and methods containing same are described.

BACKGROUND

The lives and livelihoods of millions of people depend on several agriculturally important crops. Deleterious microbes that threaten these agriculturally important crops represent a dire threat to global food security and the economy.

Microbial infections, e.g., fungal infections, are a particular problem in damp climates, and are of major concern during crop storage; indeed, the degree and severity of fungal infections can be exacerbated by modern growing methods as harvesting and storage systems frequently provide a favorable environment for these plant pathogens. Adding to the problems caused by microbial infections are the rich diversity of pathogenic microbes (e.g., fungi, bacteria, oomycetes, etc.) that can contribute to plant disease. World-wide international travel has aided in spreading these deleterious microbes to parts of the planet where native plants have evolved no defenses. Moreover, the emphasis on intensive monoculture practices of commercially relevant crops in concert with traditional disease-mitigation strategies has allowed pathogenic microbes to become resistant and thrive.

The incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Accordingly, consumers and government regulators alike are becoming increasingly concerned with the environmental hazards associated with the production and use of synthetic agrochemicals for protecting plants from pathogens. Thus, there is a significant need for novel alternatives for the control of plant pathogens that possess a lower risk of pollution and environmental hazards than is characteristic of traditional agrochemical-based methods.

Accordingly, there is a need for alternative, environmentally friendly antimicrobial agents and compositions to protect economically important commodity and staple calorie crops from the threats posed by pathogenic microbes.

SUMMARY

The present disclosure describes an engineered antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof.

In addition, the present disclosure describes a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is any natural or non-natural amino acid other than glycine or alanine; or a complementary nucleotide sequence thereof.

In addition, the present disclosure describes a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; and an excipient.

In addition, the present disclosure describes a method of combating, controlling, or inhibiting a microbe comprising applying a antimicrobially effective amount of: (1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or (2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof.

BRIEF DESCRIPTION OF THE DRAWINGS

FIG. 9 shows the slopes of the lines shown in FIG. 8. The horizontal line shows NCR13a.

DETAILED DESCRIPTION

Definitions

Figure 1:
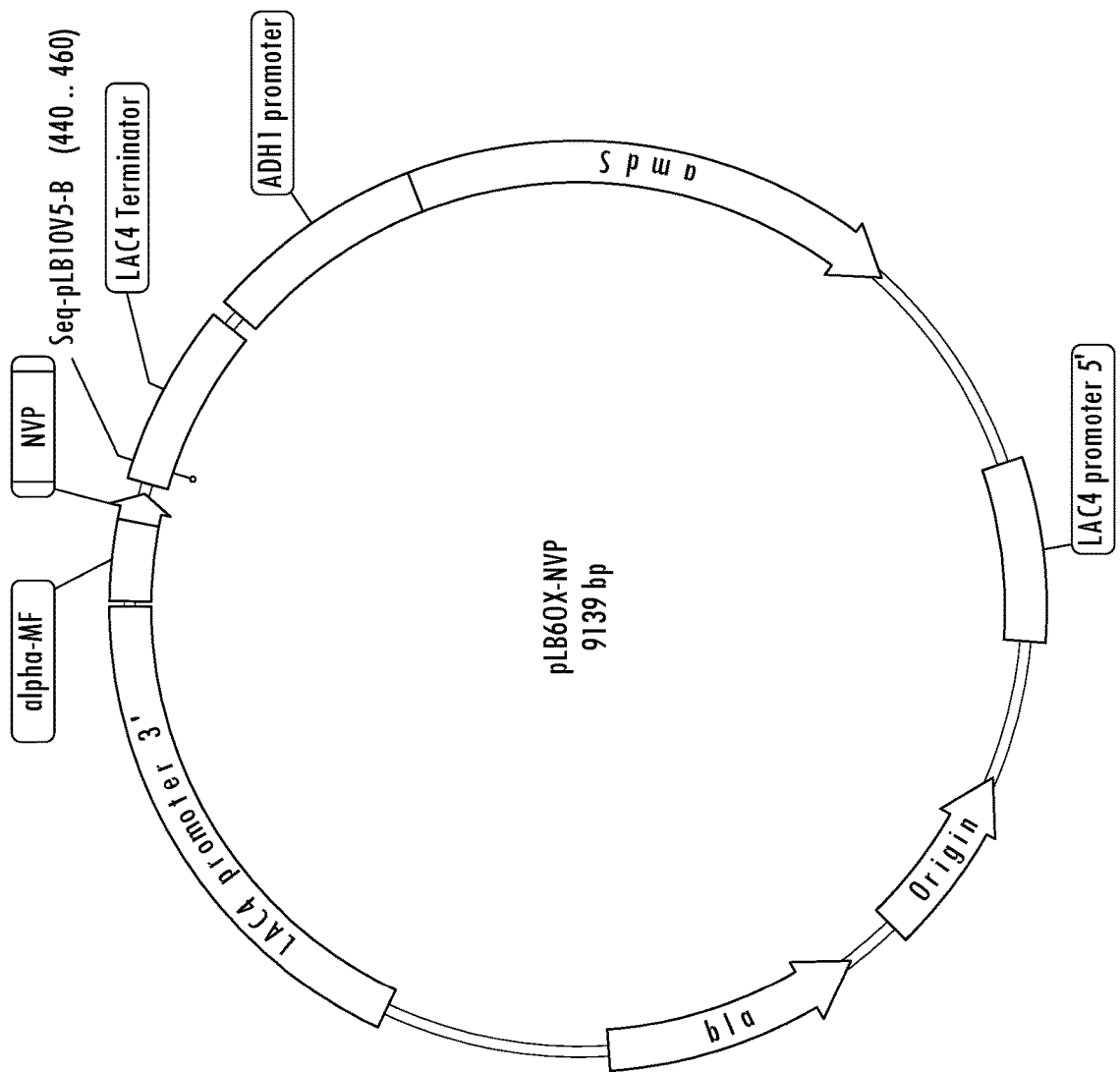
FIG. 1 shows an example of a representative plasmid map for a vector comprising a polynucleotide encoding an NCR13 variant peptide (NVP) of the present disclosure. Here, the vectors comprise the following elements: a Kex2 cleavage site (not shown); a multiple cloning site; a LAC4 terminator; and ADH1 promoter; a β-lactamase (bla) gene; and an origin of replication site.

"5'-end" and "3'-end" refers to the directionality, i.e., the end-to-end orientation of a nucleotide polymer (e.g., DNA). The 5'-end of a polynucleotide is the end of the polynucleotide that has the fifth carbon.

"5'- and 3'-homology arms" or "5' and 3' arms" or "left and right arms" refers to the polynucleotide sequences in a vector and/or targeting vector that homologously recombine with the target genome sequence and/or endogenous gene of interest in the host organism in order to achieve successful genetic modification of the host organism's chromosomal locus.

"Affect" refers to how a something influences another thing, e.g., how a peptide, polypeptide, protein, drug, or chemical influences a microbe.

"Agriculturally-acceptable carrier" covers all adjuvants, inert components, dispersants, surfactants, tackifiers, binders, etc. that are ordinarily used in agricultural formulation technology; these are well known to those skilled in agricultural formulations.

"Agriculturally acceptable salt" is synonymous with pharmaceutically acceptable salt, and as used herein refers to a compound that is modified by making acid or base salts thereof.

"Alignment" refers to a method of comparing two or more sequences (e.g., nucleotide, polynucleotide, amino acid, peptide, polypeptide, or protein sequences) for the purpose of determining their relationship to each other. Alignments are typically performed by computer programs that apply various algorithms, however, it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW (see Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV (see Larkin M. A., et al., CLUSTALW2, ClustalW and ClustalX version 2, Bioinformatics 23(21): 2947-2948, 2007); Mafft; Kalign; ProbCons; and T-Coffee (see Notredame et al., T-Coffee: A novel method for multiple sequence alignments, Journal of Molecular Biology 302: 205-217, 2000). Exemplary programs that implement one or more of the foregoing algorithms include, but are not limited to, MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In some embodiments, an alignment will introduce "phase shifts" and/or "gaps" into one or both of the sequences being compared in order to maximize the similarity between the two sequences, and scoring refers to the process of quantitatively expressing the relatedness of the aligned sequences.

"Alpha-MF signal" or "αMF secretion signal" refers to a protein that directs nascent recombinant polypeptides to the secretory pathway.

"Ameliorate" or "amelioration" includes the arrest, prevention, decrease, or improvement in one or more the symptoms, signs, and features of the disease being treated, both temporary and long-term.

As used herein, "antimicrobial" is generally used to refer to the ability of a combination or composition of the present disclosure, to increase mortality or inhibit growth rate of microbes.

"Antimicrobial effect" refers to inhibition or stoppage of the normal metabolic processes required for continued life, or continued growth of a microbe. "Antimicrobial effect" includes killing of any individual or group of microbes.

"Antimicrobial activity" means that upon or after exposing the microbe to the combinations or compositions of the present disclosure, the microbe either dies, stops, or slows its cellular processes; stops or slows its maintenance; stops or slows its growth; fails to reproduce; and the like.

"Antimicrobial composition" refers to a composition comprising a NVP, or an agriculturally acceptable salt thereof, and an excipient.

"Antimicrobially effective amount" refers to an amount of (1) an NVP, or an agriculturally acceptable salt thereof, or (2) an antimicrobial composition comprising: an NVP, or an agriculturally acceptable salt thereof, and an excipient; that is sufficient to: inhibit a microbe, bring about the death of at least one microbe; noticeably reduce or decrease microbe growth, feeding, or normal physiological development; inhibit or decrease the normal microbe cellular processes, including maintenance and growth; and/or attenuate or decrease the severity of a microbial infection. This amount will vary depending on such factors including but not limited to: the specific target microbe to be controlled; the specific environment, location, plant, crop, or agricultural site to be treated; the environmental conditions, method, rate, concentration, stability, and quantity applied. Further, those having ordinary skill in the art will recognize that the antimicrobially-effective amount may also vary with respect to climatic conditions, environmental considerations, and/or frequency of application and/or severity of microbe infestation. Antimicrobially-effective amounts can be measured by use of assays that measure the reduction in growth or decline in their populations of a microbe. One measure of reduction can be to express the decrease in population in logarithmic scale typical of a specific microbial species. That is, a 1 log reduction is equivalent to a 90% reduction versus a control, a 2 log reduction is a 99% reduction, etc.

"Applying" or "application" or "apply" or "administering" or "administration" or "administer" means to dispense and/or otherwise provide, and refers to any method of application or route of administration. For example, applying can refer to, e.g., application of a of an engineered, non-naturally occurring antimicrobial peptide (e.g., an NVP), or an agriculturally acceptable salt thereof, or an antimicrobial composition comprising an engineered, non-naturally occurring antimicrobial peptide, or an agriculturally acceptable salt thereof, and one or more excipients, e.g., a sprayable composition; a foam; a burning formulation; a fabric treatment; a surface-treatment; a dispersant; or a microencapsulation. By "co-application" or "co-administer" it is meant that a combination or composition described herein is applied or administered at the same time, just prior to, or just after the application of: an engineered, non-naturally occurring antimicrobial peptide, or an agriculturally acceptable salt thereof; and optionally, one or more additional agents or excipients, also referred to herein as a "additional agent." The NVP, or an agriculturally acceptable salt thereof, of the present disclosure, and optionally one or more excipients can be administered alone or can be co-administered to the locus of a microbe. Co-application or co-administration is meant to include simultaneous or sequential application, e.g., one or more NVPs and/or one or more NVPs and one or more excipients.

"bp" or "base pair" refers to a molecule comprising two chemical bases bonded to one another. For example, a DNA molecule consists of two winding strands, wherein each strand has a backbone made of an alternating deoxyribose and phosphate groups. Attached to each deoxyribose is one of four bases, i.e., adenine (A), cytosine (C), guanine (G), or thymine (T), wherein adenine forms a base pair with thymine, and cytosine forms a base pair with guanine.

"C-terminus" or "C-terminal" refers to the free carboxyl group (i.e., —COOH) that is positioned on the terminal end of a polypeptide.

The term "conservative amino acid substitutions" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologs). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment of the homologs). However, one of skill in the art would understand that functional variants may have minor conserved or nonconserved alterations in the conserved residues. Guidance as to appropriate amino acid substitutions that do not affect biological activity of the protein of interest may be found in the model of Dayhoff, et al., (1978) Atlas of Protein Sequence and Structure (Natl. Biomed. Res. Found., Washington, D.C.), herein incorporated by reference.

In making such changes, the hydropathic index of amino acids may be considered. The importance of the hydropathic amino acid index in conferring interactive biologic function on a protein is generally understood in the art (Kyte and Doolittle, (1982) J Mol Biol. 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

"Culture" or "cell culture" refers to the maintenance of cells in an artificial, in vitro environment.

"Culturing" refers to the propagation of organisms on or in various kinds of media. For example, the term "culturing" can mean growing a population of cells under suitable conditions in a liquid or solid medium. In some embodiments, culturing refers to fermentative recombinant production of a peptide of interest (e.g., an NVP) and/or other desired end products (typically in a vessel or reactor).

"Decreasing" or "decrease" or "decreased" or "reducing" or "reduced" or "a reduction" or "inhibiting" or "stopping" or "combatting" or "controlling" or any variation of these terms, refers to making something (e.g., the number of microbes and/or degree or severity of a microbe infection or disease) less in size, amount, intensity, or degree. For example, in some embodiments, the application of a antimicrobially-effective amount of an NVP of the present disclosure, or an agriculturally acceptable salt thereof, and/or an antimicrobial composition comprising: an NVP, or an agriculturally acceptable salt thereof, and an excipient; to the locus of the microbe, or to a plant or animal susceptible to an attack by the microbe, can result in the following effect: a decrease or reduction in the number of microbes and/or a decrease or reduction in the degree or severity of a microbe infection or disease, relative to the number of microbes and/or degree or severity of a microbe infection or disease that has not been treated with, or had applied thereto, an antimicrobially-effective amount of an NVP, or an agriculturally acceptable salt thereof, and/or an antimicrobial composition comprising: an NVP, or an agriculturally acceptable salt thereof, and an excipient, as described herein.

In some embodiments, reducing or decreasing, e.g., the number of microbes and/or the degree or severity of a microbe infection or disease, includes any measurable decrease or complete inhibition to achieve a desired result. For example, there may be a decrease of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more, in the number of microbes and/or degree or severity of a microbe infection or disease, when a plant or animal susceptible to a pathogenic microbe is treated with the antimicrobial combinations or antimicrobial compositions of the present disclosure, as compared to normal. The term "about" as used herein means within +10%, preferably +5% of a given value. Thus, in some embodiments, the terms "reduction in the number of microbes and/or degree or severity of a microbe infection or disease," refers to a decrease or reduction in the number of microbes and/or degree or severity of a microbe infection or disease by a plant or animal susceptible to an attack by the microbe that has received an antimicrobially effective amount of a combination of the present disclosure, or an agricultural composition thereof, that is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.25%, at least about 1.5%, at least about 1.75%, at least about 2%, at least about 2.25%, at least about 2.5%, at least about 2.75%, at least about 3%, at least about 3.25%, at least about 3.5%, at least about 3.75%, at least about 4%, at least about 4.25%, at least about 4.5%, at least about 4.75%, at least about 5%, at least about 5.25%, at least about 5.5%, at least about 5.75%, at least about 6%, at least about 6.25%, at least about 6.5%, at least about 6.75%, at least about 7%, at least about 7.25%, at least about 7.5%, at least about 7.75%, at least about 8%, at least about 8.25%, at least about 8.5%, at least about 8.75%, at least about 9%, at least about 9.25%, at least about 9.5%, at least about 9.75%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 80%, at least about 85%, at least about 90%, at least about 95%, at least about 100%, or a greater than a 100%, relative to the number of microbes and/or degree or severity of a microbe infection or disease in a plant or animal susceptible to an attack by the microbe that has not been administered an antimicrobially effective amount of an NVP of the present disclosure, or an agricultural composition thereof.

"DNA" refers to deoxyribonucleic acid, comprising a polymer of one or more deoxyribonucleotides or nucleotides (i.e., adenine [A], guanine [G], thymine [T], or cytosine [C]), which can be arranged in single-stranded or double-stranded form. For example, one or more nucleotides creates a polynucleotide.

"Excipient" refers to any agriculturally acceptable additive, carrier, surfactant, emulsifier, thickener, preservative, solvent, disintegrant, glidant, lubricant, diluent, filler, bulking agent, binder, emollient, stiffening agent, stabilizer, solubilizing agents, dispersing agent, suspending agent, antioxidant, antiseptic, wetting agent, humectant, fragrant, suspending agents, pigments, colorants, isotonic agents, viscosity enhancing agents, mucoadhesive agents, and/or any combination thereof, that can be added to a composition, preparation, and/or formulation, which may be useful in achieving a desired modification to the characteristics of the composition, preparation, and/or formulation. Such modifications include, but are not limited to, physical stability, chemical stability, therapeutic efficacy, and/or any combination thereof. In some embodiments, excipients can be formulated alongside a an engineered, non-naturally occurring antimicrobial peptide, or an agriculturally acceptable salt thereof consisting of an amino acid sequence set forth in SEQ ID NO: 1, when preparing an antimicrobial composition, e.g., for the purpose of bulking up compositions (thus often referred to as bulking agents, fillers or diluents). In yet other embodiments, an excipient can be used to provide stability, or prevent contamination (e.g., microbial contamination). In other embodiments, an excipient can be used to confer a physical property to a composition (e.g., a composition that is a dry granular, or dry flowable powder physical form). Reference to an excipient includes both one and more than one such excipients. Suitable excipients are described in Remington's Pharmaceutical Sciences, by E. W. Martin, the disclosure of which is incorporated herein by reference in its entirety.

"Expression cassette" refers to (1) a DNA sequence of interest, e.g., a polynucleotide operable to encode an NVP; and one or more of the following: (2) promoters, terminators, and/or enhancer elements; (3) an appropriate mRNA stabilizing polyadenylation signal; (4) an internal ribosome entry site (IRES); (5) introns; and/or (6) post-transcriptional regulatory elements. The combination (1) with at least one of (2)-(6) is called an "expression cassette." In some embodiments, there can be numerous expression cassettes cloned into a vector. For example, in some embodiments, there can be a first expression cassette comprising a polynucleotide operable to encode an NVP. In alternative embodiments, there are two expression cassettes, each comprising a polynucleotide operable to encode an NVP (i.e., a double expression cassette). In other embodiments, there are three expression cassettes operable to encode an NVP (i.e., a triple expression cassette). In some embodiments, a double expression cassette can be generated by subcloning a second expression cassette into a vector containing a first expression cassette. In some embodiments, a triple expression cassette can be generated by subcloning a third expression cassette into a vector containing a first and a second expression cassette. Methods concerning expression cassettes and cloning techniques are well-known in the art and described herein. See also NVP expression cassette.

"Fermentation beer" refers to spent fermentation medium, i.e., fermentation medium supernatant after removal of organisms, that has been inoculated with and consumed by a transformed host cell (e.g., a yeast cell operable to express an NVP of the present disclosure). In some embodiments, fermentation beer refers to the solution that is recovered following the fermentation of the transformed host cell. The term "fermentation" refers broadly to the enzymatic and anaerobic or aerobic breakdown of organic substances (e.g., a carbon substrate) nutrient substances by microorganisms under controlled conditions (e.g., temperature, oxygen, pH, nutrients, and the like) to produce fermentation products (e.g., one or more peptides of the present disclosure). While fermentation typically describes processes that occur under anaerobic conditions, as used herein it is not intended that the term be solely limited to strict anaerobic conditions, as the term "fermentation" used herein may also occur processes that occur in the presence of oxygen.

"GFP" means green fluorescent protein from the jellyfish, *Aequorea victoria*.

"Growth medium" refers to a nutrient medium used for growing cells in vitro.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. Thus, in some embodiments, the term "homologous" refers to the sequence similarity between two polypeptide molecules, or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, if 6 of 10 of the positions in two sequences are matched or homologous then the two sequences are 60% homologous. By way of example, the DNA sequences ATTGCC and TATGGC share 50% homology.

There may be partial homology, or complete homology and thus identical. "Sequence identity" refers to a measure of relatedness between two or more nucleic acid sequences or two or more polypeptide sequences, and is given as a percentage with reference to the total comparison length. The identity calculation takes into account those nucleotide residues or amino acid residues that are identical and in the same relative positions in their respective larger sequences.

"Homologous recombination" refers to the event of substitution of a segment of DNA by another one that possesses identical regions (homologous) or nearly so. For example, in some embodiments, "homologous recombination" refers to a type of genetic recombination in which nucleotide sequences are exchanged between two similar or identical molecules of DNA. Briefly, homologous recombination is most widely used by cells to accurately repair harmful breaks that occur on both strands of DNA, known as double-strand breaks. Although homologous recombination varies widely among different organisms and cell types, most forms involve the same basic steps: after a double-strand break occurs, sections of DNA around the 5' ends of the break are cut away in a process called resection. In the strand invasion step that follows, an overhanging 3' end of the broken DNA molecule then "invades" a similar or identical DNA molecule that is not broken. After strand invasion, the further sequence of events may follow either of two main pathways, i.e., the double-strand break repair pathway, or the synthesis-dependent strand annealing pathway. Homologous recombination is conserved across all three domains of life as well as viruses, suggesting that it is a nearly universal biological mechanism. For example, in some embodiments, homologous recombination can occur using a site-specific integration (SSI) sequence, whereby there is a strand exchange crossover event between nucleic acid sequences substantially similar in nucleotide composition. These crossover events can take place between sequences contained in the targeting construct of the invention (i.e., the SSI sequence) and endogenous genomic nucleic acid sequences (e.g., the polynucleotide encoding the peptide subunit). In addition, in some embodiments, it is possible that more than one site-specific homologous recombination event can occur, which would result in a replacement event in which nucleic acid sequences contained within the targeting construct have replaced specific sequences present within the endogenous genomic sequences.

"Hybridize" refers to the annealing of one single-stranded polynucleotide to another polynucleotide based on the well-understood principle of sequence complementarity. In some embodiments, the other polynucleotide is a single-stranded polynucleotide. The propensity for hybridization between polynucleotides depends on the temperature and ionic strength of their milieu, the length of the polynucleotides, and the degree of complementarity. The effect of these parameters on hybridization are well known in the art.

"Hybridization" refers to any process by which a strand of polynucleotide binds with a complementary strand through base pairing. Two single-stranded polynucleotides "hybridize" when they form a double-stranded duplex. Thus, as used herein, the term "hybridize" refers to the annealing of one single-stranded polynucleotide to another polynucleotide based on the well-understood principle of sequence complementarity. In some embodiments, the other polynucleotide is a single-stranded polynucleotide. The propensity for hybridization between polynucleotides depends on the temperature and ionic strength of their milieu, the length of the polynucleotides, and the degree of complementarity. The effect of these parameters on hybridization are well known in the art. When two single-stranded polynucleotides hybridize and form a double-stranded duplex, the region of double-strandedness can include the full-length of one or both of the single-stranded polynucleotides, or all of one single stranded polynucleotide and a subsequence of the other single stranded polynucleotide, or the region of double-strandedness can include a subsequence of each polynucleotide. Hybridization also includes the formation of duplexes which contain certain mismatches, provided that the two strands are still forming a double stranded helix. See "Stringent hybridization conditions" below.

"$IC_{50}$" or "IC50" refers to half-maximal inhibitory concentration, which is a measurement of how much of an agent is needed to inhibit a biological process by half, thus providing a measure of potency of said agent.

"Identity" refers to a relationship between two or more polypeptide sequences or two or more polynucleotide sequences, as determined by comparing said sequences. The term "identity" also means the degree of sequence relatedness between polypeptide or polynucleotide sequences, as the case may be, as determined by the match between strings of such sequences. "Identity" and "similarity" can be readily calculated by any one of the myriad methods known to those having ordinary skill in the art, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994: Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), the disclosures of which are incorporated herein by reference in their entireties. Furthermore, methods to determine identity and similarity are codified in publicly available computer programs. For example in some embodiments, methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), the disclosures of which are incorporated herein by reference in their entireties.

"in vivo" refers to in the living body of a plant or animal (e.g., an animal, plant or a cell) and to processes or reactions that occur within the living body of a plant or animal.

"Inactive" refers to a condition wherein something is not in a state of use, e.g., lying dormant and/or not working. For example, when used in the context of a gene or when referring to a gene, the term inactive means said gene is no longer actively synthesizing a gene product, having said gene product translated into a protein, or otherwise having the gene perform its normal function. For example, in some embodiments, the term inactive can refer to the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Inhibiting" or "inhibit" or "combating" or "combat" or "controlling" or "control," or any variation of these terms, refers to making something (e.g., the number of microbes, the functions and/or activities of the microbe, and/or the deleterious effect of the microbe on a plant or animal susceptible to attack thereof) less in size, amount, intensity, or degree. For example, in some embodiments, the application of a antimicrobially effective amount of an NVP or agriculturally acceptable salt thereof, or an antimicrobial composition comprising an NVP or agriculturally acceptable salt thereof, to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination thereof, results in the following effect: a decrease in the number of microbes; an increase in the susceptibility of the microbe to one or more antimicrobial agents; and/or inhibition or impairment of one or more of the microbe's activities, such as any physiological function required for normal physiological maintenance and/or survival and/or reproduction (e.g. respiration, membrane integrity, energy utilization, synthesis of vital building blocks e.g. nucleic acids, amino acids, biochemical metabolites), growth, reproduction, and/or any other parameter that is essential to the microbe's survival and/or reproduction, relative to the number of microbes or activities thereof that had not been exposed to an antimicrobially effective amount of an NVP or agriculturally acceptable salt thereof, or an agricultural composition comprising an NVP or agriculturally acceptable salt thereof.

In some embodiments, combating, controlling, or inhibiting a microbe, includes any measurable decrease or complete inhibition to achieve a desired result. For example, there may be a decrease of about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, or more, in the number of microbes or the activities thereof treated with peptides and/or compositions of the present disclosure, compared to untreated microbes. About as used herein means within 10%, preferably ±5% of a given value.

Thus, in some embodiments, the terms "combating, controlling, or inhibiting a microbe," refers to: a decrease in the number of microbes; an increase in the susceptibility of the microbe to one or more antimicrobial agents; and/or inhibition or impairment of one or more of the microbe's activities or functions, such as any physiological function required for normal physiological maintenance and/or survival and/or reproduction (e.g. respiration, membrane integrity, energy utilization, synthesis of vital building blocks e.g. nucleic acids, amino acids, biochemical metabolites), growth, reproduction, and/or any other parameter that is essential to the microbe's survival and/or reproduction, when an antimicrobially-effective amount of an NVP of the present disclosure, or an agricultural composition thereof, is applied to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination thereof, that is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.25%, at least about 1.5%, at least about 1.75%, at least about 2%, at least about 2.25%, at least about 2.5%, at least about 2.75%, at least about 3%, at least about 3.25%, at least about 3.5%, at least about 3.75%, at least about 4%, at least about 4.25%, at least about 4.5%, at least about 4.75%, at least about 5%, at least about 5.25%, at least about 5.5%, at least about 5.75%, at least about 6%, at least about 6.25%, at least about 6.5%, at least about 6.75%, at least about 7%, at least about 7.25%, at least about 7.5%, at least about 7.75%, at least about 8%, at least about 8.25%, at least about 8.5%, at least about 8.75%, at least about 9%, at least about 9.25%, at least about 9.5%, at least about 9.75%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 80%, at least about 85%, at least about 90%, at least about 95%, at least about 100%, or a greater than a 100%, relative to the number of microbes; the level of the susceptibility of the microbes to one or more antimicrobial agents; and/or the activities or functions of the microbes that have not received an antimicrobially-effective amount of the NVP, or an agriculturally acceptable salt thereof, or a composition thereof.

"Inoperable" refers to the condition of a thing not functioning, malfunctioning, or no longer able to function. For example, when used in the context of a gene or when referring to a gene, the term inoperable means said gene is no longer able to operate as it normally would, either permanently or transiently. For example, "inoperable," in some embodiments, means that a gene is no longer able to synthesize a gene product, having said gene product translated into a protein, or is otherwise unable to gene perform its normal function. For example, in some embodiments, the term inoperable can refer the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Isolated" refers to separating a thing and/or a component from its natural environment, e.g., WT NCR13 peptide isolated from an organism means that peptide is separated from its natural environment.

"kb" refers to kilobase, i.e., 1000 bases. As used herein, the term "kb" means a length of nucleic acid molecules. For example, 1 kb refers to a nucleic acid molecule that is 1000 nucleotides long. A length of double-stranded DNA that is 1 kb long, contains two thousand nucleotides (i.e., one thousand on each strand). Alternatively, a length of single-stranded RNA that is 1 kb long, contains one thousand nucleotides.

"kDa" refers to kilodalton, a unit equaling 1,000 daltons; a "Dalton" is a unit of molecular weight (MW).

"Knockdown dose 50" or "KD$_{50}$" refers to the median dose required to cause paralysis or cessation of movement in 50% of a population.

"LC$_{50}$" or "lethal concentration 50%" refers to the concentration of an agent required to kill 50% of a population.

"Locus of a microbe" refers to the habitat of a microbe; food supply of a microbe; breeding ground of a microbe; area inhabited or colonized by a microbe; material infested, eaten, or used by a microbe; and/or any environment in which a microbe inhabits, uses, is present in, or is expected to be. In some embodiments, the locus of a microbe includes, without limitation, a microbe habitat; a microbe food supply; a microbe breeding ground; a microbe area; a microbe environment; any surface or location that may be frequented and/or infested by a microbe; any plant or animal, or a locus of a plant or animal, susceptible to attack by a microbe; and/or any surface or location where a microbe may be found, may be expected to be found, or is likely to be attacked by a microbe.

"Medium" (plural "media") refers to a nutritive solution for culturing cells in cell culture.

"Microbe" refers to any microscopic organism, e.g., any multi-cellular or uni-cellular microorganism, or a virus, including all of the prokaryotes, namely the eubacteria and archaebacteria, and various forms of eukaryote, comprising the protozoa, fungi (e.g., yeast). Thus, as used herein, "microbe" refers to all bacteria, all archaea, unicellular protista, unicellular animals, unicellular plants, unicellular fungi, unicellular algae, all protozoa, and all chromista. In some embodiments, a microbe can be a pathogenic microbe, wherein the microbe causes an infection or disease in a living organism when introduced into said organism; or wherein the presence of the microbe is deleterious to the organism. For example, in some embodiments, a microbe can be a pathogen to plants, e.g., a phytopathogen, such as a bacterium, a protozoan, or a fungus.

"MOA" refers to mechanism of action.

"Molecular weight (MW)" refers to the mass or weight of a molecule, and for proteins is typically measured in "daltons (Da)" or kilodaltons (kDa). In some embodiments, MW can be calculated using sodium dodecyl sulfate polyacrylamide gel electrophoresis (SDS-PAGE), gel chromatography, analytical ultracentrifugation, mass spectrometry, or light scattering. In some embodiments, the SDS-PAGE method is as follows: the sample of interest is separated on a gel with a set of molecular weight standards. The sample is run, and the gel is then processed with a desired stain, followed by destaining for about 2 to 14 hours. The next step is to determine the relative migration distance (Rf) of the standards and protein of interest. The migration distance can be determined using the following equation: Rf=(migration distance of the protein)/(Migration distance of the dye front). Next, the logarithm of the MW can be determined based on the values obtained for the bands in the standard; e.g., in some embodiments, the logarithm of the molecular weight of an SDS-denatured polypeptide and its relative migration distance (Rf) is plotted into a graph. After plotting the graph, interpolating the value derived will provide the molecular weight of the unknown protein band.

"Motif" refers to a polynucleotide or polypeptide sequence that is implicated in having some biological significance and/or exerts some effect or is involved in some biological process.

"Mutant" refers to an organism, DNA sequence, amino acid sequence, peptide, polypeptide, or protein, that has an alteration or variation (for example, in the nucleotide sequence or the amino acid sequence), which causes said organism and/or sequence to be different from the naturally occurring or wild-type organism, wild-type sequence, and/or reference sequence with which the mutant is being compared. In some embodiments, this alteration or variation can be one or more nucleotide and/or amino acid substitutions or modifications (e.g., deletion or addition). In some embodiments, the one or more amino acid substitutions or modifications can be conservative; here, such a conservative amino acid substitution and/or modification in a "mutant" does not substantially diminish the activity of the mutant in relation to its non-mutant form. For example, in some embodiments, a "mutant" possesses one or more conservative amino acid substitutions when compared to a peptide with a disclosed and/or claimed sequence, as indicated by a SEQ ID NO.

"N-terminus" refers to the free amine group (i.e., —NH$_2$) that is positioned on beginning or start of a polypeptide.

"N-terminus addition," as used in the context of an N-terminus addition of an amino acid, refers to the addition of an amino acid to the N-terminus of a peptide. For example, a WT-NCR13 peptide having an amino acid sequence of: TKPCQSDKDCKKFACRKPKVPKC-INGFCKCVR (SEQ ID NO: 1) (NCBI Accession No. DAA64987), can have an amino acid added or appended to the N-terminus via a peptide bond, i.e., a covalent chemical bond between the carboxyl group of the amino acid to be added (e.g., V, L, I, M, F, W, P, S, T, Y, N, Q, D, E, K, R, or H), and the amino group of the threonine (T) at the N-terminus of WT-NCR13; thus, in some embodiments, an NVP can comprise an amino acid sequence according to Formula (I): X$_1$-T-K-P-C-Q-S-D-K-D-C-K-K-F-A-C-R-K-P-K-V-P-K-C-I-N-G-F-C-K-C-V-R, wherein X$_1$ represents the amino acid added to the N-terminus, wherein X$_1$ is V, L, I, M, F, W, P, S, T, Y, N, Q, D, E, K, R, or H.

"Native" refers to items found in nature in their natural, unmodified state.

"Natural amino acid" refers to one of the 20 amino acids typically found in proteins in nature, and used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

"Non-natural amino acid" refers to an organic compound that is not among those amino acids encoded by the standard genetic code, or incorporated into proteins during translation. Therefore, non-natural amino acids include amino acids or analogs of amino acids, but are not limited to, the D-isostereomers of amino acids, the beta-amino-analogs of amino acids ($\beta$-amino acids, $\beta^3$ and $\beta^2$), citrulline, homocitrulline, homoarginine, hydroxyproline, homoproline, ornithine, 4-amino-phenylalanine, cyclohexylalanine, $\alpha$-aminoisobutyric acid, N-methyl-alanine, N-methyl-glycine, norleucine, N-methyl-glutamic acid, tert-butylglycine, $\alpha$-aminobutyric acid, tert-butylalanine, 2-aminoisobutyric acid, $\alpha$-aminoisobutyric acid, 2-aminoindane-2-carboxylic acid, selenomethionine, dehydroalanine, lanthionine, $\gamma$-amino butyric acid, and derivatives thereof wherein the amine nitrogen has been mono- or di-alkylated. Exemplary non-natural amino acids are described in Travis S. Young and Peter G. Schultz, "Beyond the Canonical 20 Amino Acids: Expanding the Genetic Lexicon," J. Biol. Chem. 2010 285:11039-11044, which is incorporated by reference herein in its entirety.

"NCBI" refers to the National Center for Biotechnology Information.

"NCR" refers to nodule-specific cysteine-rich.

"NVP" or "NCR13 variant peptide" refers to peptides having antimicrobial activity against one or more microbes, said NVP comprising an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof. For example, and without limitation, in some embodiments, an NVP of the present disclosure comprises a recombinant peptide having an amino acid sequence that is at least 95%, 96%, 97%, 97%, 98%, 99% or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein $X_1$ represents the amino acid added to the N-terminus, wherein $X_1$ is an amino acid V, L, I, M, F, W, P, S, T, Y, N, Q, D, E, K, R, or H; and wherein $X_1$ is not G or A. In yet other embodiments, an NVP can comprise a peptide having an amino sequence that is at least 95%, 96%, 97%, 97%, 98%, 99% or 100% identical to an amino acid sequence as set forth in any one of SEQ ID NOs: 4-19, or 66. In addition, an "NCR13 variant peptide" includes a peptide that comprises, consists essentially of, or consists of an amino acid sequence that is at least 80%, 85%, 90%, 90%, 95%, 96%, 97%, 98%, 99% or 100% identical across the entire length of the peptide to the amino acid sequence as set forth in SEQ ID NO: 1. In some embodiments, an illustrative "NCR13 variant peptide" includes an antimicrobial peptide that has 1, 2, 3, 4, 5, 6, or 7 conservative amino acid substitutions at any amino acid position within the full length sequence as set forth in any one of SEQ ID NOs: 4-19, or 66, wherein the amino acid appended to the N-terminus of WT-NCR13 (SEQ ID NO: 1) is any natural or non-natural amino acid other than glycine or alanine; or an agriculturally acceptable salt thereof.

"NVP expression cassette" refers to one or more regulatory elements such as promoters; enhancer elements; mRNA stabilizing polyadenylation signal; an internal ribosome entry site (IRES); introns; post-transcriptional regulatory elements; and a polynucleotide operable to encode an NVP, e.g., an NVP ORF. For example, one example of an NVP expression cassette is one or more segments of DNA that contains a polynucleotide segment operable to express an NVP, a ADH1 promoter, a LAC4 terminator, and an alpha-MF secretory signal. An NVP expression cassette contains all of the nucleic acids necessary to encode an NVP or an NVP-antimicrobial protein.

"NVP ORF" refers to a polynucleotide operable to encode an NVP, or an NVP-antimicrobial protein.

"NVP ORF diagram" refers to the composition of one or more NVP ORFs, as written out in diagram or equation form. For example, a "NVP ORF diagram" can be written out as using acronyms or short-hand references to the DNA segments contained within the expression ORF. Accordingly, in one example, a "NVP ORF diagram" may describe the polynucleotide segments encoding the ERSP, LINKER, STA, and NVP, by diagramming in equation form the DNA segments as "ersp" (i.e., the polynucleotide sequence that encodes the ERSP polypeptide); "linker" or "L" (i.e., the polynucleotide sequence that encodes the LINKER polypeptide); "sta" (i.e., the polynucleotide sequence that encodes the STA polypeptide), and "nvp" (i.e., the polynucleotide sequence encoding an NVP), respectively. An example of an NVP ORF diagram is "ersp-sta-(linker$_i$-nvp$_j$)$_N$," or "ersp-(nvp$_j$-linker$_i$)$_N$-sta" and/or any combination of the DNA segments thereof.

"NVP-antimicrobial protein" or "NVP-antimicrobial polypeptide" or "antimicrobial protein" or "antimicrobial polypeptide" refers to any protein, peptide, polypeptide, amino acid sequence, configuration, or arrangement, comprising: (1) at least one NVP, or two or more NVPs; and (2) additional peptides, polypeptides, or proteins. For example, in some embodiments, these additional peptides, polypeptides, or proteins have the ability to increase the mortality and/or inhibit the growth of microbes when the microbes are exposed to an NVP-antimicrobial protein, relative to an NVP alone; increase the expression of said NVP-antimicrobial protein, e.g., in a host cell or an expression system; and/or affect the post-translational processing of the NVP-antimicrobial protein. In some embodiments, an NVP-antimicrobial protein can be a polymer comprising two or more NVPs. In some embodiments, an NVP-antimicrobial protein can be a polymer comprising two or more NVPs, wherein the NVPs are operably linked via a linker peptide, e.g., a cleavable and/or non-cleavable linker. In some embodiments, an NVP-antimicrobial protein can refer to a one or more NVPs operably linked with one or more proteins such as a stabilizing domain (STA); an endoplasmic reticulum signaling protein (ERSP); a cleavable or non-cleavable linker (L); and/or any other combination thereof. In some embodiments, an NVP-antimicrobial protein can be a non-naturally occurring protein comprising (1) an NVP; and (2) additional peptides, polypeptides, or proteins, e.g., an ERSP; a linker; a STA; a UBI; or a histidine tag or similar marker.

"NVP construct" refers to the three-dimensional arrangement/orientation of peptides, polypeptides, and/or motifs of operably linked polypeptide segments (e.g., an NVP-antimicrobial protein). For example, an NVP ORF can include one or more of the following components or motifs: an NVP; an endoplasmic reticulum signal peptide (ERSP); a linker peptide (L); a translational stabilizing protein (STA); or any combination thereof. And, as used herein, the term "NVP construct" is used to describe the designation and/or orientation of the structural motif. In other words, the NVP construct describes the arrangement and orientation of the components or motifs contained within a given NVP ORF. For example, in some embodiments, an NVP construct describes, without limitation, the orientation of one of the following NVP-antimicrobial proteins: ERSP-NVP; ERSP-(NVP)$_N$; ERSP-NVP-L; ERSP-(NVP)$_N$-L; ERSP-(NVP-L)$_N$; ERSP-L-NVP; ERSP-L-(NVP)$_N$; ERSP-(L-NVP)$_N$; ERSP-STA-NVP; ERSP-STA-(NVP)$_N$; ERSP-NVP-STA; ERSP-(NVP)$_N$-STA; ERSP-(STA-NVP)$_N$; ERSP-(NVP-STA)$_N$; ERSP-L-NVP-STA; ERSP-L-STA-NVP; ERSP-L-(NVP-STA)$_N$; ERSP-L-(STA-NVP)$_N$; ERSP-L-(NVP)$_N$-STA; ERSP-(L-NVP)$_N$-STA; ERSP-(L-STA-NVP)$_N$; ERSP-(L-NVP-STA)$_N$; ERSP-(L-STA)$_N$-NVP; ERSP-(L-NVP)$_N$-STA; ERSP-STA-L-NVP; ERSP-STA-NVP-L; ERSP-STA-L-(NVP)$_N$; ERSP-(STA-L)$_N$-NVP; ERSP-STA-(L-NVP)$_N$; ERSP-(STA-L-NVP)$_N$; ERSP-STA-(NVP)$_N$-L; ERSP-STA-(NVP-L)$_N$; ERSP-(STA-NVP)$_N$-L; ERSP-(STA-NVP-L)$_N$; ERSP-NVP-L-STA; ERSP-NVP-STA-L; ERSP-(NVP)$_N$-STA-L ERSP-(NVP-L)$_N$-STA; ERSP-(NVP-STA)$_N$-L; ERSP-(NVP-L-STA)$_N$; or ERSP-(NVP-STA-L)$_N$; wherein N is an integer ranging from 1 to 200. See also "Structural motif."

"OD600 nm" or "OD$_{600\ nm}$" refers to optical densities of the liquid sample measured (for example, a microbial cell culture) when measured in a spectrophotometer at 600 nanometers (nm).

"OD660 nm" or "OD$_{660\,nm}$" refers to optical densities of the liquid sample measured (for example, a microbial cell culture) when measured in a spectrophotometer at 660 nanometers (nm).

"One letter code" means the peptide sequence which is listed in its one letter code to distinguish the various amino acids in the primary structure of a protein: alanine=A, arginine=R, asparagine=N, aspartic acid=D, asparagine or aspartic acid=B, cysteine=C, glutamic acid=E, glutamine=Q, glutamine or glutamic acid=Z, glycine=G, histidine=H, isoleucine=I, leucine=L, lysine=K, methionine=M, phenylalanine=F, proline=P, serine=S, threonine=T, tryptophan=W, tyrosine=Y, and valine=V.

"Operable" refers to the ability to be used, the ability to do something, and/or the ability to accomplish some function or result. For example, in some embodiments, "operable" refers to the ability of a polynucleotide, DNA sequence, RNA sequence, or other nucleotide sequence or gene to encode a peptide, polypeptide, and/or protein. For example, in some embodiments, a polynucleotide may be operable to encode a protein, which means that the polynucleotide contains information that imbues it with the ability to create a protein (e.g., by transcribing mRNA, which is in turn translated to protein).

"Pathogenic microbe" refers to any microbe that is deleterious or pathogenic to an organism; e.g., any microbe that causes or exacerbates an infection or disease in a living organism. For example, in some embodiments, a pathogenic microbe can be a pathogen to plants, e.g., a phytopathogen, such as a bacterium, a protozoan, or a fungus; in other embodiments, a pathogenic microbe can be a pathogen to animals. As used herein, a "plant pathogenic microbe" or "plant pathogen" can refer to a microbe that can cause disease into whole plants, plant tissues, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

"Pharmaceutically acceptable salt" is synonymous with agriculturally acceptable salt, and as used herein refers to a compound that is modified by making acid or base salts thereof.

"Plant" shall mean whole plants, plant tissues, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

"Plasmid" refers to a DNA segment that acts as a carrier for a gene of interest (e.g., nvp) and, when transformed or transfected into an organism, can replicate and express the DNA sequence contained within the plasmid independently of the host organism. Plasmids are a type of vector, and can be "cloning vectors" (i.e., simple plasmids used to clone a DNA fragment and/or select a host population carrying the plasmid via some selection indicator) or "expression plasmids" (i.e., plasmids used to produce large amounts of polynucleotides and/or polypeptides).

"Polynucleotide" refers to a polymeric-form of nucleotides (e.g., ribonucleotides, deoxyribonucleotides, or analogs thereof) of any length; e.g., a sequence of two or more ribonucleotides or deoxyribonucleotides. As used herein, the term "polynucleotide" includes double- and single-stranded DNA, as well as double- and single-stranded RNA; it also includes modified and unmodified forms of a polynucleotide (modifications to and of a polynucleotide, for example, can include methylation, phosphorylation, and/or capping). In some embodiments, a polynucleotide can be one of the following: a gene or gene fragment (for example, a probe, primer, EST, or SAGE tag); genomic DNA; genomic DNA fragment; exon; intron; messenger RNA (mRNA); transfer RNA; ribosomal RNA; ribozyme; cDNA; recombinant polynucleotide; branched polynucleotide; plasmid; vector; isolated DNA of any sequence; isolated RNA of any sequence; nucleic acid probe; primer or amplified copy of any of the foregoing.

In yet other embodiments, a polynucleotide can refer to a polymeric-form of nucleotides operable to encode the open reading frame of a gene.

In some embodiments, a polynucleotide can refer to cDNA.

In some embodiments, polynucleotides can have any three-dimensional structure and may perform any function, known or unknown. The structure of a polynucleotide can also be referenced to by its 5'- or 3'-end or terminus, which indicates the directionality of the polynucleotide. Adjacent nucleotides in a single-strand of polynucleotides are typically joined by a phosphodiester bond between their 3' and 5' carbons. However, different internucleotide linkages could also be used, such as linkages that include a methylene, phosphoramidate linkages, etc. This means that the respective 5' and 3' carbons can be exposed at either end of the polynucleotide, which may be called the 5' and 3' ends or termini. The 5' and 3' ends can also be called the phosphoryl ($PO_4$) and hydroxyl (OH) ends, respectively, because of the chemical groups attached to those ends. The term polynucleotide also refers to both double- and single-stranded molecules. Unless otherwise specified or required, any embodiment that makes or uses a polynucleotide encompasses both the double-stranded form and each of two complementary single-stranded forms known or predicted to make up the double-stranded form.

In some embodiments, a polynucleotide can include modified nucleotides, such as methylated nucleotides and nucleotide analogs (including nucleotides with non-natural bases, nucleotides with modified natural bases such as aza- or deaza-purines, etc.). If present, modifications to the nucleotide structure can be imparted before or after assembly of the polynucleotide.

In some embodiments, a polynucleotide can also be further modified after polymerization, such as by conjugation with a labeling component. Additionally, the sequence of nucleotides in a polynucleotide can be interrupted by non-nucleotide components. One or more ends of the polynucleotide can be protected or otherwise modified to prevent that end from interacting in a particular way (e.g. forming a covalent bond) with other polynucleotides.

In some embodiments, a polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term "sequence" refers to the alphabetical representation of a polynucleotide or any nucleic acid molecule, including natural and non-natural bases.

The term "RNA molecule" or ribonucleic acid molecule refers to a polynucleotide having a ribose sugar rather than deoxyribose sugar and typically uracil rather than thymine as one of the pyrimidine bases. An RNA molecule of the disclosure is generally single-stranded, but can also be double-stranded. In the context of an RNA molecule from an RNA sample, the RNA molecule can include the single-stranded molecules transcribed from DNA in the cell nucleus, mitochondrion or chloroplast, which have a linear sequence of nucleotide bases that is complementary to the DNA strand from which it is transcribed.

In some embodiments, a polynucleotide can further comprise one or more heterologous regulatory elements. For example, in some embodiments, the regulatory element is one or more promoters; enhancers; silencers; operators; splicing signals; polyadenylation signals; termination signals; RNA export elements, internal ribosomal entry sites (IRES); poly-U sequences; or combinations thereof.

"ppm" refers to parts per million. As used herein, 1 ppm=1 µg per gram, or 1 ppm=0.0001% w/w (1% w/w=10, 000 ppm).

"Protein" has the same meaning as "peptide" and/or "polypeptide" in this document.

"Ratio" refers to the quantitative relation between two amounts showing the number of times one value contains or is contained within the other.

"Recombinant DNA" or "rDNA" refers to DNA that is comprised of two or more different DNA segments.

"sp." refers to species.

"ssp." or "subsp." refers to subspecies.

"Stringent hybridization" or "stringent hybridization conditions" refers to conditions under which a polynucleotide (e.g., a nucleic acid probe, primer or oligonucleotide) will hybridize to its target sequence, typically in a complex mixture of nucleic acids, but not to other sequences. Stringent hybridization conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide. In some embodiments, a polynucleotide of the present disclosure can stringently hybridize to a polynucleotide encoding an NVP, or a complementary nucleotide sequence thereof. For example, in some embodiments, a polynucleotide of the present disclosure can stringently hybridize to a polynucleotide operable to encode an NVP having an amino acid sequence as set forth in any one of SEQ ID NOs: 4-19, or 66, or a complementary nucleotide sequence thereof.

"Susceptible to attack by a microbe (or microbes)" or "susceptible to a microbial infection" or "susceptible to microbial disease" and the like, refer to plants, or human or animal patients or subjects, susceptible to a microbe pathogen or microbial infections.

"Treatment" or "treating" or "treatment of" or "combatting" or "controlling" or "inhibiting" a pathogenic microbe; or a condition, disease, or disorder in a plant or animal susceptible to an attack by the microbe that is caused by a pathogenic microbe; or symptoms associated with a condition, disease, or disorder in a plant or animal susceptible to an attack by the microbe that is caused by a pathogenic microbe, refers to an approach for obtaining beneficial or desired results in the plant or animal susceptible to an attack by the microbe. Beneficial or desired results can include, but are not limited to, death of at least one microbe; alleviation or amelioration of one or more symptoms or conditions caused by a pathogenic microbe; diminishment of extent of condition, disorder or disease caused by a pathogenic microbe; stabilization of the state of condition, disorder or disease caused by a pathogenic microbe; prevention of development of condition, disorder or disease caused by a pathogenic microbe; prevention of spread of condition, disorder or disease caused by a pathogenic microbe; delay or slowing of condition, disorder or disease progression, delay or slowing of condition, disorder or disease onset caused by a pathogenic microbe; amelioration or palliation of the condition, disorder or disease state, and remission of a disease or disease state caused by a pathogenic microbe; whether partial or total. In some embodiments, "treating" can also mean prolonging survival of an organism beyond that expected in the absence of treatment. "Treating" can also mean inhibiting the progression of the disease or disorder, slowing the progression of disorder or disease temporarily, although in some instances, it involves halting the progression of the disorder or disease permanently. As used herein the terms treatment, treat, or treating refers to a method of reducing the effects of one or more symptoms of a disease or condition caused by a pathogenic microbe. Thus, in some embodiments, treatment can refer to a 1%, 2%, 3%, 4%, 5%, 6%, 7%, 8%, 9% 10%, 20%, 30%, 40%, 50%, 60%, 70%, 80%, 90%, or 100% reduction in the number of pathogenic microbes, and/or the severity of an established disease, condition, or symptom of the disease or condition caused by a pathogenic microbe. It is understood that treatment does not necessarily refer to the death of all pathogenic microbes and/or the cure or complete ablation of the disease, condition, or symptoms of the disease or condition caused by a pathogenic microbe.

"var." refers to varietas or variety. The term "var." is used to indicate a taxonomic category that ranks below the species level and/or subspecies (where present). In some embodiments, the term "var." represents members differing from others of the same subspecies or species in minor but permanent or heritable characteristics.

"Vector" refers to the DNA segment that accepts a foreign gene of interest (e.g., nvp). The gene of interest is known as an "insert" or "transgene."

"Wild type" or "WT" refers to the phenotype and/or genotype (i.e., the appearance or sequence) of an organism, polynucleotide sequence, and/or polypeptide sequence, as it is found and/or observed in its naturally occurring state or condition.

"Wild-type NCR13" or "WT-NCR13" or "WT NCR13" or "NCR13 peptide" or "NCR13" refers to a wild-type nodule-specific cysteine-rich 13 (NCR13) peptide. An exemplary NCR13 peptide is proved herein, having an amino acid sequence (designated as single letter amino acid sequence) consisting of: TKPCQSDKDCKK-FACRKPKVPKCINGFCKCVR (SEQ ID NO: 1) (NCBI Accession No. DAA64987).

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or group of compositions of matter.

The present disclosure is performed without undue experimentation using, unless otherwise indicated, conventional techniques of molecular biology, microbiology, virology, recombinant DNA technology, solid phase and liquid nucleic acid synthesis, peptide synthesis in solution, solid phase peptide synthesis, immunology, cell culture, and formulation. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), TRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, 3. eds.), vol. 2, pp. 1-284, Academic Press, New York. 12. Wiinsch, E., ed. (1974) Synthese von Peptiden in Houben-Weyls Metoden der Organischen Chemie (Muler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000); each of these references are incorporated herein by reference in their entireties.

Throughout this specification, unless the context requires otherwise, the word "comprise," or variations such as "comprises" or "comprising," will be understood to imply the inclusion of a stated step or element or integer or group of steps or elements or integers but not the exclusion of any other step or element or integer or group of elements or integers.

All patent applications, patents, and printed publications referred to herein are incorporated by reference in their entirety to the same extent as if each individual publication, patent, or patent application was specifically and individually indicated to be incorporated by reference in its entirety. All patent applications, patents, and printed publications cited herein are incorporated herein by reference in the entireties, except for any definitions, subject matter disclaimers, or disavowals, and except to the extent that the incorporated material is inconsistent with the express disclosure herein, in which case the language in this disclosure controls.

NCR13 Variant Peptides (NVPs)

Biological antimicrobial agents, e.g., antimicrobial agents based on, or derived from, natural sources (such as an organism or product therefrom), may confer crop protection by suppressing disease incidence, and/or reducing the number of pathogenic microbes or the severity of symptoms caused by the same. Thus, biological antimicrobial agents represent a desirable replacement of traditional agrochemicals, and can be used to avoid or remediate the adverse effects thereof.

Legume plants employ a symbiotic relationship with soil rhizobia that allows these plants to take up biologically usable nitrogen, which is fixed by the bacteria in exchange for nutrients and carbon resources. Endosymbiotic rhizobia induce changes in the host plant, which results in the formation of a specialized root organ called a nodule. See Roy et al., *Symbiotic Outcome Modified by the Diversification from 7 to over 700 Nodule-Specific Cysteine-Rich Peptides*. GENES (BASEL). 2020 April; 11(4): 348. Within nodules, the rhizobia undergo distinct morphological and metabolic changes, and differentiate into nitrogen-fixing bacteroids. Id. Bacteroid differentiation and activity is regulated by a group of peptides called nodule-specific cysteine-rich (NCR) peptides. See Mergaert et al., *Gene Expression in Nitrogen-Fixing Symbiotic Nodule Cells in Medicago truncatula and Other Nodulating Plants*. PLANT CELL. 2020 January; 32(1): 42-68; Kereszt et al., *Impact of Plant Peptides on Symbiotic Nodule Development and Functioning*. FRONT PLANT SCI. 2018; 9: 1026.

Members of the NCR peptide gene family have been identified in legumes including, but not limited to, *Vicia faba, Medicago sativa, Trifolium repens, Galega orientalis, Pisum sativum, Astragalus sinicus, Cicer arietinum* and *Glycyrrhiza lepidota*.

NCR peptides have a structure that resembles antimicrobial defensin peptides, which are effectors of innate immunity in plants and animals, including humans. See Kereszt et al., *Impact of Plant Peptides on Symbiotic Nodule Development and Functioning*. FRONT PLANT SCI. 2018; 9: 1026. And, NCRs have been shown to exhibit antimicrobial activity, e.g., against gram-negative and gram-positive bacteria as well as unicellular and filamentous fungi. See Maróti and Kondorosi, *Nitrogen-fixing Rhizobium-legume symbiosis: are polyploidy and host peptide-governed symbiont differentiation general principles of endosymbiosis?* FRONT MICROBIOL. 2014; 5: 326; Maróti et al., *Natural roles of antimicrobial peptides in microbes, plants and animals*. RES MICROBIOL. 2011 May; 162(4):363-74.

The present disclosure provides an engineered, non-naturally occurring antimicrobial peptides called "NCR13 variant peptides (NVPs)", agriculturally acceptable salts thereof; agricultural compositions thereof, further comprising an excipient; and methods of making and using the same.

Exemplary NVPs

In some embodiments, an antimicrobial NCR13 variant peptide (NVP) can be a recombinant peptide having antimicrobial activity against one or more microbes, or an agriculturally acceptable salt thereof, wherein the NVP comprises at least one mutation comprising an N-terminus addition of an amino acid to a WT-NCR13 amino acid sequence as set forth in SEQ ID NO: 1, wherein the amino acid added to the N-terminus can be any natural or non-natural amino acid other than glycine or alanine.

In some embodiments, an antimicrobial NCR13 variant peptide (NVP) can be a recombinant peptide having antimicrobial activity against one or more microbes, or an agriculturally acceptable salt thereof, wherein the NVP comprises an N-terminus addition of an amino acid to a WT-NCR13 amino acid sequence as set forth in Formula (I): $X_1$-T-K-P-C-Q-S-D-K-D-C-K-K-F-A-C-R-K-P-K-V-P-K-C-I-N-G-F-C-K-C-V-R, wherein $X_1$ represents the amino acid added to the N-terminus of SEQ ID NO: 1, wherein $X_1$ is any natural or non-natural amino acid other than glycine or alanine; or an agriculturally acceptable salt thereof.

In some embodiments, an NVP can be a mutant or variant that differs from a WT-NCR13 (SEQ ID NO: 1), wherein the resulting NVP comprises at least one mutation comprising an N-terminus addition of an amino acid to a WT-NCR13 amino acid sequence as set forth in SEQ ID NO: 1, wherein the amino acid added to the N-terminus can be any natural or non-natural amino acid other than glycine or alanine. In addition, an "NCR13 variant peptide" includes a peptide that comprises, consists essentially of, or consists of, an amino acid sequence that is at least 80%, 85%, 90%, 90%, 95%, 96%, 97%, 98%, 99% or 100% identical across the entire length of the peptide to the amino acid sequence of WT-NCR13 as set forth in SEQ ID NO: 1, and comprises at least one mutation comprising an N-terminus addition of an amino acid to a WT-NCR13 amino acid sequence as set forth in SEQ ID NO: 1, wherein the amino acid added to the N-terminus can be any natural or non-natural amino acid other than glycine or alanine. In some embodiments, an illustrative "NCR13 variant peptide" includes an antimicrobial peptide that has 1, 2, 3, 4, 5, 6, or 7 conservative amino acid substitutions at any amino acid position within the full length sequence as set forth in any one of the amino acid sequences set forth in SEQ ID NOs: 4-19, or 66, or an agriculturally acceptable salt thereof, wherein the amino acid added to the N-terminus can be any natural or non-natural amino acid other than glycine or alanine.

A summary of the NVPs evaluated here possessing mutations that confer novel and unexpected properties relative to WT-NCR13 are provided in the tables below.

least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in the foregoing Table 1, wherein the amino acid added to the N-terminus can be any natural or non-natural amino acid other than glycine or alanine.

In some embodiments, an NCR13 variant peptide (NVP) of the present disclosure comprises, consists essentially of, or consists of, an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at

TABLE 1

Summary of NVPs possessing mutations that confer novel and unexpected properties relative to WT-NCR13. Table 1 provides a summary of NVPs that confer at least one novel property relative to WT-NCR13.

| SEQ ID NO | Name | N-terminus addition | Sequence |
| --- | --- | --- | --- |
| 4 | NCR13M2 | V | VTKPCQSDKDCKKFACRKPKVPKCINGFCKCVR |
| 5 | NCR13M3 | L | LTKPCQSDKDCKKFACRKPKVPKCINGFCKCVR |
| 6 | NCR13M4 | I | ITKPCQSDKDCKKFACRKPKVPKCINGFCKCVR |
| 7 | NCR13M5 | M | MTKPCQSDKDCKKFACRKPKVPKCINGFCKCVR |
| 8 | NCR13M6 | F | FTKPCQSDKDCKKFACRKPKVPKCINGFCKCVR |
| 9 | NCR13M7 | W | WTKPCQSDKDCKKFACRKPKVPKCINGFCKCVR |
| 10 | NCR13M8 | P | PTKPCQSDKDCKKFACRKPKVPKCINGFCKCVR |
| 11 | NCR13M9 | S | STKPCQSDKDCKKFACRKPKVPKCINGFCKCVR |
| 12 | NCR13M10 | T | TTKPCQSDKDCKKFACRKPKVPKCINGFCKCVR |
| 13 | NCR13M11 | Y | YTKPCQSDKDCKKFACRKPKVPKCINGFCKCVR |
| 14 | NCR13M12 | N | NTKPCQSDKDCKKFACRKPKVPKCINGFCKCVR |
| 15 | NCR13M13 | Q | QTKPCQSDKDCKKFACRKPKVPKCINGFCKCVR |
| 16 | NCR13M14 | D | DTKPCQSDKDCKKFACRKPKVPKCINGFCKCVR |
| 17 | NCR13M15 | E | ETKPCQSDKDCKKFACRKPKVPKCINGFCKCVR |
| 18 | NCR13M16 | K | KTKPCQSDKDCKKFACRKPKVPKCINGFCKCVR |
| 19 | NCR13M17 | H | HTKPCQSDKDCKKFACRKPKVPKCINGFCKCVR |
| 66 | NCR13M18 | R | RTKPCQSDKDCKKFACRKPKVPKCINGFCKCVR |

In some embodiments, an NCR13 variant peptide (NVP) of the present disclosure comprises, consists essentially of, or consists of, an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof.

In some embodiments, an NCR13 variant peptide (NVP) having antimicrobial activity against one or more microbe species, comprises, consists essentially of, or consists of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or an agriculturally acceptable salt thereof.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is a natural amino acid.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is V, L, I, M, F, W, P, S, T, Y, N, Q, D, E, K, R, or H.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L, M, F, W, S, Y, D, or E.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L or W.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises at least one mutation relative to a WT-NCR13 amino acid sequence as set forth in SEQ ID NO: 1; wherein $X_1$ is an amino acid addition to the N-terminus of the WT-NCR13 amino acid sequence; and wherein $X_1$ is any natural or non-natural amino acid other than glycine or alanine.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein $X_1$ is an N-terminus addition of an amino acid to a WT-NCR13 amino acid sequence as set forth in SEQ ID NO: 1; and wherein $X_1$ is any natural or non-natural amino acid other than glycine or alanine.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: V, L, I, M, F, W, P, S, T, Y, N, Q, D, E, K, R, or H; or an agriculturally acceptable salt thereof.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L, M, F, W, S, Y, D, or E; or an agriculturally acceptable salt thereof.

In some embodiments, an NCR13 variant peptide (NVP) of the present disclosure comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L or W; or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "VTKPCQSDKDCKKFACRKPKVPKCINGFCKCVR" (SEQ ID NO: 4), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "LTKPCQSDKDCKKFACRKPKVPKCINGFCKCVR" (SEQ ID NO: 5), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ITKPCQSDKDCKK-FACRKPKVPKCINGFCKCVR" (SEQ ID NO: 6), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "MTKPCQSDKDCKKFACRKPKVPKCINGFCKCVR" (SEQ ID NO: 7), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "FTKPCQSDKDCKKFACRKPKVPKCINGFCKCVR" (SEQ ID NO: 8), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "WTKPCQSDKDCKKFACRKPKVPKCINGFCKCVR" (SEQ ID NO: 9), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "PTKPCQSDKDCKKFACRKPKVPKCINGFCKCVR" (SEQ ID NO: 10), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "STKPCQSDKDCKKFACRKPKVPKCINGFCKCVR" (SEQ ID NO: 11), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "TTKPCQSDKDCKKFACRKPKVPKCINGFCKCVR" (SEQ ID NO: 12), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "YTKPCQSDKDCKKFACRKPKVPKCINGFCKCVR" (SEQ ID NO: 13), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "NTKPCQSDKDCKKFACRKPKVPKCINGFCKCVR" (SEQ ID NO: 14), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "QTKPCQSDKDCKKFACRKPKVPKCINGFCKCVR" (SEQ ID NO: 15), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "DTKPCQSDKDCKKFACRKPKVPKCINGFCKCVR" (SEQ ID NO: 16), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ETKPCQSDKDCKKFACRKPKVPKCINGFCKCVR" (SEQ ID NO: 17), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KTKPCQSDKDCKKFACRKPKVPKCINGFCKCVR" (SEQ ID NO: 18), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "HTKPCQSDKDCKKFACRKPKVPKCINGFCKCVR" (SEQ ID NO: 19), or an agriculturally acceptable salt thereof.

In some embodiments, an NVP of the present disclosure can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "RTKPCQSDKDCKKFACRKPKVPKCINGFCKCVR" (SEQ ID NO: 66), or an agriculturally acceptable salt thereof.

An antimicrobial NCR13 variant peptide (NVP) of the present invention does not have an N-terminus addition of a glycine (e.g., SEQ ID NO: 2) or an alanine (e.g., SEQ ID NO: 3).

In some embodiments, an NVP of the present disclosure can comprise, consist essentially of, or consist of, a homopolymer or heteropolymer of two or more NVPs, wherein the amino acid sequence of each NVP is the same or different.

In some embodiments, an NVP of the present disclosure can comprise, consist essentially of, or consist of, an NVP that is a fused protein comprising two or more NVPs separated by a cleavable or non-cleavable linker, and wherein the amino acid sequence of each NVP may be the same or different.

In some embodiments, the linker is a cleavable linker.

In some embodiments, the linker has an amino acid sequence as set forth in any one of SEQ ID NOs: 39-51.

In some embodiments, the linker is cleavable inside at least one of (i) the gut or hemolymph of an invertebrate, and (ii) cleavable inside the gut of a mammal.

Detailed methods concerning linkers are described below.

Polynucleotides Encoding NVPs

In some embodiments, the present disclosure comprises, consists essentially of, or consists of, a polynucleotide operable to encode an NCR13 variant peptide (NVP).

In some embodiments, a polynucleotide of the present disclosure comprises, consists essentially of, or consists of, a polynucleotide operable to encode an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; wherein the amino acid is V, L, I, M, F, W, P, S, T, Y, N, Q, D, E, K, R, or H; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or wherein the amino acid is L, M, F, W, S, Y, D, or E; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or wherein the amino acid is L or W; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: V, L, I, M, F, W, P, S, T, Y, N, Q, D, E, K, R, or H; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L, M, F, W, S, Y, D, or E; or a complementary nucleotide sequence thereof.

In some embodiments, a polynucleotide of the present disclosure comprises, consists essentially of, or consists of, a polynucleotide operable to encode an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L or W; or a complementary nucleotide sequence thereof.

In some embodiments, a polynucleotide of the present disclosure comprises, consists essentially of, or consists of, a polynucleotide operable to encode an NVP that can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "VTKPCQSDKDCKK-FACRKPKVPKCINGFCKCVR" (SEQ ID NO: 4), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "LTKPCQSDKDCKK-FACRKPKVPKCINGFCKCVR" (SEQ ID NO: 5), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ITKPCQSDKDCKK-FACRKPKVPKCINGFCKCVR" (SEQ ID NO: 6), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "MTKPCQSDKDCKK-FACRKPKVPKCINGFCKCVR" (SEQ ID NO: 7), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "FTKPCQSDKDCKK-FACRKPKVPKCINGFCKCVR" (SEQ ID NO: 8), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "WTKPCQSDKDCKK-FACRKPKVPKCINGFCKCVR" (SEQ ID NO: 9), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "PTKPCQSDKDCKK-FACRKPKVPKCINGFCKCVR" (SEQ ID NO: 10), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "STKPCQSDKDCKK-FACRKPKVPKCINGFCKCVR" (SEQ ID NO: 11), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "TTKPCQSDKDCKK-FACRKPKVPKCINGFCKCVR" (SEQ ID NO: 12), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "YTKPCQSDKDCKK-FACRKPKVPKCINGFCKCVR" (SEQ ID NO: 13), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "NTKPCQSDKDCKK-FACRKPKVPKCINGFCKCVR" (SEQ ID NO: 14), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "QTKPCQSDKDCKK-FACRKPKVPKCINGFCKCVR" (SEQ ID NO: 15), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "DTKPCQSDKDCKK-FACRKPKVPKCINGFCKCVR" (SEQ ID NO: 16), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ETKPCQSDKDCKK- FACRKPKVPKCINGFCKCVR" (SEQ ID NO: 17), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KTKPCQSDKDCKK-FACRKPKVPKCINGFCKCVR" (SEQ ID NO: 18), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "HTKPCQSDKDCKK-FACRKPKVPKCINGFCKCVR" (SEQ ID NO: 19), or a complementary nucleotide sequence thereof.

In some embodiments, a polynucleotide of the present disclosure is operable to encode an NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "RTKPCQSDKDCKK-FACRKPKVPKCINGFCKCVR" (SEQ ID NO: 66), or a complementary nucleotide sequence thereof.

In some embodiments, the polynucleotide comprises, consists essentially of, or consists of, a nucleotide sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the nucleotide sequence set forth in any one of SEQ ID NOs: 23-38, or a complementary nucleotide sequence thereof.

In some embodiments, the polynucleotide comprises, consists essentially of, or consists of, a nucleotide sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the nucleotide sequence set forth in any one of SEQ ID NOs: 24, 26, 27, 28, 30, 32, 35, and 36, or a complementary nucleotide sequence thereof.

In some embodiments, the polynucleotide is operable to encode an NVP that can comprise, consist essentially of, or consist of, a homopolymer or heteropolymer of two or more NVPs, wherein the amino acid sequence of each NVP is the same or different.

In some embodiments, the polynucleotide is operable to encode an NVP that can comprise, consist essentially of, or consist of, an NVP that is a fused protein comprising two or more NVPs separated by a cleavable or non-cleavable linker, and wherein the amino acid sequence of each NVP may be the same or different.

In some embodiments, the linker is a cleavable linker.

In some embodiments, the linker has an amino acid sequence as set forth in any one of SEQ ID NOs: 39-51.

In some embodiments, the linker is cleavable inside at least one of (i) the gut or hemolymph of an invertebrate, and (ii) cleavable inside the gut of a mammal.

NVP-Antimicrobial Proteins

In some embodiments, an NVP-antimicrobial protein can be any protein, peptide, polypeptide, amino acid sequence, configuration, construct, or arrangement, comprising: (1) at least one NVP, or two or more NVPs; and (2) one or more additional non-NVP peptides, polypeptides, or proteins. For example, in some embodiments, these additional non-NVP peptides, polypeptides, or proteins may have the ability to increase the mortality and/or inhibit the growth of microbes exposed to the NVP-antimicrobial protein, relative to the NVP alone; increase the expression of the NVP-antimicrobial protein, e.g., in a host cell; and/or affect the post-translational processing of the NVP-antimicrobial protein.

In some embodiments, an NVP-antimicrobial protein can be a polymer comprising two or more NVPs. In yet other embodiments, an NVP-antimicrobial protein can be a polymer comprising two or more NVPs, wherein the NVPs are operably linked via a linker peptide, e.g., a cleavable and/or a non-cleavable linker. Here, the linker peptide falls under the category of the additional non-NVP peptide described above.

In some embodiments, an NVP-antimicrobial protein can refer to a one or more NVPs operably linked with one or more proteins such as a stabilizing domain (STA); an endoplasmic reticulum signaling protein (ERSP); an microbe cleavable or microbe non-cleavable linker (L); and/or any other combination thereof.

In some embodiments, an NVP-antimicrobial protein can be a polymer of amino acids that, when properly folded or in its most natural thermodynamic state, exerts an antimicrobial activity against one or more microbes.

In some embodiments, an NVP-antimicrobial protein can be a polymer comprising two or more NVPs that are different. In other embodiments, an antimicrobial protein can be a polymer of two or more NVPs that are the same.

In yet other embodiments, an NVP-antimicrobial protein can comprise one or more NVPs, and one or more peptides, polypeptides, or proteins, that may assist in the NVP-antimicrobial protein's folding.

In some embodiments, an NVP-antimicrobial protein can comprise one or more NVPs, and one or more peptides, polypeptides, or proteins, wherein the one or more peptides, polypeptides, or proteins are protein tags that help stability or solubility. In other embodiments, the peptides, polypeptides, or proteins can be protein tags that aid in affinity purification.

In some embodiments, an NVP-antimicrobial protein can refer to a one or more NVPs operably linked with one or more proteins such as a stabilizing domain (STA); an endoplasmic reticulum signaling protein (ERSP); an microbe cleavable or microbe non-cleavable linker; one or more heterologous peptides; one or more additional polypeptides; and/or any other combination thereof. In some embodiments, an antimicrobial protein can comprise a one or more NVPs as disclosed herein.

In some embodiments, an NVP-antimicrobial protein can comprise an NVP homopolymer, e.g., two or more NVP monomers that are the same NVP. In some embodiments, the antimicrobial protein can comprise an NVP heteropolymer, e.g., two or more NVP monomers, wherein the NVP monomers are different.

In some embodiments, an NVP-antimicrobial protein can comprise, consist essentially of, or consist of one or more NVPs having an amino acid sequence set forth in SEQ ID NOs: 4-19, or 66, or an agriculturally acceptable salt thereof.

In some embodiments, an NVP-antimicrobial protein can comprise, consist essentially of, or consist of one or more NVPs having an amino acid sequence set forth in SEQ ID NOs: 5, 7, 8, 9, 11, 13, 16, and 17, or an agriculturally acceptable salt thereof.

In some embodiments, the NVP-antimicrobial protein may comprise an NVP having an amino acid sequence having at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence set forth in SEQ ID NOs: 4-19, or 66, or an agriculturally acceptable salt thereof.

In some embodiments, the NVP-antimicrobial protein may comprise an NVP having an amino acid sequence having at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence set forth in SEQ ID NOs: 5, 7, 8, 9, 11, 13, 16, and 17, or an agriculturally acceptable salt thereof.

Examples of linkers include, but not limited to, the following sequences: IGER (SEQ ID NO: 39), EEKKN, (SEQ ID NO:40), and ETMFKHGL (SEQ ID NO:41), or combinations thereof.

In some embodiments, the linker can be one or more of the following: ALKFLV (SEQ ID NO: 42), ALKLFV (SEQ ID NO: 43), IFVRLR (SEQ ID NO: 44), LFAAPF (SEQ ID NO: 45), ALKFLVGS (SEQ ID NO: 46), ALKLFVGS (SEQ ID NO: 47), IFVRLRGS (SEQ ID NO: 48), LFAAPFGS (SEQ ID NO: 49), LFVRLRGS (SEQ ID NO: 50), and/or LGERGS (SEQ ID NO: 51).

Exemplary methods for the generation of cleavable and non-cleavable linkers can be found in U.S. patent application Ser. No. 15/727,277; and PCT Application No. PCT/US2013/030042, the disclosure of which are incorporated herein by reference in their entireties.

Exemplary ERSPs and STAs and their methods of use are provided in U.S. Pat. No. 9,567,381, the disclosure of which is incorporated herein by reference in its entirety.

Detailed methods concerning ERSPs, STAs, and linkers, are described below.

Methods for Producing Antimicrobial Peptides

In some illustrative embodiments, the NVP, or an agriculturally acceptable salt thereof of the present disclosure can be produced and/or obtained via any method well known in the art of peptide synthesis.

Recombinant Antimicrobial Peptides

In some embodiments, the engineered, non-naturally occurring antimicrobial peptide of the present disclosure can be produced using recombinant methods.

In some embodiments, an engineered, non-naturally occurring antimicrobial peptide of the present disclosure can be created using any known method for producing a peptide or protein. For example, in some embodiments, and without limitation, an engineered, non-naturally occurring antimicrobial peptide of the present disclosure can be created using a recombinant expression system, such as yeast expression system or a bacterial expression system. However, those having ordinary skill in the art will recognize that other methods of protein production are available.

In some embodiments, an NVP of the present disclosure can be produced using a recombinant expression system.

The recombinant expression of an NVP of the present disclosure is practicable in a wide variety of host cells. In some embodiments, the host cell can be any host cell that satisfies the requirements of the end-user. For example, in some embodiments, a user may desire to use one specific type of host cell (e.g., a yeast cell or a bacteria cell) as opposed to another; the preference of a given host cell can range from desired codon usage, availability and cost, among other considerations.

In some embodiments, a polynucleotide operable to encode an NVP of the present disclosure as provided in Table 1 can be cloned into a vector using a variety of cloning strategies, and commercial cloning kits and materials readily available to those having ordinary skill in the art. For example, a polynucleotide which encodes the NVP can be cloned into a vector using such strategies as the SnapFast; Gateway; TOPO; Gibson; LIC; InFusionHD; or Electra strategies. There are numerous commercially available vectors that can be used to produce an NVP, or an agriculturally acceptable salt thereof of the present disclosure. See Janke et al., A versatile toolbox for PCR-based tagging of yeast genes: new fluorescent proteins, more markers and promoter substitution cassettes. Yeast. 2004 August; 21(11):947-62; see also, Adams et al. Methods in Yeast Genetics. Cold Spring Harbor, N.Y., 1997, the disclosures of which are incorporated herein by reference in its entireties.

In some embodiments, a polynucleotide encoding an NVP of the present disclosure can be cloned into a vector such as a plasmid, cosmid, virus (bacteriophage, animal viruses, and plant viruses), and/or artificial chromosome (e.g., YACs).

In some embodiments, a polynucleotide encoding an NVP of the present disclosure can be inserted into other commercially available plasmids and/or vectors that are readily available to those having skill in the art, e.g., plasmids are available from Addgene (a non-profit plasmid repository); GenScript®; Takara®; Qiagen®; and Promega™.

Additional exemplary methods of producing recombinant peptides are provided in PCT Application Nos. PCT/US2013/030042, PCT/US2017/055596, PCT/US2019/051093, PCT/US2021/028254, PCT/US2021/030277, the disclosures of which is incorporated herein by reference in their entireties.

Chemically Synthesizing Polynucleotides

In some embodiments, the polynucleotide sequence encoding an NVP of the present disclosure can be chemically synthesized using commercially available polynucleotide synthesis services, such as those offered by GENEWIZ® (e.g., TurboGENE™; PriorityGENE; and FragmentGENE), or SIGMA-ALDRICH® (e.g., Custom DNA and RNA Oligos Design and Order Custom DNA Oligos). Exemplary method for generating DNA and or custom chemically synthesized polynucleotides are well known in the art, and are illustratively provided in U.S. Pat. No. 5,736,135, Ser. No. 08/389,615, filed on Feb. 13, 1995, the disclosure of which is incorporated herein by reference in its entirety. See also Agarwal, et al., Chemical synthesis of polynucleotides. Angew Chem Int Ed Engl. 1972 June; 11(6):451-9; Ohtsuka et al., Recent developments in the chemical synthesis of polynucleotides. Nucleic Acids Res. 1982 Nov. 11; 10(21): 6553-6570; Sondek & Shortle. A general strategy for random insertion and substitution mutagenesis: substoichiometric coupling of trinucleotide phosphoramidites. Proc Natl Acad Sci USA. 1992 Apr. 15; 89(8): 3581-3585; Beaucage S. L., et al., Advances in the Synthesis of Oligonucleotides by the Phosphoramidite Approach. Tetrahedron, Elsevier Science Publishers, Amsterdam, NL, vol. 48, No. 12, 1992, pp. 2223-2311; Agrawal (1993) Protocols for Oligonucleotides and Analogs: Synthesis and Properties; Methods in Molecular Biology Vol. 20, the disclosures of which are incorporated herein by reference in their entirety.

Chemically synthesizing polynucleotides allows for a DNA sequence to be generated that is tailored to produce a desired peptide based on the arrangement of nucleotides within said sequence (i.e., the arrangement of cytosine [C], guanine [G], adenine [A] or thymine [T] molecules); the mRNA sequence that is transcribed from the chemically synthesized DNA polynucleotide can be translated to a sequence of amino acids, each amino acid corresponding to a codon in the mRNA sequence.

Obtaining an NVP of the present disclosure from a chemically synthesized DNA polynucleotide sequence and/or a wild-type DNA polynucleotide sequence can be achieved by cloning the DNA sequence into an appropriate vector. There are a variety of expression vectors available, host organisms, and cloning strategies known to those having ordinary skill in the art. For example, the vector can be a plasmid, which can introduce a heterologous gene and/or expression cassette into yeast cells to be transcribed and translated. The term "vector" is used to refer to a carrier nucleic acid molecule into which a nucleic acid sequence can be inserted for introduction into a cell where it can be replicated. A vector may contain "vector elements" such as an origin of replication (ORI); a gene that confers antibiotic resistance to allow for selection; multiple cloning sites; a promoter region; a selection marker for non-bacterial transfection; and a primer binding site. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. In addition to synthesizing a polynucleotide operable to encode an NVP of the present disclosure, a vector may also encode a targeting molecule. A targeting molecule is one that directs the desired nucleic acid to a particular tissue, cell, or other location.

Chemically Synthesizing Peptides

Peptide synthesis or the chemical synthesis of peptides and/or polypeptides can be used to produce or synthesize an NVP of the present disclosure. These methods can be performed by those having ordinary skill in the art, and/or through the use of commercial vendors (e.g., GenScript®; Piscataway, N.J.). For example, in some embodiments, chemical peptide synthesis can be achieved using Liquid phase peptide synthesis (LPPS), or solid phase peptide synthesis (SPPS).

In some embodiments, peptide synthesis can generally be achieved by using a strategy wherein the coupling the carboxyl group of a subsequent amino acid to the N-terminus of a preceding amino acid generates the nascent polypeptide chain—a process that is opposite to the type of polypeptide synthesis that occurs in nature.

Peptide deprotection is an important first step in the chemical synthesis of polypeptides. Peptide deprotection is the process in which the reactive groups of amino acids are blocked through the use of chemicals in order to prevent said amino acid's functional group from taking part in an unwanted or non-specific reaction or side reaction; in other words, the amino acids are "protected" from taking part in these undesirable reactions.

Prior to synthesizing the peptide chain, the amino acids must be "deprotected" to allow the chain to form (i.e., amino acids to bind). Chemicals used to protect the N-termini include 9-fluorenylmethoxycarbonyl (Fmoc), and tert-butoxycarbonyl (Boc), each of which can be removed via the use of a mild base (e.g., piperidine) and a moderately strong acid (e.g., trifluoroacetic acid (TFA)), respectively.

The C-terminus protectant required is dependent on the type of chemical peptide synthesis strategy used: e.g., LPPS requires protection of the C-terminal amino acid, whereas SPPS does not owing to the solid support which acts as the protecting group. Side chain amino acids require the use of several different protecting groups that vary based on the individual peptide sequence and N-terminal protection strategy; typically, however, the protecting group used for side chain amino acids are based on the tert-butyl (tBu) or benzyl (Bzl) protecting groups.

Amino acid coupling is the next step in a peptide synthesis procedure. To effectuate amino acid coupling, the incoming amino acid's C-terminal carboxylic acid must be activated: this can be accomplished using carbodiimides such as diisopropylcarbodiimide (DIC), or dicyclohexylcarbodiimide (DCC), which react with the incoming amino acid's carboxyl group to form an O-acylisourea intermediate. The O-acylisourea intermediate is subsequently displaced via nucleophilic attack via the primary amino group on the N-terminus of the growing peptide chain. The reactive intermediate generated by carbodiimides can result in the racemization of amino acids. To avoid racemization of the amino acids, reagents such as 1-hydroxybenzotriazole (HOBt) are added in order to react with the O-acylisourea intermediate. Other couple agents that may be used include 2-(1H-benzotriazol-1-yl)-1,1,3,3-tetramethyluronium hexafluorophosphate (HBTU), and benzotriazol-1-yl-oxy-tris(dimethylamino)phosphonium hexafluorophosphate (BOP), with the additional activating bases. Finally, amino acid deprotection and coupling.

At the end of the synthesis process, removal of the protecting groups from the polypeptide must occur—a process that usually occurs through acidolysis. Determining which reagent is required for peptide cleavage is a function of the protection scheme used and overall synthesis method. For example, in some embodiments, hydrogen bromide (HBr); hydrogen fluoride (HF); or trifluoromethane sulfonic acid (TFMSA) can be used to cleave Bzl and Boc groups. Alternatively, in other embodiments, a less strong acid such as TFA can effectuate acidolysis of tBut and Fmoc groups. Finally, peptides can be purified based on the peptide's physiochemical characteristics (e.g., charge, size, hydrophobicity, etc.). Techniques that can be used to purify peptides include Purification techniques include Reverse-phase chromatography (RPC); Size-exclusion chromatography; Partition chromatography; High-performance liquid chromatography (HPLC); and Ion exchange chromatography (IEC).

Exemplary methods of peptide synthesis can be found in Anderson G. W. and McGregor A. C. (1957) T-butyloxycarbonylamino acids and their use in peptide synthesis. Journal of the American Chemical Society. 79, 6180-3; Carpino L. A. (1957) Oxidative reactions of hydrazines. Iv. Elimination of nitrogen from 1, 1-disubstituted-2-arenesulfonhydrazides1-4. Journal of the American Chemical Society. 79, 4427-31; McKay F. C. and Albertson N. F. (1957) New amine-masking groups for peptide synthesis. Journal of the American Chemical Society. 79, 4686-90; Merrifield R. B. (1963) Solid phase peptide synthesis. I. The synthesis of a tetrapeptide. Journal of the American Chemical Society. 85, 2149-54; Carpino L. A. and Han G. Y. (1972) 9-fluorenylmethoxycarbonyl amino-protecting group. The Journal of Organic Chemistry. 37, 3404-9; and A Lloyd-Williams P. et al. (1997) Chemical approaches to the synthesis of peptides and proteins. Boca Raton: CRC Press. 278; U.S. Pat. No. 3,714,140 (filed Mar. 16, 1971); U.S. Pat. No. 4,411,994 (filed Jun. 8, 1978); U.S. Pat. No. 7,785,832 (filed Jan. 20, 2006); U.S. Pat. No. 8,314,208 (filed Feb. 10, 2006); and U.S. Pat. No. 10,442,834 (filed Oct. 2, 2015); and United States Patent Application 2005/0165215 (filed Dec. 23, 2004), the disclosures of which are incorporated herein by reference in their entireties.

Any of the methods described herein can be used to generate an NVP described herein, e.g., an engineered, non-naturally occurring antimicrobial peptide consisting of an amino acid sequence set forth in any one of SEQ ID NOs: 5, 7, 8, 9, 11, 13, 16, or 17, or encoded by the nucleotide sequence set forth in any one of SEQ ID NOs: 24, 26, 27, 28, 30, 32, 35, or 36.

Cell Culture and Transformation Techniques

The terms "transformation" and "transfection" both describe the process of introducing exogenous and/or heterologous polynucleotide (e.g., DNA or RNA) to a host organism. Generally, those having ordinary skill in the art sometimes reserve the term "transformation" to describe processes where exogenous and/or heterologous polynucleotide (e.g., DNA or RNA) are introduced into a bacterial cell; and reserve the term "transfection" for processes that describe the introduction of exogenous and/or heterologous polynucleotide (e.g., DNA or RNA) into eukaryotic cells. However, as used herein, the term "transformation" and "transfection" are used synonymously, regardless of whether a process describes the introduction exogenous and/or heterologous DNA or RNA into a prokaryote (e.g., bacteria) or a eukaryote (e.g., yeast, plants, or animals).

In some embodiments, a host organism can be transformed with a polynucleotide operable to encode an NVP. In some embodiments, the host organism can be an microorganism, e.g., a cell.

In some embodiments, a vector comprising an NVP expression cassette can be cloned into an expression plasmid and transformed into a host cell. In some embodiments, the host cell can be selected from any host cell described herein.

In some embodiments, a host cell can be transformed using the following methods: electroporation; cell squeezing; microinjection; impalefection; the use of hydrostatic pressure; sonoporation; optical transfection; continuous infusion; lipofection; through the use of viruses such as adenovirus, adeno-associated virus, lentivirus, herpes simplex virus, and retrovirus; the chemical phosphate method; endocytosis via DEAE-dextran or polyethylenimine (PEI); protoplast fusion; hydrodynamic deliver; magnetofection; nucleoinfection; and/or others. Exemplary methods regarding transfection and/or transformation techniques can be found in Makrides (2003), Gene Transfer and Expression in Mammalian Cells, Elvesier; Wong, T K & Neumann, E. Electric field mediated gene transfer. Biochem. Biophys. Res. Commun. 107, 584-587 (1982); Potter & Heller, Transfection by Electroporation. Curr Protoc Mol Biol. 2003 May; CHAPTER: Unit-9.3; Kim & Eberwine, Mammalian cell transfection: the present and the future. Anal Bioanal Chem. 2010 August; 397(8): 3173-3178, each of these references are incorporated herein by reference in their entireties.

Electroporation is an exemplary method for transforming host cells. Electroporation is a technique in which electricity is applied to cells causing the cell membrane to become permeable; this in turn allows exogenous DNA to be introduced into the cells. Electroporation is readily known to those having ordinary skill in the art, and the tools and devices required to achieve electroporation are commercially available (e.g., Gene Pulser Xcell™ Electroporation Systems, Bio-Rad®; Neon® Transfection System for Electroporation, Thermo-Fisher Scientific; and other tools and/or devices). Exemplary methods of electroporation are illustrated in Potter & Heller, Transfection by Electroporation. Curr Protoc Mol Biol. 2003 May; CHAPTER: Unit-9.3;

Saito (2015) Electroporation Methods in Neuroscience. Springer press; Pakhomov et al., (2017) Advanced Electroporation Techniques in Biology and Medicine. Taylor & Francis; the disclosure of which is incorporated herein by reference in its entirety.

In some embodiments, electroporation can be used transform a cell with one or more vectors containing a polynucleotide operable to encode one or more NVPs or NVP-antimicrobial proteins. For example, in some embodiments, electroporation can be used transform a cell with one or more vectors containing one or more NVP expression cassettes.

Exemplary Description of Yeast Transformation and Culture Methods

In some embodiments, electroporation can be used transform a yeast cell with one or more vectors containing one or more NVP expression cassettes, which can produce NVP in a yeast culture with a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of NVP per liter of medium.

In some embodiments, electroporation can be used to introduce a vector containing a polynucleotide encoding an NVP into yeast, for example, in some embodiments, an NVP expression cassette cloned into a plasmid, and transformed into yeast cells via electroporation.

In some embodiments, an NVP expression cassette cloned into a plasmid, and transformed a host cell (e.g., a yeast cell) via electroporation can be accomplished by inoculating about 10-200 mL of yeast extract peptone dextrose (YEPD) with a suitable yeast species, for example, *Kluyveromyces lactis, Kluyveromyces marxianus, Saccharomyces cerevisiae, Pichia pastoris*, etc., and incubate on a shaker at 30° C. until the early exponential phase of yeast culture (e.g. about 0.6 to $2\times10^8$ cells/mL); harvesting the yeast in sterile centrifuge tube and centrifuging at 3000 rpm for 5 minutes at 4° C. (note: keep cells chilled during the procedure) washing cells with 40 mL of ice cold, sterile deionized water, and pelleting the cells a 23,000 rpm for 5 minutes; repeating the wash step, and the resuspending the cells in 20 mL of 1M fermentable sugar, e.g. galactose, maltose, latotriose, sucrose, fructose or glucose and/or sugar alcohol, for example, erythritol, hydrogenated starch hydrolysates, isomalt, lactitol, maltitol, mannitol, and xylitol, followed by spinning down at 3,000 rpm for 5 minutes; resuspending the cells with proper volume of ice cold 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol to final cell density of $3\times10^9$ cell/mL; ($1.5\times10^9$ cell/mL to $6\times10^9$ cell/mL are acceptable cell densities); mixing 40 µl of the yeast suspension with about 1-4 µl (at a concentration of 100-300 ng/µl) of the vector containing a linear polynucleotide encoding an NVP (~1 µg) in a prechilled 0.2 cm electroporation cuvette (note: ensure the sample is in contact with both sides of the aluminum cuvette); providing a single pulse at 2000 V, for optimal time constant of 5 ms of the RC circuit, the cells was then let recovered in 0.5 ml YED and 0.5 mL 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol mixture, and then spreading onto selective plates.

In some embodiments, electroporation can be used to introduce a vector containing a polynucleotide encoding an NVP into yeast, for example, an NVP cloned into a plasmid, and transformed into *K. lactis* cells via electroporation, can be accomplished by inoculating about 10-200 mL of yeast extract peptone dextrose (YEPD) incubating on a shaker at 30° C. until the early exponential phase of yeast culture (e.g. about 0.6 to $2\times10^8$ cells/mL); harvesting the yeast in sterile centrifuge tube and centrifuging at 3000 rpm for 5 minutes at 4° C. (note: keep cells chilled during the procedure) washing cells with 40 mL of ice cold, sterile deionized water, and pelleting the cells a 23,000 rpm for 5 minutes; repeating the wash step, and the resuspending the cells in 20 mL of 1M fermentable sugar, e.g. galactose, maltose, latotriose, sucrose, fructose or glucose and/or sugar alcohol, for example, erythritol, hydrogenated starch hydrolysates, isomalt, lactitol, maltitol, mannitol, and xylitol, followed by spinning down at 3,000 rpm for 5 minutes; resuspending the cells with proper volume of ice cold 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol to final cell density of $3\times10^9$ cell/mL; mixing 40 µl of the yeast suspension with about 1-4 µl of the vector containing a linear polynucleotide encoding an NVP (~1 µg) in a prechilled 0.2 cm electroporation cuvette (note: ensure the sample is in contact with both sides of the aluminum cuvette); providing a single pulse at 2000 V, for optimal time constant of 5 ms of the RC circuit, the cells was then let recovered in 0.5 ml YED and 0.5 mL 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol mixture, and then spreading onto selective plates.

In some embodiments, using the illustrated methods described herein, i.e., vectors of the present disclosure utilizing yeast, and methods transformation and fermentation, may result in production of NVP in amounts of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of NVP per liter of medium.

In some embodiments, electroporation can be used to introduce a vector containing a polynucleotide encoding an NVP into plant protoplasts by incubating sterile plant material in a protoplast solution (e.g., around 8 mL of 10 mM 2-[N-morpholino]ethanesulfonic acid (MES), pH 5.5; 0.01% (w/v) pectylase; 1% (w/v) macerozyme; 40 mM $CaCl_2$); and 0.4 M mannitol) and adding the mixture to a rotary shaker for about 3 to 6 hours at 30° C. to produce protoplasts; removing debris via 80-µm-mesh nylon screen filtration; rinsing the screen with about 4 ml plant electroporation buffer (e.g., 5 mM $CaCl_2$); 0.4 M mannitol; and PBS); combining the protoplasts in a sterile 15 mL conical centrifuge tube, and then centrifuging at about 300×g for about 5 minutes; subsequent to centrifugation, discarding the supernatant and washing with 5 mL of plant electroporation buffer; resuspending the protoplasts in plant electroporation buffer at about $1.5 \times 10^6$ to $2 \times 10^6$ protoplasts per mL of liquid; transferring about 0.5-mL of the protoplast suspension into one or more electroporation cuvettes, set on ice, and adding the vector (note: for stable transformation, the vector should be linearized using anyone of the restriction methods described above, and about 1 to 10 µg of vector may be used; for transient expression, the vector may be retained in its supercoiled state, and about 10 to 40 µg of vector may be used); mixing the vector and protoplast suspension; placing the cuvette into the electroporation apparatus, and shocking for one or more times at about 1 to 2 kV (a 3- to 25-µF capacitance may be used initially while optimizing the reaction); returning the cuvette to ice; diluting the transformed cells 20-fold in complete medium; and harvesting the protoplasts after about 48 hours.

Host Cells and Host Organisms

The methods, compositions, NVPs, and NVP-antimicrobial proteins of the present disclosure may be implemented in any host organism. For example, in some embodiments, the host organism can be a cell. In some embodiments, the cell can be, e.g., a eukaryotic or prokaryotic cell.

In some embodiments, the host cell used to produce a NVP or NVP-antimicrobial protein can be eukaryote.

In some embodiments, the host cell used to produce a NVP or NVP-antimicrobial protein may be any species within the genera, *Kluyveromyces*.

In some embodiments, the host cell used to produce a NVP or NVP-antimicrobial protein may be a species in the genera, *Kluyveromyces*, e.g., the host cell may be one of the following: *Kluyveromyces aestuarii, Kluyveromyces dobzhanskii, Kluyveromyces lactis, Kluyveromyces marxianus, Kluyveromyces nonfermentans,* or *Kluyveromyces wickerhamii.*

In some embodiments, the host cell used to produce a NVP or NVP-antimicrobial protein may be a species within the *Pichia* genus. For example, the host cell may be one of the following: *Pichia farinose, Pichia anomala, Pichia heedii, Pichia guilliermondii, Pichia kluyveri, Pichia membranfaciens, Pichia norvegensis, Pichia ohmeri, Pichia pastoris, Pichia methanolica,* or *Pichia subpelliculosa.*

In some embodiments, the host cell used to produce a NVP or NVP-antimicrobial protein may be a species within the *Saccharomyces* genus. For example, the host cell may be one of the following: *Saccharomyces arboricolus, Saccharomyces bayanus, Saccharomyces bulderi, Saccharomyces cariocanus, Saccharomyces cariocus, Saccharomyces cerevisiae, Saccharomyces cerevisiae* var *boulardii, Saccharomyces chevalieri, Saccharomyces dairenensis, Saccharomyces ellipsoideus, Saccharomyces eubayanus, Saccharomyces exiguous, Saccharomyces florentinus, Saccharomyces fragilis, Saccharomyces kudriavzevii, Saccharomyces martiniae, Saccharomyces mikatae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum,* or *Saccharomyces zonatus.*

In some embodiments, the procedures and methods described here can be accomplished using a host cell that is a *Kluyveromyces lactis, Kluyveromyces marxianus, Saccharomyces cerevisiae, Pichia pastoris, Pichia methanolica, Schizosaccharomyces pombe,* or *Hansenula anomala.*

In some embodiments, the procedures and methods described here can be accomplished with any species of yeast, including but not limited to any species of *Hansenula* species including any species of *Hansenula* and preferably *Hansenula polymorpha*. In some embodiments, the procedures and methods described here can be accomplished with any species of yeast, including but not limited to any species of *Yarrowia* species for example, *Yarrowia lipolytica*. In some embodiments, the procedures and methods described here can be accomplished with any species of yeast, including but not limited to any species of *Schizosaccharomyces* species including any species of *Schizosaccharomyces* and preferably *Schizosaccharomyces pombe*.

In some embodiments, yeast species such as *Kluyveromyces lactis, Saccharomyces cerevisiae, Pichia pastoris,* and others, can be used as a host organism. Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5): 325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Recipes for yeast cell fermentation media and stocks are described herein.

Yeast Strains

The present disclosure contemplates the creation of yeast strains operable to express an NVP or an NVP-antimicrobial protein. For example, in some embodiments, a host cell can be transformed with a polynucleotide operable to encode an NVP (e.g., by using any of the vectors described herein). In some embodiments, that host cell can be yeast strain.

In some embodiments, a yeast strain can be produced by preparing a vector comprising a first expression cassette comprising a polynucleotide operable to express a NVP or complementary nucleotide sequence thereof.

In some embodiments, the present disclosure comprises, consists essentially of, or consists of, a yeast strain comprising: a first expression cassette comprising a polynucleotide operable to encode an NVP, said NVP comprising an amino acid sequence that is at least 90%, 95%, 96%, 97%, 98%, 99%, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or a complementary nucleotide sequence thereof.

In some embodiments, the present disclosure comprises, consists essentially of, or consists of, a yeast strain comprising: a first expression cassette comprising a polynucleotide operable to encode an NVP, said NVP comprising, consisting essentially of, or consisting of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or an agriculturally acceptable salt thereof.

In some embodiments, the present disclosure comprises, consists essentially of, or consists of, a yeast strain comprising: a first expression cassette comprising a polynucleotide operable to encode an NVP, said NVP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine.

In some embodiments, the present disclosure comprises, consists essentially of, or consists of, a yeast strain comprising: a first expression cassette comprising a polynucleotide operable to encode an NVP, said NVP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is V, L, I, M, F, W, P, S, T, Y, N, Q, D, E, K, R, or H; or a complementary nucleotide sequence thereof.

In some embodiments, the present disclosure comprises, consists essentially of, or consists of, a yeast strain comprising: a first expression cassette comprising a polynucleotide operable to encode an NVP, said NVP comprising, consisting essentially of, or consisting of, an amino acid sequence that is at least is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is L, M, F, W, S, Y, D, or E; or a complementary nucleotide sequence thereof.

In some embodiments, the yeast strain comprises a polynucleotide which enables the synthesis of an NVP, wherein the NVP comprises, consists essentially of, or consists of, an amino sequence that is at least 90%, 95%, 96%, 97%, 98%, 99%, or 100% as the amino acid sequence set forth in any one of SEQ ID NOs: 4-19, or 66, or a complementary nucleotide sequence thereof.

In some embodiments, the yeast strain comprises a polynucleotide which enables the synthesis of an NVP, wherein the NVP comprises, consists essentially of, or consists of, an amino sequence that is at least 90%, 95%, 96%, 97%, 98%, 99%, or 100% as the amino acid sequence set forth in any one of SEQ ID NOs: 5, 7, 8, 9, 11, 13, 16, and 17, or a complementary nucleotide sequence thereof.

In some embodiments, the yeast strain is selected from any species belonging to the genera *Saccharomyces, Pichia, Kluyveromyces, Hansenula, Yarrowia* or *Schizosaccharomyces*.

In some embodiments, the yeast cell is selected from the group consisting of *Kluyveromyces lactis, Kluyveromyces marxianus, Saccharomyces cerevisiae,* and *Pichia pastoris*.

In some embodiments, the yeast cell is *Kluyveromyces lactis* or *Kluyveromyces marxianus*.

In some embodiments, a yeast strain can be operable to express an NVP or NVP-antimicrobial protein, wherein the NVP is a homopolymer or heteropolymer of two or more NVPs, wherein the amino acid sequence of each NVP is the same or different.

In some embodiments, a yeast strain can be operable to express an NVP or NVP-antimicrobial protein, wherein the NVP is a fused protein comprising two or more NVPs separated by a cleavable or non-cleavable linker, and wherein the amino acid sequence of each NVP may be the same or different.

In some embodiments, the linker is a cleavable linker.

In some embodiments, the linker has an amino acid sequence as set forth in any one of SEQ ID NOs: 39-51.

In some embodiments, the linker is cleavable inside at least one of (i) the gut or hemolymph of an invertebrate, and (ii) cleavable inside the gut of a mammal.

In some embodiments, a yeast strain can be operable to express an NVP or NVP-antimicrobial protein, wherein the vector is a plasmid comprising an alpha-MF signal.

In some embodiments, a yeast strain can be operable to express an NVP or NVP-antimicrobial protein, wherein the vector is transformed into a yeast strain.

In some embodiments, a yeast strain can be operable to express an NVP or NVP-antimicrobial protein, wherein the yeast strain is selected from any species of the genera *Saccharomyces, Pichia, Kluyveromyces, Hansenula, Yarrowia* or *Schizosaccharomyces*.

In some embodiments, a yeast strain can be operable to express an NVP or NVP-antimicrobial protein, wherein the yeast strain is selected from the group consisting of *Kluyveromyces lactis, Kluyveromyces marxianus, Saccharomyces cerevisiae*, and *Pichia pastoris*.

In some embodiments, a yeast strain can be operable to express an NVP or NVP-antimicrobial protein, wherein the yeast strain is *Kluyveromyces lactis*.

In some embodiments, a yeast strain can be operable to express an NVP or NVP-antimicrobial protein, wherein expression of the NVP provides a yield of at least: 70 mg/L, 80 mg/L, 90 mg/L, 100 mg/L, 110 mg/L, 120 mg/L, 130 mg/L, 140 mg/L, 150 mg/L, 160 mg/L, 170 mg/L, 180 mg/L, 190 mg/L 200 mg/L, 500 mg/L, 750 mg/L, 1,000 mg/L, 1,250 mg/L, 1,500 mg/L, 1,750 mg/L or at least 20,000 mg/L, or more, of NVP per liter of medium.

In some embodiments, a yeast strain can be operable to express an NVP or NVP-antimicrobial protein, wherein expression of the NVP provides a yield of at least 100 mg/L of NVP per liter of medium.

In some embodiments, a yeast strain can be operable to express an NVP or NVP-antimicrobial protein, wherein expression of the NVP in the medium results in the expression of a single NVP in the medium.

In some embodiments, a yeast strain can be operable to express an NVP or NVP-antimicrobial protein, wherein expression of the NVP in the medium results in the expression of an NVP polymer comprising two or more NVP polypeptides in the medium.

In some embodiments, a yeast strain can be operable to express an NVP or NVP-antimicrobial protein, wherein the vector comprises two or three expression cassettes, each expression cassette operable to encode the NVP of the first expression cassette.

In some embodiments, a yeast strain can be operable to express an NVP or NVP-antimicrobial protein, wherein the vector comprises two or three expression cassettes, each expression cassette operable to encode the NVP of the first expression cassette, or an NVP of a different expression cassette.

In some embodiments, a yeast strain can be operable to express an NVP or NVP-antimicrobial protein, wherein the expression cassette is operable to encode an NVP as set forth in any one of SEQ ID NOs: 4-19, or 66.

In some embodiments, a yeast strain can be operable to express an NVP or NVP-antimicrobial protein, wherein the expression cassette is operable to encode an NVP as set forth in any one of SEQ ID NOs: 5, 7, 8, 9, 11, 13, 16, and 17.

Any of the aforementioned methods, and/or any of the methods described herein, can be used to produce one or more of the NVPs or NVP-antimicrobial proteins as described herein. For example, any of the methods described herein can be used to produce one or more of the NVPs described in the present disclosure, e.g., an NCR13 variant peptide (NVP) of the present disclosure which comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises at least one mutation relative to a WT-NCR13 amino acid sequence as set forth in SEQ ID NO: 1; wherein $X_1$ is an amino acid addition to the N-terminus of the WT-NCR13 amino acid sequence; and wherein $X_1$ is any natural or non-natural amino acid other than glycine or alanine, for example, an exemplary NVPs having the amino acid sequence of SEQ ID NOs: 4-19, or 66, which are likewise described herein.

Yeast Transformation, NVP Purification, and Analysis

An exemplary method of yeast transformation is as follows: first, expression vectors carrying an NVP ORF are transformed into yeast cells; the expression vectors are usually linearized by specific restriction enzyme cleavage to facilitate chromosomal integration via homologous recombination. The linear expression vector is then transformed into yeast cells by a chemical or electroporation method of transformation and integrated into the targeted locus of the yeast genome by homologous recombination. The integration can happen at the same chromosomal locus multiple times; therefore, the genome of a transformed yeast cell can contain multiple copies of NVP expression cassettes. The successfully transformed yeast cells can be identified using growth conditions that favor a selection marker engineered into the expression vector and co-integrated into yeast chromosomes with the NVP ORF; examples of such markers include, but are not limited to, acetamide prototrophy, zeocin resistance, geneticin resistance, nourseothricin resistance, and uracil prototrophy.

Selection markers are well known in the art, and any of these well-known selection markers can be implemented in the present disclosure. For example, in some embodiments, a selection marker can be a positive selection marker, or negative selection marker. Positive selection markers permit the selection for cells in which the gene product of the marker is expressed. This generally comprises contacting cells with an appropriate agent that, but for the expression of the positive selection marker, kills or otherwise selects against the cells. An exemplary method of using selection markers is disclosed in U.S. Pat. No. 5,464,764, the disclosure of which is incorporated herein by reference in its entirety. Additional exemplary descriptions and methods concerning selection markers are provided in Wigler et al., Cell 11:223 (1977); Szybalska & Szybalski, Proc. Natl. Acad. Sci. USA 48:202 (1992); Lowy et al., Cell 22:817 (1980); Wigler et al., Natl. Acad. Sci. USA 77:357 (1980); O'Hare et al., Proc. Natl. Acad. Sci. USA 78:1527 (1981); Mulligan & Berg, Proc. Natl. Acad. Sci. USA 78:2072 (1981); Wu and Wu, Biotherapy 3:87-95 (1991); Tolstoshev, Ann. Rev. Pharmacol. Toxicol. 32:573-596 (1993); Mulligan, Science 260:926-932 (1993); Morgan and Anderson, Ann. Rev. Biochem. 62:191-217 (1993); Santerre et al., Gene 30:147 (1984); Ausubel et al. (eds.), Current Protocols in Molecular Biology, John Wiley & Sons, N Y (1993); Kriegler, Gene Transfer and Expression, A Laboratory Manual, Stockton Press, N Y (1990); in Chapters 12 and 13, Dracopoli et al. (eds), Current Protocols in Human Genetics, John Wiley & Sons, N Y (1994); Colberre-Garapin et al., J. Mol. Biol. 150:1 (1981); U.S. Pat. No. 6,548,285 (filed Apr. 3, 1997); U.S. Pat. No. 6,165,715 (filed Jun. 22, 1998); and 6,110,707 (filed Jan. 17, 1997), the disclosures of which are incorporated by reference herein in their entireties.

Due to the influence of unpredictable and variable factors- such as epigenetic modification of genes and networks of genes, and variation in the number of integration events that occur in individual cells in a population undergoing a transformation procedure-individual yeast colonies of a given transformation process will differ in their capacities to produce an NVP ORF. Therefore, transgenic yeast colonies carrying the NVP transgenes should be screened for high yield strains. Two effective methods for such screening—each dependent on growth of small-scale cultures of the transgenic yeast to provide conditioned media samples for subsequent analysis—use reverse-phase HPLC or housefly injection procedures to analyze conditioned media samples from the positive transgenic yeast colonies.

The transgenic yeast cultures can be obtained, e.g., using 14 mL round bottom polypropylene culture tubes with 5 to 10 mL defined medium added to each tube, or in 48-well deep well culture plates with 2.2 mL defined medium added to each well. The defined medium, not containing crude proteinaceous extracts or by-products such as yeast extract or peptone, is used for the cultures to reduce the protein background in the conditioned media harvested for the later screening steps. The cultures are performed at the optimal temperature, for example, 23.5° C. for *K. lactis*, for about 5-6 days, until the maximum cell density is reached. NVPs will now be produced by the transformed yeast cells and secreted out of cells to the growth medium. To prepare samples for the screening, cells are removed from the cultures by centrifugation and the supernatants are collected as the conditioned media, which are then cleaned by filtration through 0.22 μm filter membrane and then made ready for strain screening.

In some embodiments, positive yeast colonies transformed with NVP can be screened via reverse-phase HPLC (rpHPLC) screening of putative yeast colonies. In this screening method, an HPLC analytic column with bonded phase of C18 can be used. Acetonitrile and water are used as mobile phase solvents, and a UV absorbance detector set at 220 nm is used for the peptide detection. Appropriate amounts of the conditioned medium samples are loaded into the rpHPLC system and eluted with a linear gradient of mobile phase solvents. The corresponding peak area of the antimicrobial peptide in the HPLC chromatograph is used to quantify the NVP concentrations in the conditioned media. Known amounts of pure NVP are run through the same rpHPLC column with the same HPLC protocol to confirm the retention time of the peptide and to produce a standard peptide HPLC curve for the quantification.

An exemplary reverse-phase HPLC screening process of positive *K. lactis* cells is as follows: an NVP ORF can be inserted into the expression vector, pKLAC1, and transformed into the *K. lactis* strain, YCT306, from New England Biolabs, Ipswich, Mass., USA. pKLAC1 vector is an integrative expression vector. Once the NVP transgenes were cloned into pKLAC1 and transformed into YCT306, their expression was controlled by the LAC4 promoter. The resulting transformed colonies produced pre-propeptides comprising an α-mating factor signal peptide, a Kex2 cleavage site and mature NVPs. The α-Mating factor signal peptide guides the pre-propeptides to enter the endogenous secretion pathway, and mature NVPs are released into the growth media.

In some embodiments, codon optimization for NVP expression can be performed in two rounds, for example, in the first round, based on some common features of high expression DNA sequences, multiple variants of the NVP ORF, expressing an α-Mating factor signal peptide, a Kex2 cleavage site and the NVP, are designed and their expression levels are evaluated in the YCT306 strain of *K. lactis*, resulting in an initial *K. lactis* expression algorithm; in a second round of optimization, additional variant NVP ORFs can be designed based on the initial *K. lactis* expression algorithm to further fine-tuned the *K. lactis* expression algorithm, and identify the best ORF for NVP expression in *K. lactis*. In some embodiments, the resulting DNA sequence from the foregoing optimization can have an open reading frame encoding an α-MF signal peptide, a Kex2 cleavage site and an NVP, which can be cloned into the pKLAC1 vector using Hind III and Not I restriction sites, resulting in NVP expression vectors.

In some embodiments, the yeast, *Pichia pastoris*, can be transformed with an NVP expression cassette. An exemplary method for transforming *P. pastoris* is as follows: yeast vectors can be used to transform an NVP expression cassette into *P. pastoris*. The vectors can be obtained from commercial vendors known to those having ordinary skill in the art. In some embodiments, the vectors can be integrative vectors, and may use the uracil phosphoribosyltransferase promoter (pUPP) to enhance the heterologous transgene expression. In some embodiments, the vectors may offer different selection strategies; e.g., in some embodiments, the only difference between the vectors can be that one vector may provide G418 resistance to the host yeast, while the other vector may provide Zeocin resistance. In some embodiments, pairs of complementary oligonucleotides, encoding the NVP may be designed and synthesized for subcloning into the two yeast expression vectors. Hybridization reactions can be performed by mixing the corresponding complementary oligonucleotides to a final concentration of 20 μM in 30 mM NaCl, 10 mM Tris-Cl (all final concentrations), pH 8, and then incubating at 95° C. for 20 min, followed by a 9-hour incubation starting at 92° C. and ending at 17° C., with 3° C. drops in temperature every 20 min. The hybridization reactions will result in DNA fragments encoding NVP. The two *P. pastoris* vectors can be digested with BsaI-HF restriction enzymes, and the double stranded DNA products of the reactions are then subcloned into the linearized *P. pastoris* vectors using standard procedures. Following verification of the sequences of the subclones, plasmid aliquots can be transfected by electroporation into a *P. pastoris* strain (e.g., Bg08). The resulting transformed yeast, can be selected based on resistance (e.g., in this example, to Zeocin or G418) conferred by elements engineered into the vectors.

Methods of protein purification are well-known in the art, and any known method can be employed to purify and/or recover NVPs of the present disclosure. For example, in some embodiments, the following procedures are exemplary of suitable purification procedures: fractionation on immunoaffinity or ion-exchange columns; ethanol precipitation; reverse phase HPLC; chromatography on silica, or on a cation-exchange resin such as DEAE; chromatofocusing; SDS-PAGE; ammonium sulfate precipitation; gel filtration using, for example, Sephadex G-75; and the like. In some embodiments, proteins of the present disclosure can be purified using one of the following: affinity chromatography; ion exchange chromatography; filtration; electrophoresis; hydrophobic interaction chromatography; gel filtration chromatography; reverse phase chromatography; concanavalin A chromatography; and differential solubilization.

Exemplary methods of protein purification are provided in: U.S. Pat. Nos. 6,339,142; 7,585,955; 8,946,395; 9,067,990; 10,246,484; and Marshak et al., "Strategies for Protein Purification and Characterization—A Laboratory Course Manual" CSHL Press (1996); the disclosures of which are incorporated herein by reference in their entireties.

Peptide Yield Screening and Evaluation

Peptide yield can be determined by any of the methods known to those of skill in the art (e.g., capillary gel electrophoresis (CGE), Western blot analysis, and the like). Activity assays, as described herein and known in the art, can also provide information regarding peptide yield. In some embodiments, these or any other methods known in the art can be used to evaluate peptide yield.

Quantification Assays

In some embodiments, and without limitation, NVP peptide yield can be measured using: HPLC; Mass spectrometry (MS) and related techniques; LC/MS/MS; reverse phase protein arrays (RPPA); immunohistochemistry; ELISA; suspension bead array, mass spectrometry; dot blot; SDS-PAGE; capillary gel electrophoresis (CGE); Western blot analysis; Bradford assay; measuring UV absorption at 260 nm; Lowry assay; Smith copper/bicinchoninic assay; a secretion assay; Pierce protein assay; Biuret reaction; and the like. Exemplary methods of protein quantification are provided in Stoscheck, C. 1990 "Quantification of Protein" *Methods in Enzymology,* 182:50-68; Lowry, O. Rosebrough, A., Farr, A. and Randall, R. 1951 *J. Biol. Chem.* 193:265; Smith, P. et al., (1985) Anal. Biochem. 150:76-85; Bradford, M. 1976 "A Rapid and Sensitive Method for the Quantitation of Microgram Quantities of Protein Utilizing the Principle of Protein-Dye Binding" Anal. Biochem. 72:248-254; Cabib, E. and Polacheck, I. 1984 "Protein assay for dilute solutions." Methods in Enzymology, 104:318-328; Turcanu, Victor; Williams, Neil A. (2001). "Cell identification and isolation on the basis of cytokine secretion: A novel tool for investigating immune responses." Nature Medicine. 7 (3): 373-376; U.S. Pat. No. 6,391,649; the disclosures of which are incorporated herein by reference in their entireties.

In other embodiments, NVP peptide yield can be quantified and/or assessed using methods that include, without limitation: recombinant protein mass per volume of culture (e.g., gram or milligrams protein per liter culture); percent or fraction of recombinant protein insoluble precipitate obtained after cell lysis determined in (e.g., recombinant protein extracted supernatant in an amount/amount of protein in the insoluble components); percentage or fraction of active protein (e.g., an amount/analysis of the active protein for use in protein amount); total cell protein (tcp) percentage or fraction; and/or the amount of protein/cell and the dry biomass of a percentage or ratio.

In some embodiments, wherein yield is expressed in terms of culture volume, the culture cell density may be taken into account, particularly when yields between different cultures are being compared.

In some embodiments, the present disclosure provides a method of producing a heterologous polypeptide that is at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of heterologous polypeptide in the host cell as a percentage of aggregate cellular protein. The determination of the percent total cell protein is well known in the art.

"Total cell protein (tcp)" or "Percent total cell protein (% tcp)" is the amount of protein or polypeptide in the host cell as a percentage of aggregate cellular protein. Methods for the determination of the percent total cell protein are well known in the art.

In some embodiments, HPLC can be used to quantify peptide yield. For example, in some embodiments, peptide yield can be quantified using an Agilent 1100 HPLC system equipped with an Onyx monolithic 4.5×100 mm, C18 reverse-phase analytical HPLC column and an auto-injector. An illustrative use of the Agilent 1100 HPLC system equipped with an Onyx monolithic 4.5×100 mm, C18 reverse-phase analytical HPLC column and an auto-injector is as follows: filtered conditioned media samples from transformed *K. lactis* cells are analyzed using Agilent 1100 HPLC system equipped with an Onyx monolithic 4.5×100 mm, C18 reverse-phase analytical HPLC column and an auto-injector by analyzing HPLC grade water and acetonitrile containing 0.1% trifluoroacetic acid, constituting the two mobile phase solvents used for the HPLC analyses; the peak areas of both the NVP or NVP-antimicrobial protein are analyzed using HPLC chromatographs, and then used to calculate the peptide concentration in the conditioned media, which can be further normalized to the corresponding final cell densities (as determined by OD600 measurements) as normalized peptide yield.

Activity Assays

In some embodiments, positive yeast colonies transformed with NVP or NVP-antimicrobial protein can be screened using a housefly injection assay. NVP or NVP-antimicrobial protein can paralyze/kill houseflies when injected in measured doses through the body wall of the dorsal thorax. The efficacy of the NVP or NVP-antimicrobial protein can be defined by the median paralysis/lethal dose of the peptide ($PD_{50}/LD_{50}$), which causes 50% knock-down ratio or mortality of the injected houseflies respectively. The pure NVP or NVP-antimicrobial protein is normally used in the housefly injection assay to generate a standard dose-response curve, from which a $PD_{50}/LD_{50}$ value can be determined. Using a $PD_{50}/LD_{50}$ value from the analysis of a standard dose-response curve of the pure NVP or NVP-antimicrobial protein, quantification of the NVP or NVP-antimicrobial protein produced by the transformed yeast can be achieved using a housefly injection assay performed with serial dilutions of the corresponding conditioned media.

An exemplary housefly injection bioassay is as follows: conditioned media is serially diluted to generate full dose-response curves from the housefly injection bioassay. Before injection, adult houseflies (*Musca domestica*) are immobilized with $CO_2$, and 12-18 mg houseflies are selected for injection. A microapplicator, loaded with a 1 cc syringe and 30-gauge needle, is used to inject 0.5 µL per fly, doses of serially diluted conditioned media samples into houseflies through the body wall of the dorsal thorax. The injected houseflies are placed into closed containers with moist filter paper and breathing holes on the lids, and they are examined by knock-down ratio or by mortality scoring at 24 hours post-injection. Normalized yields are calculated. Peptide yield means the peptide concentration in the conditioned media in units of mg/L. However, peptide yields are not always sufficient to accurately compare the strain production rate. Individual strains may have different growth rates, hence when a culture is harvested, different cultures may vary in cell density. A culture with a high cell density may produce a higher concentration of the peptide in the media, even though the peptide production rate of the strain is lower than another strain which has a higher production rate. Accordingly, the term "normalized yield" is created by dividing the peptide yield with the cell density in the corresponding culture and this allows a better comparison of the peptide production rate between strains. The cell density is represented by the light absorbance at 600 nm with a unit of "A" (Absorbance unit).

Screening yeast colonies that have undergone a transformation with a polynucleotide operable to encode an NVP or NVP-antimicrobial protein can identify the high yield yeast strains from hundreds of potential colonies. These strains can be fermented in bioreactor to achieve at least up to 4 g/L or at least up to 3 g/L or at least up to 2 g/L yield of the NVP or NVP-antimicrobial protein when using optimized fermentation media and fermentation conditions described herein. The higher rates of production (expressed in mg/L) can be anywhere from about 100 mg/L to about 100,000 mg/L; or from about 100 mg/L to about 90,000 mg/L; or from about 100 mg/L to about 80,000 mg/L; or from about 100 mg/L to about 70,000 mg/L; or from about 100 mg/L to about 60,000 mg/L; or from about 100 mg/L to about 50,000 mg/L; or from about 100 mg/L to about 40,000 mg/L; or from about 100 mg/L to about 30,000 mg/L; or from about 100 mg/L to about 20,000 mg/L; or from about 100 mg/L to about 17,500 mg/L; or from about 100 mg/L to about 15,000 mg/L; or from about 100 mg/L to about 12,500 mg/L; or from about 100 mg/L to about 10,000 mg/L; or from about 100 mg/L to about 9,000 mg/L; or from about 100 mg/L to about 8,000 mg/L; or from about 100 mg/L to about 7,000 mg/L; or from about 100 mg/L to about 6,000 mg/L; or from about 100 mg/L to about 5,000 mg/L; or from about 100 mg/L to about 3,000 mg/L; or from about 100 mg/L to 2,000 mg/L; or from about 100 mg/L to 1,500 mg/L; or from about 100 mg/L to 1,000 mg/L; or from about 100 mg/L to 750 mg/L; or from about 100 mg/L to 500 mg/L; or from about 150 mg/L to 100,000 mg/L; or from about 200 mg/L to 100,000 mg/L; or from about 300 mg/L to 100,000 mg/L; or from about 400 mg/L to 100,000 mg/L; or from about 500 mg/L to 100,000 mg/L; or from about 750 mg/L to 100,000 mg/L; or from about 1,000 mg/L to 100,000 mg/L; or from about 1,250 mg/L to 100,000 mg/L; or from about 1,500 mg/L to 100,000 mg/L; or from about 2,000 mg/L to 100,000 mg/L; or from about 2,500 mg/L to 100,000 mg/L; or from about 3,000 mg/L to 100,000 mg/L; or from about 3,500 mg/L to 100,000 mg/L; or from about 4,000 mg/L to 100,000 mg/L; or from about 4,500 mg/L to 100,000 mg/L; or from about 5,000 mg/L to 100,000 mg/L; or from about 6,000 mg/L to 100,000 mg/L; or from about 7,000 mg/L to 100,000 mg/L; or from about 8,000 mg/L to 100,000 mg/L; or from about 9,000 mg/L to 100,000 mg/L; or from about 10,000 mg/L to 100,000 mg/L; or from about 12,500 mg/L to 100,000 mg/L; or from about 15,000 mg/L to 100,000 mg/L; or from about 17,500 mg/L to 100,000 mg/L; or from about 20,000 mg/L to 100,000 mg/L; or from about 30,000 mg/L to 100,000 mg/L; or from about 40,000 mg/L to 100,000 mg/L; or from about 50,000 mg/L to 100,000 mg/L; or from about 60,000 mg/L to 100,000 mg/L; or from about 70,000 mg/L to 100,000 mg/L; or from about 80,000 mg/L to 100,000 mg/L; or from about 90,000 mg/L to 100,000 mg/L; or any range of any value provided or even greater yields than can be achieved with a peptide before conversion, using the same or similar production methods that were used to produce the peptide before conversion.

Culture and Fermentation Conditions

Cell culture techniques are well-known in the art. In some embodiments, the culture method and/or materials will necessarily require adaption based on the host cell selected; and, such adaptions (e.g., modifying pH, temperature, medium contents, and the like) are well known to those having ordinary skill in the art. In some embodiments, any known culture technique may be employed to produce an NVP or NVP-antimicrobial protein of the present disclosure.

Exemplary culture methods are provided in U.S. Pat. Nos. 3,933,590; 3,946,780; 4,988,623; 5,153,131; 5,153,133; 5,155,034; 5,316,905; 5,330,908; 6,159,724; 7,419,801; 9,320,816; 9,714,408; and 10,563,169; the disclosures of which are incorporated herein by reference in their entireties.

Yeast Culture

Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5):325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Yeast can be cultured in a variety of media, e.g., in some embodiments, yeast can be cultured in minimal medium; YPD medium; yeast synthetic drop-out medium; Yeast Nitrogen Base (YNB with or without amino acids); YEPD medium; ADE D medium; ADE DS" medium; LEU D medium; HIS D medium; or Mineral salts medium.

In some embodiments, yeast can be cultured in minimal medium. In some embodiments, minimal medium ingredients can comprise: 2% Sugar; Phosphate Buffer, pH 6.0; Magnesium Sulfate; Calcium Chloride; Ammonium Sulfate; Sodium Chloride; Potassium Chloride; Copper Sulfate; Manganese Sulfate; Zinc Chloride; Potassium Iodide; Cobalt Chloride; Sodium Molybdate; Boric Acid; Iron Chloride; Biotin; Calcium pantothenate; Thiamine; Myo-inositol; Nicotinic Acid; and Pyridoxine.

In some embodiments, yeast can be cultured in YPD medium. YPD medium comprises a bacteriological peptone, yeast extract, and glucose.

In some embodiments, yeast can be cultured in yeast synthetic drop-out medium, which can be used to differentiate auxotrophic mutant strains that cannot grow without a specific medium component transformed with a plasmid that allows said transformant to grow on a medium lacking the required component.

In some embodiments, yeast can be cultured using Yeast Nitrogen Base (YNB with or without amino acids), which comprises nitrogen, vitamins, trace elements, and salts.

In some embodiments, the medium can be YEPD medium, e.g., a medium comprising 2% D-glucose, 2% BACTO Peptone (Difco Laboratories, Detroit, Mich.), 1% BACTO yeast extract (Difco), 0.004% adenine, and 0.006% L-leucine; or, a variation thereof, wherein the carbon source is a sugar alcohol, e.g., glycerol or sorbitol In some embodiments, the medium can be ADE D medium, e.g., a medium comprising 0.056%-Ade-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol In some embodiments, the medium can be ADE DS" medium, e.g., a medium comprising 0.056%-Ade-Trp-Thr powder, 0.67% yeast nitrogen base without amino acids, 2% D-glucose, 0.5% 200× tryptophan, threonine solution, and 18.22% D-sorbitol; or, a variation thereof, wherein the carbon source is entirely a sugar alcohol, e.g., glycerol or sorbitol In some embodiments, the medium can be LEU D medium e.g., a medium comprising 0.052%-Leu-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol.

In some embodiments, the medium can be HIS D medium, e.g., a medium comprising 0.052%-His-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol.

In some embodiments, a mineral salts medium can be used. Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium. See, Davis & Mingioli (1950) J. Bact. 60:17-28. The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source.

In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, the disclosure of which is incorporated herein by reference in its entirety. Details of cultivation procedures and mineral salts media useful in the methods of the present disclosure are described by Riesenberg, D et al., 1991, "High cell density cultivation of *Escherichia coli* at controlled specific growth rate," J. Biotechnol. 20 (1):17-27.

In some embodiments, *Kluyveromyces lactis* are grown in minimal media supplemented with 2% glucose, galactose, sorbitol, or glycerol as the sole carbon source. Cultures are incubated at 30° C. until mid-log phase (24-48 hours) for β-galactosidase measurements, or for 6 days at 23.5° C. for heterologous protein expression.

In some embodiments, yeast cells can be cultured in 48-well Deep-well plates, sealed after inoculation with sterile, air-permeable cover. Colonies of yeast, for example, *K. lactis* cultured on plates can be picked and inoculated the deep-well plates with 2.2 mL media per well, composed of DMSor. Inoculated deep-well plates can be grown for 6 days at 23.5° C. with 280 rpm shaking in a refrigerated incubator-shaker. On day 6 post-inoculation, conditioned media should be harvested by centrifugation at 4000 rpm for 10 minutes, followed by filtration using filter plate with 0.22 μM membrane, with filtered media are subject to HPLC analyses.

In some embodiments, yeast species such as *Kluyveromyces lactis, Saccharomyces cerevisiae, Pichia pastoris*, and others, can be used as a host organism, and/or the yeast to be modified using the methods described herein.

Temperature and pH conditions will vary depending on the stage of culture and the host cell species selected. Variables such as temperature and pH in cell culture are readily known to those having ordinary skill in the art.

The pH level is important in the culturing of yeast. One of skill in the art will appreciate that the culturing process includes not only the start of the yeast culture but the maintenance of the culture as well. The yeast culture may be started at any pH level, however, since the media of a yeast culture tends to become more acidic (i.e., lowering the pH) over time, care must be taken to monitor the pH level during the culturing process.

In some embodiments of the invention, the yeast is grown in a medium at a pH level that is dictated based on the species of yeast used, the stage of culture, and/or the temperature. Thus, in some embodiments, the pH level can fall within a range from about 2 to about 10. Those having ordinary skill in the art will recognize that the optimum pH for most microorganisms is near the neutral point (pH 7.0). However, in some embodiments, some fungal species prefer an acidic environment: accordingly, in some embodiments, the pH can range from 2 to 6.5. In some embodiments, the pH can range from about 4 to about 4.5. Some fungal species (e.g., molds) can grow can grow in a pH of from about 2 to about 8.5, but favor an acid pH. See Mountney & Gould, Practical food microbiology and technology. 1988. Ed. 3; and Pena et al., Effects of high medium pH on growth, metabolism and transport in *Saccharomyces cerevisiae*. FEMS Yeast Res. 2015 March; 15(2):fou005.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8.

In some embodiments, the pH of the medium can be at least 5.5. In other aspects, the medium can have a pH level of about 5.5. In other aspects, the medium can have a pH level of between 4 and 8. In some cases, the culture is maintained at a pH level of between 5.5 and 8. In other aspects, the medium has a pH level of between 6 and 8. In some cases, medium has a pH level that is maintained at a pH level of between 6 and 8. In some embodiments, the yeast is grown and/or maintained at a pH level of between 6.1 and 8.1. In some embodiments, the yeast is grown and/or maintained at a pH level of between 6.2 and 8.2. In some embodiments, the yeast is grown and/or maintained at a pH level of between 6.3 and 8.3. In some embodiments, the yeast is grown and/or maintained at a pH level of between 6.4 and 8.4. In some embodiments, the yeast is grown and/or maintained at a pH level of between 5.5 and 8.5. In some embodiments, the yeast is grown and/or maintained at a pH level of between 6.5 and 8.5. In some embodiments, the yeast is grown at a pH level of about 5.6, 5.7, 5.8 or 5.9. In some embodiments, the yeast is grown at a pH level of about 6. In some embodiments, the yeast is grown at a pH level of about 6.5. In some embodiments, the yeast is grown at a pH level of about 6, 6.1, 6.2, 6.3, 6.4, 6.5, 6.6, 6.7, 6.8, 6.9 or 7.0. In some embodiments, the yeast is grown at a pH level of about 7, 7.1, 7.2, 7.3, 7.4, 7.5, 7.6, 7.7, 7.8, 7.9, or 8.0. In some embodiments, the yeast is grown at a level of above 8.

In some embodiments, the pH of the medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

Exemplary methods of yeast culture can be found in U.S. Pat. No. 5,436,136, entitled "Repressible yeast promoters" (filed Dec. 20, 1991; assignee Ciba-Geigy Corporation); U.S. Pat. No. 6,645,739, entitled "Yeast expression systems, methods of producing polypeptides in yeast, and compositions relating to same" (filed Jul. 26, 2001; assignee Phoenix Pharmacologies, Inc., Lexington, Ky.); and U.S. Pat. No. 10,023,836, entitled "Medium for yeasts" (filed Aug. 23, 2013; assignee Yamaguchi University); the disclosures of which are incorporated herein by reference in their entireties.

Fermentation

The present disclosure contemplates the culture of host organisms in any fermentation format. For example, batch, fed-batch, semi-continuous, and continuous fermentation modes may be employed herein.

Fermentation may be performed at any scale. The methods and techniques contemplated according to the present disclosure are useful for recombinant protein expression at any scale. Thus, in some embodiments, e.g., microliter-scale, milliliter scale, centiliter scale, and deciliter scale fermentation volumes may be used, and 1 Liter scale and larger fermentation volumes can be used.

In some embodiments, the fermentation volume is at or above about 1 Liter. For example, in some embodiments, the fermentation volume is about 1 liter to about 100 liters. In some embodiments, the fermentation volume is about 1 liter, about 2 liters, about 3 liters, about 4 liters, about 5 liters, about 6 liters, about 7 liters, about 8 liters, about 9 liters, or about 10 liters. In some embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

In some embodiments, the fermentation medium can be a nutrient solution used for growing and or maintaining cells. Without limitation, this solution ordinarily provides at least one component from one or more of the following categories: (1) an energy source, usually in the form of a carbon source, e.g., glucose; (2) all essential amino acids, and usually the basic set of twenty amino acids; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

In some embodiments, the fermentation medium can be the same as the cell culture medium or any other media described herein. In some embodiments, the fermentation medium can be different from the cell culture medium. In some embodiments, the fermentation medium can be modified in order to accommodate the large-scale production of proteins.

In some embodiments, the fermentation medium can be supplemented electively with one or more components from any of the following categories: (1) hormones and other growth factors such as, serum, insulin, transferrin, and the like; (2) salts, for example, magnesium, calcium, and phosphate; (3) buffers, such as HEPES; (4) nucleosides and bases such as, adenosine, thymidine, etc.; (5) protein and tissue hydrolysates, for example peptone or peptone mixtures which can be obtained from purified gelatin, plant material, or animal byproducts; (6) antibiotics, such as gentamycin; and (7) cell protective agents, for example pluronic polyol.

In some embodiments, the pH of the fermentation medium can be maintained using pH buffers and methods known to those of skill in the art. Control of pH during fermentation can also can be achieved using aqueous ammonia. In some embodiments, the pH of the fermentation medium will be selected based on the preferred pH of the organism used. Thus, in some embodiments, and depending on the host cell and temperature, the pH can range from about to 1 to about 10.

In some embodiments, the pH of the fermentation medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8

In some embodiments, e.g., where *Escherichia coli* (*E. coli*) is used, the optimal pH range is between 6.5 and 7.5, depending on the temperature.

In other embodiments, e.g., where a yeast strain is used, the pH can range from about 4.0 to 8.0.

In some embodiments, neutral pH, i.e., a pH of about 7.0 can be used.

Those having ordinary skill in the art will recognize that during fermentation, the pH levels may drift as result of conversion and production of substrates and metabolic compounds.

In some embodiments, the fermentation medium can be supplemented with a buffer or other chemical in order to avoid changes to the pH. For example, in some embodiments, the addition of $Ca(OH)_2$, $CaCO_3$, NaOH, or $NH_4OH$ can be added to the fermentation medium to neutralize the production of acidic compounds that occur, e.g., in some yeast species during industrial processes.

Temperature is another important consideration in the fermentation process; and, like pH considerations, temperature will depend on the type of host cell selected.

In some embodiments, the fermentation temperature is maintained at about 4° C. to about 42° C. In certain embodiments, the fermentation temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C.

In other embodiments, the fermentation temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 32° C., about 31° C. to about 33° C., about 31° C. to about 32° C., about 30° C. to about 33° C., or about 32° C. to about 33° C.

In other embodiments, the temperature is changed during fermentation, e.g., depending on the stage of fermentation.

Fermentation can be achieved with a variety of microorganisms known to those having ordinary skill in the art. Suitable microorganisms for up-scaled production of an NVP or NVP-antimicrobial protein include any microorganism listed herein. In some embodiments, non-limiting examples of microorganisms include strains of the genus *Saccharomyces* spp. (including, but not limited to, *S. cerevisiae* (baker's yeast), *S. distaticus, S. uvarum*), or the genus *Kluyveromyces*, (including, but not limited to, *K. marxianus, K. fragilis*). See, e.g., Philippidis, G. P., 1996, Cellulose bioconversion technology, in Handbook on Bioethanol: Production and Utilization, Wyman, C. E., ed., Taylor & Francis, Washington, D.C., 179-212.

Fermentation medium may be selected depending on the host cell and/or needs of the end-user. Any necessary supplements besides, e.g., carbon, may also be included at appropriate concentrations introduced alone or as a mixture with another supplement or medium such as a complex nitrogen source.

Yeast Fermentation

Fermentation methods using yeast are well known to those having ordinary skill in the art. In some embodiments, batch fermentation can be used according to the methods provided herein; in other embodiments, continuous fermentation procedures can be used.

In some embodiments, the batch method of fermentation can be used to produce NVPs of the present disclosure. Briefly, the batch method of fermentation refers to a type of fermentation that is performed with a closed system, wherein the composition of the medium is determined at the beginning of the fermentation and is not subject to artificial alterations during the fermentation (i.e., the medium is inoculated with one or more yeast cells at the start of fermentation, and fermentation is allowed to proceed, uninterrupted by the user). Typically, in batch fermentation systems, the metabolite and biomass compositions of the system change constantly up to the time the fermentation is stopped. Within batch cultures, yeast cells pass through a static lag phase to a high growth log phase, and, finally, to a stationary phase, in which the growth rate is diminished or stopped. If untreated, yeast cells in the stationary phase will eventually die. In a batch method, yeast cells in log phase generally are responsible for the bulk of synthesis of end product.

In some embodiments, fed-batch fermentation can be used to produce NVPs of the present disclosure. Briefly, fed-batch fermentation is similar to typical batch method (described above), however, the substrate in the fed-batch method is added in increments as the fermentation progresses. Fed-batch fermentation is useful when catabolite repression may inhibit yeast cell metabolism, and when it is desirable to have limited amounts of substrate in the medium. Generally, the measurement of the substrate concentration in a fed-batch system is estimated on the basis of the changes of measurable factors reflecting metabolism, such as pH, dissolved oxygen, the partial pressure of waste gases (e.g., $CO_2$), and the like.

In some embodiments, the fed-batch fermentation procedure can be used to produce NVPs as follows: culturing a production organism (e.g., a modified yeast cell) in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial first and second carbon source concentration of 20 g/L. As the modified yeast cells grow and utilize the carbon sources, additional 70% carbon source mixture is then fed into the bioreactor at a rate approximately balancing carbon source consumption. The temperature of the bioreactor is generally maintained at 30° C. Growth continues for approximately 24 hours or more, and the heterologous peptides reach a desired concentration, e.g., with the cell density being between about 5 and 10 g/L. Upon completion of the cultivation period, the fermenter contents can be passed through a cell separation unit such as a centrifuge to remove cells and cell debris, and the fermentation broth can be transferred to a product separations unit. Isolation of the heterologous peptides can take place by standard separations procedures well known in the art.

In some embodiments, continuous fermentation can be used to produce NVPs of the present disclosure. Briefly, continuous fermentation refers to fermentation with an open system, wherein a fermentation medium is added continuously to a bioreactor, and an approximately equal amount of conditioned medium is removed simultaneously for processing. Continuous fermentation generally maintains the cultures at a high density, in which yeast cells are primarily in log phase growth. Typically, continuous fermentation methods are performed to maintain steady state growth conditions, and yeast cell loss, due to medium withdrawal, should be balanced against the cell growth rate in the fermentation.

In some embodiments, the continuous fermentation method can be used to produce NVPs as follows: a modified yeast strain can be cultured using a bioreactor apparatus and a medium composition, albeit where the initial first and second carbon source is about, e.g., 30-50 g/L. When the carbon source is exhausted, feed medium of the same composition is supplied continuously at a rate of between about 0.5 L/hr and 1 L/hr, and liquid is withdrawn at the same rate. The heterologous peptide concentration in the bioreactor generally remains constant along with the cell density. Temperature is generally maintained at 30° C., and the pH is generally maintained at about 4.5 using concentrated NaOH and HCl, as required.

In some embodiments, when producing NVPs, the bioreactor can be operated continuously, for example, for about one month, with samples taken every day or as needed to assure consistency of the target chemical compound concentration. In continuous mode, fermenter contents are constantly removed as new feed medium is supplied. The exit stream, containing cells, medium, and heterologous peptides, can then be subjected to a continuous product separations procedure, with or without removing cells and cell debris, and can be performed by continuous separations methods well known in the art to separate organic products from peptides of interest.

In some embodiments, a yeast cell operable to express an NVP or NVP-antimicrobial protein can be grown, e.g., using a fed batch process in aerobic bioreactor. Briefly, reactors are filled to about 20% to about 70% capacity with medium comprising a carbon source and other reagents. Temperature and pH is maintained using one or more chemicals as described herein. Oxygen level is maintained by sparging air intermittently in concert with agitation.

For example, in some embodiments, the present disclosure provides a method of using a fed batch process in aerobic bioreactor, wherein the reactor is filled to about 20%; 21%; 22%; 23%; 24%; 25%; 26%; 27%; 28%; 29%; 30%; 31%; 32%; 33%; 34%; 35%; 36%; 37%; 38%; 39%; 40%; 41%; 42%; 43%; 44%; 45%; 46%; 47%; 48%; 49%; 50%; 51%; 52%; 53%; 54%; 55%; 56%; 57%; 58%; 59%; 60%; 61%; 62%; 63%; 64%; 65%; 66%; 67%; 68%; 69%; or 70% capacity.

In some embodiments, the present disclosure provides a fed batch fermentation method using an aerobic bioreactor to produce NVPs, wherein the medium is a rich culture medium. For example, in some embodiments, the carbon source can be glucose, sorbitol, or lactose.

In some embodiments, the amount of glucose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of sorbitol can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of lactose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the present disclosure provides a fed batch fermentation method using an aerobic bioreactor, wherein the medium is supplemented with one or more of phosphoric acid, calcium sulfate, potassium sulfate, magnesium sulfate heptahydrate, potassium hydroxide, and/or corn steep liquor.

In some embodiments, the medium can be supplemented with phosphoric acid in an amount of about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L to the medium.

In some embodiments, the medium can be supplemented with calcium sulfate in an amount of about 0.05 g/L; 0.15 g/L; 0.25 g/L; 0.35 g/L; 0.45 g/L; 0.55 g/L; 0.65 g/L; 0.75 g/L; 0.85 g/L; 0.95 g/L; 1.05 g/L; 1.15 g/L; 1.25 g/L; 1.35 g/L; 1.45 g/L; 1.55 g/L; 1.65 g/L; 1.75 g/L; 1.85 g/L; 1.95 g/L; 2.05 g/L; 2.15 g/L; 2.25 g/L; 2.35 g/L; 2.45 g/L; 2.55 g/L; 2.65 g/L; 2.75 g/L; 2.85 g/L; or 2.95 g/L to the medium.

In some embodiments, the medium can be supplemented with potassium sulfate in an amount of about 2 g/L; 2.5 g/L; 3 g/L; 3.5 g/L; 4 g/L; 4.5 g/L; 5 g/L; 5.5 g/L; 6 g/L; 6.5 g/L; 7 g/L; 7.5 g/L; 8 g/L; 8.5 g/L; 9 g/L; 9.5 g/L; 10 g/L; 10.5 g/L; 11 g/L; 11.5 g/L; 12 g/L; 12.5 g/L; 13 g/L; 13.5 g/L; 14 g/L; 14.5 g/L; 15 g/L; 15.5 g/L; 16 g/L; 16.5 g/L; 17 g/L; 17.5 g/L; 18 g/L; 18.5 g/L; 19 g/L; 19.5 g/L; or 20 g/L to the medium.

In some embodiments, the medium can be supplemented with magnesium sulfate heptahydrate in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; 7 g/L; 7.25 g/L; 7.5 g/L; 7.75 g/L; 8 g/L; 8.25 g/L; 8.5 g/L; 8.75 g/L; 9 g/L; 9.25 g/L; 9.5 g/L; 9.75 g/L; 10 g/L; 10.25 g/L; 10.5 g/L; 10.75 g/L; 11 g/L; 11.25 g/L; 11.5 g/L; 11.75 g/L; 12 g/L; 12.25 g/L; 12.5 g/L; 12.75 g/L; 13 g/L; 13.25 g/L; 13.5 g/L; 13.75 g/L; 14 g/L; 14.25 g/L; 14.5 g/L; 14.75 g/L; or 15 g/L to the medium.

In some embodiments, the medium can be supplemented with potassium hydroxide in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; or 7 g/L to the medium.

In some embodiments, the medium can be supplemented with corn steep liquor in an amount of about 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; 30 g/L; 31 g/L; 32 g/L; 33 g/L; 34 g/L; 35 g/L; 36 g/L; 37 g/L; 38 g/L; 39 g/L; 40 g/L; 41 g/L; 42 g/L; 43 g/L; 44 g/L; 45 g/L; 46 g/L; 47 g/L; 48 g/L; 49 g/L; 50 g/L; 51 g/L; 52 g/L; 53 g/L; 54 g/L; 55 g/L; 56 g/L; 57 g/L; 58 g/L; 59 g/L; 60 g/L; 61 g/L; 62 g/L; 63 g/L; 64 g/L; 65 g/L; 66 g/L; 67 g/L; 68 g/L; 69 g/L; or 70 g/L to the medium.

In some embodiments, the temperature of the reactor can be maintained between about 15° C. and about 45° C. In some embodiments, the reactor can have a temperature of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In some embodiments, the pH can have a level of about 3 to about 6. In some embodiments, the pH can be 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6.0.

In some embodiments, the pH can be maintained at a constant level via the addition of one or more chemicals. For example, in some embodiments, ammonium hydroxide can be added to maintain pH. In some embodiments, ammonium hydroxide can be added to a level of ammonium hydroxide in the medium that is about 5%, 6%, 7%, 8%, 9%, 10%, 11%, 12%, 13%, 14%, 15, 16%, 17%, 18%, 19%, or 20%, of ammonium hydroxide In some embodiments, oxygen levels can be maintained by sparging. For example, in some embodiments, dissolved oxygen can be maintained at a constant level by sparging air between 0.5-1.5 volume/volume/min and by increasing agitation to maintain a set point of 10-30%.

In some embodiments, inoculation of the reactor can be accomplished based on an overnight seed culture comprising from about 2.5 g/L to about 50 g/L of a carbon source, e.g., glucose, sorbitol, or lactose. In some embodiments, the overnight seed culture can comprise corn steep liquor, e.g., from about 2.5 g/L to about 50 g/L of corn steep liquor.

In some embodiments, the inoculation percentage can range from about 5-20% of initial fill volume. Following inoculation, the reactor can be fed with from about a 50% to about an 80% solution of the selected carbon source up until the reactor is filled and/or the desired supernatant peptide concentration is achieved. In some embodiments, the time required to fill the reactor can range from about 86 hours to about 160 hours. In some embodiments, the quantity required to reach the desired peptide concentration can range from about 0.8 g/L to about 1.2 g/L. Upon completion of the fermentation, the contents can be passed through a cell separation unit and optionally concentrated, depending on intended use of the material.

Additional recipes for yeast fermentation media are provided herein.

Recipes for yeast cell fermentation media and stocks are described as follows: (1) MSM media recipe: 2 g/L sodium citrate dihydrate; 1 g/L calcium sulfate dihydrate (0.79 g/L anhydrous calcium sulfate); 42.9 g/L potassium phosphate monobasic; 5.17 g/L ammonium sulfate; 14.33 g/L potassium sulfate; 11.7 g/L magnesium sulfate heptahydrate; 2 mL/L PTM1trace salt solution; 0.4 ppm biotin (from 500×, 200 ppm stock); 1-2% pure glycerol or other carbon source. (2) PTM1 trace salts solution: Cupric sulfate-5$H_2O$ 6.0 g; Sodium iodide 0.08 g; Manganese sulfate-H2O 3.0 g; Sodium molybdate-2$H_2O$ 0.2 g; Boric Acid 0.02 g; Cobalt chloride 0.5 g; Zinc chloride 20.0 g; Ferrous sulfate-7$H_2O$ 65.0 g; Biotin 0.2 g; Sulfuric Acid 5.0 ml; add Water to a final volume of 1 liter. An illustrative composition for *K. lactis* defined medium (DMSor) is as follows: 11.83 g/L $KH_2PO_4$, 2.299 g/L $K_2HPO_4$, 20 g/L of a fermentable sugar, e.g., galactose, maltose, latotriose, sucrose, fructose or glucose and/or a sugar alcohol, for example, erythritol, hydrogenated starch hydrolysates, isomalt, lactitol, maltitol, mannitol, and xylitol, 1 g/L $MgSO_4·7H_2O$, 10 g/L $(NH_4)SO_4$, 0.33 g/L $CaCl_2·2H_2O$, 1 g/L NaCl, 1 g/L KCl, 5 mg/L $CuSO_4·5H_2O$, 30 mg/L $MnSO_4·H_2O$, 10 mg/L, $ZnCl_2$, 1 mg/L KI, 2 mg/L $COCl_2·6H_2O$, 8 mg/L $Na_2MoO_4·2H_2O$, 0.4 mg/L $H_3BO_3$, 15 mg/L $FeCl_3·6H_2O$, 0.8 mg/L biotin, 20 mg/L Ca-pantothenate, 15 mg/L thiamine, 16 mg/L myo-inositol, 10 mg/L nicotinic acid, and 4 mg/L pyridoxine.

Peptide Degradation

Proteins, polypeptides, and peptides degrade in both biological samples and in solution (e.g., cell culture and/or during fermentation).

Methods of detecting NVP peptide degradation are well known in the art. Any of the well-known methods of detecting peptide degradation (e.g., during fermentation) may be employed here.

In some embodiments, peptide degradation can be detected using isotope labeling techniques; liquid chromatography/mass spectrometry (LC/MS); HPLC; radioactive amino acid incorporation and subsequent detection, e.g., via scintillation counting; the use of a reporter protein, e.g., a protein that can be detected (e.g., by fluorescence, spectroscopy, luminometry, etc.); fluorescent intensity of one or more bioluminescent proteins and/or fluorescent proteins and/or fusions thereof; pulse-chase analysis (e.g., pulse-labeling a cell with radioactive amino acids and following the decay of the labeled protein while chasing with unlabeled precursor, and arresting protein synthesis and measuring the decay of total protein levels with time); cyclohex-imide-chase assays;

In some embodiments, an assay can be used to detect peptide degradation, wherein a sample is contacted with a non-fluorescent compound that is operable to react with free primary amine in said sample produced via the degradation of a peptide, and which then produces a fluorescent signal that can be quantified and compared to a standard. Examples of non-fluorescent compounds that can be utilized as fluorescent tags for free amines according to the present disclosure are 3-(4-carboxybenzoyl) quinoline-2-carboxaldehyde (CBQCA), fluorescamine, and o-phthaldialdehyde.

In some embodiments, the method to determine the readout signal from the reporter protein depends from the nature of the reporter protein. For example, for fluorescent reporter proteins, the readout signal corresponds to the intensity of the fluorescent signal. The readout signal may be measured using spectroscopy-, fluorometry-, photometry-, and/or luminometry-based methods and detection systems, for example. Such methods and detection systems are well known in the art.

In some embodiments, standard immunological procedures known to those having ordinary skill in the art can be used to detect peptide degradation. For example, in some embodiments, peptide degradation can be detected in a sample using immunoassays that employ a detectable antibody. Such immunoassays include, for example, agglutination assays, ELISA, Pandex microfluorimetric assay, flow cytometry, serum diagnostic assays, and immunohistochemical staining procedures, all of which are well-known in the art. In some embodiments, the levels (e.g., of fluorescence) in one sample can be compared to a standard. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Exemplary methods of detecting peptide degradation is provided in U.S. Pat. Nos. 5,766,927; 7,504,253; 9,201,073; 9,429,566; United States Patent Application 20120028286; Eldeeb et al., A molecular toolbox for studying protein degradation in mammalian cells. J Neurochem. 2019 November; 151(4):520-533; and Buchanan et al., Cyclohex-imide Chase Analysis of Protein Degradation in *Saccharomyces cerevisiae*. J Vis Exp. 2016; (110): 53975, the disclosures of which are incorporated herein by reference in their entireties.

Agriculturally Acceptable Salts

As used herein, the term "pharmaceutically acceptable salt" and "agriculturally acceptable salt" are synonymous.

In some embodiments, agriculturally acceptable salts, hydrates, solvates, crystal forms and individual isomers, enantiomers, tautomers, diastereomers and prodrugs of the NVP described herein can be utilized.

In some embodiments, an agriculturally acceptable salt of the present disclosure possesses the desired pharmacological activity of the parent compound. Such salts include: acid addition salts, formed with inorganic acids; acid addition salts formed with organic acids; or salts formed when an acidic proton present in the parent compound is replaced by a metal ion, e.g., an alkali metal ion, aluminum ion; or coordinates with an organic base such as ethanolamine, and the like.

In some embodiments, agriculturally acceptable salts include conventional toxic or non-toxic salts. For example, in some embodiments, convention non-toxic salts include those such as fumarate, phosphate, citrate, chlorydrate, and the like. In some embodiments, the agriculturally acceptable salts of the present disclosure can be synthesized from a parent compound by conventional chemical methods. In some embodiments, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by reference in its entirety.

In some embodiments, an agriculturally acceptable salt can be one of the following: hydrochloride; sodium; sulfate; acetate; phosphate or diphosphate; chloride; potassium; maleate; calcium; citrate; mesylate; nitrate; tartrate; aluminum; or gluconate.

In some embodiments, a list of agriculturally acceptable acids that can be used to form salts can be: glycolic acid; hippuric acid; hydrobromic acid; hydrochloric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); undecylenic acid; a 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; or glycerophosphoric acid.

In some embodiments, agriculturally acceptable salt can be any organic or inorganic addition salt.

In some embodiments, the salt may use an inorganic acid and an organic acid as a free acid. The inorganic acid may be hydrochloric acid, bromic acid, nitric acid, sulfuric acid, perchloric acid, phosphoric acid, etc. The organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, malonic acid, etc.

In some embodiments, the salts include alkali metal salts (sodium salts, potassium salts, etc.) and alkaline earth metal salts (calcium salts, magnesium salts, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc., and among them, hydrochloride or trifluoroacetate may be used.

In yet other embodiments, the agriculturally acceptable salt can be a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

In some embodiments, the agriculturally acceptable salt can be prepared from either inorganic or organic bases. Salts derived from inorganic bases include, but are not limited to, the sodium, potassium, lithium, ammonium, calcium, magnesium, ferrous, zinc, copper, manganous, aluminum, ferric, manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

In some embodiments, agriculturally acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Agriculturally acceptable salts are well known in the art. For example, S. M. Berge, et al. describe agriculturally acceptable salts in detail in J. Pharmaceutical Sciences, 66: 1-19 (1977), the disclosure of which is incorporated herein by reference in its entirety.

In some embodiments, the salts of the present disclosure can be prepared in situ during the final isolation and purification of the compounds of the invention, or separately by reacting the free base function with a suitable organic acid. Examples of agriculturally acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other agriculturally acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further agriculturally acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Exemplary descriptions of pharmaceutically acceptable salts is provided in P. H. Stahl and C. G. Wermuth, (editors), *Handbook of Pharmaceutical Salts: Properties, Selection and Use*, John Wiley & Sons, Aug. 23, (2002), the disclosure of which is incorporated herein by reference in its entirety.

NVP Incorporation into Plants or Parts Thereof

The NVPs described herein, and/or an antimicrobial protein comprising at least one NVP as described herein, can be incorporated into plants, plant tissues, plant cells, plant seeds, and/or plant parts thereof, for either the stable, or transient expression of an NVP or an NVP-antimicrobial protein, and/or a polynucleotide sequence encoding the same.

In some embodiments, the NVP or NVP-antimicrobial protein can be incorporated into a plant using recombinant techniques known in the art. In some embodiments, the NVP or NVP-antimicrobial protein may be in the form of an antimicrobial protein which may comprise one or more NVP monomers.

As used herein, with respect to transgenic plants, plant tissues, plant cells, and plant seeds, the term "NVP" also encompasses an NVP-antimicrobial protein, and a "NVP polynucleotide" is similarly also used to encompass a polynucleotide or group of polynucleotides operable to express and/or encode an antimicrobial protein comprising one or more NVPs.

The goal of incorporating an NVP into plants is to deliver NVPs and/or NVP-antimicrobial proteins to the pathogenic microbe via the microbe's consumption of the transgenic NVP expressed in a plant tissue consumed by the microbe. Upon the consumption of the NVP by the microbe from its food (e.g., via an microbe feeding upon a transgenic plant transformed with an NVP), the consumed NVP may have the ability to inhibit the growth, impair the movement, or even kill an microbe. Accordingly, transgenic plants expressing an NVP polynucleotide and/or an NVP polypeptide may express said NVP polynucleotide/polypeptide in a variety of plant tissues, including but not limited to: the epidermis (e.g., mesophyll); periderm; phloem; xylem; parenchyma; collenchyma; sclerenchyma; and primary and secondary meristematic tissues. For example, in some embodiments, a polynucleotide sequence encoding an NVP can be operably linked to a regulatory region containing a phosphoenolpyruvate carboxylase promoter, resulting in the expression of an NVP in a plant's mesophyll tissue.

Transgenic plants expressing an NVP and/or a polynucleotide operable to express NVP can be generated by any one of the various methods and protocols well known to those having ordinary skill in the art; such methods of the invention do not require that a particular method for introducing a nucleotide construct to a plant be used, only that the nucleotide construct gains access to the interior of at least one cell of the plant. Methods for introducing nucleotide constructs into plants are known in the art including, but not limited to, stable transformation methods, transient transformation methods, and virus-mediated methods. "Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. Typically, a construct that expresses an exogenous or heterologous peptide or polypeptide of interest (e.g., an NVP), would contain a promoter to drive transcription of the gene, as well as a 3' untranslated region to allow transcription termination and polyadenylation. The design and organization of such constructs is well known in the art. In some embodiments, a gene can be engineered such that the resulting peptide is secreted, or otherwise targeted within the plant cell to a specific region and/or organelle. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically, a plant expression cassette can be inserted into a plant transformation vector. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the NVP are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) Trends in Plant Science 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) The Plant Journal 6:271-282; Ishida et al. (1996) Nature Biotechnology 14:745-750). Explants are typically transferred to a fresh supply of the same medium and cultured routinely. A general description of the techniques and methods for generating transgenic plants are found in Ayres and Park (1994) Critical Reviews in Plant Science 13:219-239 and Bommineni and Jauhar (1997) Maydica 42:107-120. Because the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation, Lec transformation, and various other non-particle direct-mediated methods to transfer DNA. Exemplary transformation protocols are disclosed in U.S. Published Application No. 20010026941; U.S. Pat. No. 4,945,050; International Publication No. WO 91/00915; and U.S. Published Application No. 2002015066, the disclosures of which are incorporated herein by reference in their entireties.

Chloroplasts can also be readily transformed, and methods concerning the transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606, the disclosure of which is incorporated herein by reference in its entirety. The method of chloroplast transformation relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

Following integration of heterologous foreign DNA into plant cells, one having ordinary skill may then apply a maximum threshold level of appropriate selection chemical/reagent (e.g., an antibiotic) in the medium to kill the untransformed cells, and separate and grow the putatively transformed cells that survive from this selection treatment by transferring said surviving cells regularly to a fresh medium. By continuous passage and challenge with appropriate selection, an artisan identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional methods known to those having ordinary skill in the art. See, for example, McCormick et al. (1986) Plant Cell Reports 5:81-84, the disclosure of which is incorporated herein by reference in its entirety. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the invention, for example, an expression cassette of the invention, stably incorporated into their genome.

In various embodiments, the present disclosure provides an NVP-antimicrobial protein, that act as substrates for microbe proteinases, proteases and peptidases (collectively referred to herein as "proteases") as described above.

In some embodiments, transgenic plants or parts thereof, that may be receptive to the expression of NVPs can include: alfalfa, banana, barley, bean, broccoli, cabbage, canola, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and a wheat plant.

In some embodiments the transgenic plant may be grown from cells that were initially transformed with the DNA constructs described herein. In other embodiments, the transgenic plant may express the encoded NVP in a specific tissue, or plant part, for example, a leaf, a stem a flower, a sepal, a fruit, a root, a seed, or combinations thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; wherein the amino acid is a natural amino acid; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; wherein the amino acid is V, L, I, M, F, W, P, S, T, Y, N, Q, D, E, K, R, or H; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; wherein the amino acid is L, M, F, W, S, Y, D, or E; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; wherein the amino acid is L or W; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: V, L, I, M, F, W, P, S, T, Y, N, Q, D, E, K, R, or H; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L, M, F, W, S, Y, D, or E; or a complementary nucleotide sequence thereof.

In some embodiments, the plant, plant tissue, plant cell, plant seed, or part thereof, can be transformed with an NVP or a polynucleotide encoding the same, wherein the NVP has the amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L or W; or a complementary nucleotide sequence thereof.

In some embodiments, the plant, plant tissue, plant cell, or plant seed can be transformed with an NVP that comprises, consists essentially of, or consists of, an amino sequence as set forth in any one of SEQ ID NOs: 4-19, or 66.

In some embodiments, the plant, plant tissue, plant cell, or plant seed can be transformed with an NVP that comprises, consists essentially of, or consists of, an amino sequence as set forth in any one of SEQ ID NOs: 5, 7, 8, 9, 11, 13, 16, and 17.

In some embodiments, the plant, plant tissue, plant cell, plant seed, or part thereof, can be transformed with an NVP or a polynucleotide encoding the same, wherein the polynucleotide is operable to encode a homopolymer or heteropolymer of two or more NVPs, wherein the amino acid sequence of each NVP is the same or different.

In some embodiments, the plant, plant tissue, plant cell, plant seed, or part thereof, can be transformed with an NVP or a polynucleotide encoding the same, wherein the polynucleotide is operable to encode an NVP that is a fused protein comprising two or more NVPs separated by a cleavable or non-cleavable linker, and wherein the amino acid sequence of each NVP may be the same or different.

In some embodiments, the linker is a cleavable linker.

In some embodiments, the linker has an amino acid sequence as set forth in any one of SEQ ID NOs: 39-51.

In some embodiments, the linker is cleavable inside at least one of (i) the gut or hemolymph of an invertebrate, and (ii) cleavable inside the gut of a mammal.

In some embodiments, the plant, plant tissue, plant cell, or plant seed can be transformed with an NVP wherein the NVP has an amino acid sequence of any of the aforementioned NVPs (e.g., one or more the NVPs enumerated in Table 1), or a polynucleotide encoding the same.

In some embodiments, the plant, plant tissue, plant cell, or plant seed can be transformed with an NVP having an amino acid sequence selected from the group consisting of SEQ NOs: 4-19, or 66, or a polynucleotide encoding the same.

In some embodiments, the plant, plant tissue, plant cell, or plant seed can be transformed with an NVP having an amino acid sequence selected from the group consisting of SEQ NOs: 5, 7, 8, 9, 11, 13, 16, and 17, or a polynucleotide encoding the same.

In some embodiments, the plant, plant tissue, plant cell, or plant seed can be transformed with an NVP wherein the NVP is a homopolymer or heteropolymer of two or more NVP polypeptides, wherein the amino acid sequence of each NVP is the same or different, or a polynucleotide encoding the same.

Any of the aforementioned methods, and/or any of the methods described herein, can be used to incorporate one or more of the NVPs or NVP-antimicrobial proteins as described herein, into plants or plant parts thereof. For example, any of the methods described herein can be used to incorporate into plants one or more of the NVPs described in the present disclosure, e.g., NVPs having the amino acid sequence of SEQ ID NOs: 4-19, or 66, which are likewise described herein.

Polynucleotide Incorporation into Plants, the Proteins Expressed Therefrom

A challenge regarding the expression of heterogeneous polypeptides in transgenic plants is maintaining the desired effect (e.g., antimicrobial activity) of the introduced polypeptide upon expression in the host organism; one way to maintain such an effect is to increase the chance of proper protein folding through the use of an operably linked Endoplasmic Reticulum Signal Peptide (ERSP). Another method to maintain the effect of a transgenic protein is to incorporate a Translational Stabilizing Protein (STA).

Plants can be transiently or stably transfected with the DNA sequence that encodes an NVP or an NVP-antimicrobial protein comprising one or more NVPs, using any of the transfection methods described above. Alternatively, plants can be transfected with a polynucleotide that encodes an NVP, wherein said NVP is operably linked to a polynucleotide operable to encode an Endoplasmic Reticulum Signal Peptide (ERSP); linker, Translational Stabilizing Protein (STA); or combination thereof. For example, in some embodiments, a transgenic plant or plant genome can be transformed with a polynucleotide sequence that encodes the Endoplasmic Reticulum Signal Peptide (ERSP); NVP; and/or intervening linker peptide (LINKER or L), thus causing mRNA transcribed from the heterogeneous DNA to be expressed in the transformed plant, and subsequently, said mRNA to be translated into a peptide.

Endoplasmic Reticulum Signal Peptide (ERSP)

The subcellular targeting of a recombinant protein to the ER can be achieved through the use of an ERSP operably linked to said recombinant protein; this allows for the correct assembly and/or folding of such proteins, and the high level accumulation of these recombinant proteins in plants. Exemplary methods concerning the compartmentalization of host proteins into intracellular storage are disclosed in McCormick et al., Proc. Natl. Acad. Sci. USA 96(2):703-708, 1999; Staub et al., Nature Biotechnology 18:333-338, 2000; Conrad et al., Plant Mol. Biol. 38:101-109, 1998; and Stoger et al., Plant Mol. Biol. 42:583-590, 2000, the disclosures of which are incorporated herein by reference in their entireties. Accordingly, one way to achieve the correct assembly and/or folding of recombinant proteins, is to operably link an endoplasmic reticulum signal peptide (ERSP) to the recombinant protein of interest.

In some embodiments, a peptide comprising an Endoplasmic Reticulum Signal Peptide (ERSP) can be operably linked to an NVP (designated as ERSP-NVP), wherein said ERSP is the N-terminal of said peptide. In some embodiments, the ERSP peptide is between 3 to 60 amino acids in length, between 5 to 50 amino acids in length, between 20 to 30 amino acids in length.

In some embodiments, NVP ORF starts with an ersp at its 5'-end. For the NVP to be properly folded and functional when it is expressed from a transgenic plant, it must have an ersp nucleotide fused in frame with the polynucleotide encoding an NVP. During the cellular translation process, translated ERSP can direct the NVP being translated to insert into the Endoplasmic Reticulum (ER) of the plant cell by binding with a cellular component called a signal-recognition particle. Within the ER the ERSP peptide is cleaved by signal peptidase and the NVP is released into the ER, where the NVP is properly folded during the post-translation modification process, for example, the formation of disulfide bonds. Without any additional retention protein signals, the protein is transported through the ER to the Golgi apparatus, where it is finally secreted outside the plasma membrane and into the apoplastic space. NVP can accumulate at apoplastic space efficiently to reach the antimicrobial dose in plants.

The ERSP peptide is at the N-terminal region of the plant-translated NVP complex and the ERSP portion is composed of about 3 to 60 amino acids. In some embodiments it is 5 to 50 amino acids. In some embodiments it is 10 to 40 amino acids but most often is composed of 15 to 20; 20 to 25; or 25 to 30 amino acids. The ERSP is a signal peptide so called because it directs the transportation of a protein. Signal peptides may also be called targeting signals, signal sequences, transit peptides, or localization signals. The signal peptides for ER trafficking are often 15 to 30 amino acid residues in length and have a tripartite organization, comprised of a core of hydrophobic residues flanked by a positively charged amino terminal and a polar, but uncharged carboxyterminal region. (Zimmermann, et al, "Protein translocation across the ER membrane," Biochimica et Biohysica Acta, 2011, 1808: 912-924).

Many ERSPs are known. It is NOT required that the ERSP be derived from a plant ERSP, non-plant ERSPs will work with the procedures described herein. Many plant ERSPs are however well known and we describe some plant derived ERSPs here. For example, ins some embodiments, the ERSP can be a barley alpha-amylase signal peptide (BAAS), which is derived from the plant, *Hordeum vulgare*, and has an amino acid sequence as follows: "MANKHLSLSLFLVLLGLSASLASG" (SEQ ID NO:52)

Plant ERSPs, which are selected from the genomic sequence for proteins that are known to be expressed and released into the apoplastic space of plants, include examples such as BAAS, carrot extensin, and tobacco PR1. The following references provide further descriptions, and are incorporated by reference herein in their entirety: De Loose, M. et al. "The extensin signal peptide allows secretion of a heterologous protein from protoplasts" Gene, 99 (1991) 95-100; De Loose, M. et al. described the structural analysis of an extension—encoding gene from *Nicotiana plumbaginfolia*, the sequence of which contains a typical signal peptide for translocation of the protein to the endoplasmic reticulum; Chen, M. H. et al. "Signal peptide-dependent targeting of a rice alpha-amylase and cargo proteins to plastids and extracellular compartments of plant cells" Plant Physiology, 2004 July; 135(3): 1367-77. Epub 2004 Jul. 2. Chen, M. H. et al. studied the subcellular localization of α-amylases in plant cells by analyzing the expression of α-amylase, with and without its signal peptide, in transgenic tobacco. These references and others teach and disclose the signal peptide that can be used in the methods, procedures and peptide, protein and nucleotide complexes and constructs described herein.

In some embodiments, the ERSP can include, but is not limited to, one of the following: a BAAS; a tobacco extensin signal peptide; a modified tobacco extensin signal peptide; or a Jun a 3 signal peptide from *Juniperus ashei*. For example, in some embodiments, a plant can be transformed with a nucleotide that encodes any of the peptides that are described herein as Endoplasmic Reticulum Signal Peptides (ERSP), and an NVP.

The tobacco extensin signal peptide motif is another exemplary type of ERSP. See Memelink et al, the Plant Journal, 1993, V4: 1011-1022; Pogue G P et al, Plant Biotechnology Journal, 2010, V8: 638-654, the disclosures of which are incorporated herein by reference in their entireties.

In some embodiments, an NVP ORF can have a nucleotide sequence operable to encode a tobacco extensin signal peptide motif. In one embodiment, the NVP ORF can encode an extensin motif according to SEQ ID NO:53. In another embodiment, the NVP ORF can encode an extensin motif according to SEQ ID NO:54.

An illustrative example of how to generate an embodiment with an extensin signal motif is as follows: A DNA sequence encoding an extensin motif is designed (for example, the DNA sequence shown in SEQ ID NO:55 or SEQ ID NO:56) using oligo extension PCR with four synthetic DNA primers; ends sites such as a restriction site, for example, a Pac I restriction site at the 5'-end, and a 5'-end of a GFP sequence at the 3'-end, can be added using PCR with the extensin DNA sequence serving as a template, and resulting in a fragment; the fragment is used as the forward PCR primer to amplify the DNA sequence encoding an NVP ORF, for example "gfp-l-nvp" contained in a pFECT vector, thus producing an NVP ORF encoding (from N' to C' terminal) "ERSP-GFP-L-NVP" wherein the ERSP is extensin. The resulting DNA sequence can then be cloned into Pac I and Avr II restriction sites of a FECT vector to generate the pFECT-NVP vector for transient plant expression of GFP fused NVP.

In some embodiments, an illustrative expression system can include the FECT expression vectors containing NVP ORF is transformed into *Agrobacterium*, GV3101, and the transformed GV3101 is injected into tobacco leaves for transient expression of NVP ORF.

Translational Stabilizing Protein (STA)

A Translational stabilizing protein (STA) can increase the amount of NVP in plant tissues. One of the NVP ORFs, i.e., ERSP-NVP, may be sufficient to express a properly folded NVP in the transfected plant; however, in some embodiments, effective protection of a plant from pathogenic microbe damage may require that the plant expressed NVP accumulate. With transfection of a properly constructed NVP ORF, a transgenic plant can express and accumulate greater amounts of the correctly folded NVP. When a plant accumulates greater amounts of properly folded NVP, it can more easily resist, inhibit, and/or kill the pathogenic microbes that attack and eat the plants. One method of increasing the accumulation of a polypeptide in transgenic tissues is through the use of a translational stabilizing protein (STA). The translational stabilizing protein can be used to significantly increase the accumulation of NVP in plant tissue, and thus increase the efficacy of a plant transfected with NVP with regard to pathogenic microbe resistance. The translational stabilizing protein is a protein with sufficient tertiary structure that it can accumulate in a cell without being targeted by the cellular process of protein degradation.

In some embodiments, the translational stabilizing protein can be a domain of another protein, or it can comprise an entire protein sequence. In some embodiments, the translational stabilizing protein can be between 5 and 50 amino acids, 50 to 250 amino acids (e.g., GNA), 250 to 750 amino acids (e.g., chitinase) and 750 to 1500 amino acids (e.g., enhancin).

One embodiment of the translational stabilizing protein can be a polymer of fusion proteins comprising at least one NVP. A specific example of a translational stabilizing protein is provided here to illustrate the use of a translational stabilizing protein. The example is not intended to limit the disclosure or claims in any way. Useful translational stabilizing proteins are well known in the art, and any proteins of this type could be used as disclosed herein. Procedures for evaluating and testing production of peptides are both known in the art and described herein. One example of one translational stabilizing protein is Green-Fluorescent Protein (GFP) (SEQ ID NO:57; NCBI Accession No. P42212.1).

In some embodiments, a protein comprising an Endoplasmic Reticulum Signal Peptide (ERSP) can be operably linked to an NVP, which is in turn operably linked to a Translational Stabilizing Protein (STA). Here, this configuration is designated as ERSP-STA-NVP or ERSP-NVP-STA, wherein said ERSP is the N-terminal of said protein and said STA may be either on the N-terminal side (upstream) of the NVP, or of the C-terminal side (downstream) of the NVP. In some embodiments, a protein designated as ERSP-STA-NVP or ERSP-NVP-STA, comprising any of the ERSPs or NVPs described herein, can be operably linked to a STA, for example, any of the translational stabilizing proteins described, or taught by this document including GFP (Green Fluorescent Protein; SEQ ID NO:57; NCBI Accession No. P42212), or Jun a 3, (*Juniperus ashei*; SEQ ID NO:58; NCBI Accession No. P81295.1).

Additional examples of translational stabilizing proteins can be found in the following references, the disclosures of which are incorporated herein by reference in their entirety: Kramer, K. J. et al. "Sequence of a cDNA and expression of the gene encoding epidermal and gut chitinases of Manduca sexta" Insect Biochemistry and Molecular Biology, Vol. 23, Issue 6, September 1993, pp. 691-701. Kramer, K. J. et al. isolated and sequenced a chitinase-encoding cDNA from the tobacco hornworm, Manduca sexta. Hashimoto, Y. et al. "Location and nucleotide sequence of the gene encoding the viral enhancing factor of the *Trichoplusia ni granulosis* virus" Journal of General Virology, (1991), 72, 2645-2651. These references and others teach and disclose translational stabilizing proteins that can be used in the methods, procedures and peptide, protein and nucleotide complexes and constructs described herein.

In some embodiments, an NVP ORF can be transformed into a plant, for example, in the tobacco plant, *Nicotiana benthamiana*, using an NVP ORF that contains a STA. For example, in some embodiments, the STA can be Jun a 3. The mature Jun a 3 is a ~30 kDa plant defending protein that is also an allergen for some people. Jun a 3 is produced by *Juniperus ashei* trees and can be used in some embodiments as a translational stabilizing protein (STA). In some embodiments, the Jun a 3 amino acid sequence can be the sequence shown in SEQ ID NO:58. In other embodiments, the Jun a 3 amino acid sequence can be the sequence shown in SEQ ID NO:59.

Linkers

Linker proteins assist in the proper folding of the different motifs composing an NVP ORF. The NVP ORF described in this invention also incorporates polynucleotide sequences encoding intervening linker peptides between the polynucleotide sequences encoding the NVP (nvp) and the translational stabilizing protein (sta), or between polynucleotide sequence encoding multiple polynucleotide sequences encoding NVP, i.e., $(l\text{-nvp})_N$ or $(nvp\text{-}l)_N$, if the expression ORF involves multiple NVP domain expression. The intervening linker peptides (LINKERS or L or $Li_{INK}$) separate the different parts of the expressed NVP construct, and help proper folding of the different parts of the complex during the expression process. In the expressed NVP construct, different intervening linker peptides can be involved to separate different functional domains. In some embodiments, the LINKER is attached to an NVP and this bivalent group can be repeated up to 10 (N=1-10) and possibly even more than 10 times (e.g., N=200) in order to facilitate the accumulation of properly folded NVP in the plant that is to be protected.

In some embodiments the intervening linker peptide can be between 1 and 30 amino acids in length. However, it is not necessarily an essential component in the expressed NVP in plants.

In some embodiments, the NVP-antimicrobial protein comprises at least one NVP operably linked to a cleavable peptide. In other embodiments, the NVP-antimicrobial protein comprises at least one NVP operably linked to a non-cleavable peptide.

A cleavable linker peptide can be designed to the NVP ORF to release the properly NVP from the expressed NVP complex in the transformed plant to improve the protection the NVP affords the plant with regard to pathogenic microbe damage. One type of the intervening linker peptide is the plant cleavable linker peptide. This type of linker peptides can be completely removed from the expressed NVP ORF complex during plant post-translational modification. Therefore, in some embodiments, the properly folded NVP linked by this type of intervening linker peptides can be released in the plant cells from the expressed NVP ORF complex during post-translational modification in the plant.

In some embodiments, the NVP ORF can contain a cleavable type of intervening linker, for example, the type listed in SEQ ID NO:39, having the amino acid code of "IGER" (SEQ ID NO:39). The molecular weight of this intervening linker or LINKER is 473.53 Daltons. In other embodiments, the intervening linker peptide (LINKER) can also be one without any type of protease cleavage site, i.e., an uncleavable intervening linker peptide, for example, the linker "EEKKN" (SEQ ID NO: 40) or "ETMFKHGL" (SEQ ID NO:41).

In some embodiments, the NVP-antimicrobial protein can have two or more cleavable peptides, wherein the antimicrobial protein comprises an microbe cleavable linker (L), the microbe cleavable linker being fused in frame with a construct comprising $(NVP-L)_n$, wherein "n" is an integer ranging from 1 to 200, or from 1 to 100, or from 1 to 10. In another embodiment, the NVP-antimicrobial protein, and described herein, comprises an endoplasmic reticulum signal peptide (ERSP) operably linked with an NVP, which is operably linked with an microbe cleavable linker (L) and/or a repeat construct $(L-NVP)_n$ or $(NVP-L)_n$, wherein n is an integer ranging from 1 to 200, or from 1 to 100, or from 1 to 10.

In some embodiments, a protein comprising an Endoplasmic Reticulum Signal Peptide (ERSP) can be operably linked to an NVP and an intervening linker peptide (L or Linker); such a construct is designated as ERSP-L-NVP, or ERSP-NVP-L, wherein said ERSP is the N-terminal of said protein, and said L or Linker may be either on the N-terminal side (upstream) of the NVP, or the C-terminal side (downstream) of the NVP. A protein designated as ERSP-L-NVP, or ERSP-NVP-L, comprising any of the ERSPs or NVPs described herein, can have a Linker "L" that can be an uncleavable linker peptide, or a cleavable linker peptide, and which may be cleavable in a plant cells during protein expression process.

In some embodiments, an NVP-antimicrobial protein can comprise any of the intervening linker peptides (LINKER or L) described herein, or taught by this document, including but not limited to following sequences: IGER (SEQ ID NO:39), EEKKN, (SEQ ID NO:40), and ETMFKHGL (SEQ ID NO:41), or combinations thereof.

In some embodiments, the linker can be one or more of the following: ALKFLV (SEQ ID NO: 42), ALKLFV (SEQ ID NO: 43), IFVRLR (SEQ ID NO: 44), LFAAPF (SEQ ID NO: 45), ALKFLVGS (SEQ ID NO: 46), ALKLFVGS (SEQ ID NO: 47), IFVRLRGS (SEQ ID NO: 48), LFAAPFGS (SEQ ID NO: 49), LFVRLRGS (SEQ ID NO: 50), and/or LGERGS (SEQ ID NO: 51).

In various embodiments, an exemplary antimicrobial protein can include a protein construct comprising: (ERSP)-$(NVP-L)_n$; (ERSP)-(L)-$(NVP-L)_n$; (ERSP)-$(L-NVP)_n$; (ERSP)-$(L-NVP)_n$-(L); wherein n is an integer ranging from 1 to 200 or from 1 to 100, or from 1 to 10. In various related embodiments described above, an NVP is any NVP described herein, L is a non-cleavable or cleavable peptide, and n is an integer ranging from 1 to 200, preferably an integer ranging from 1 to 100, and more preferably an integer ranging from 1 to 10. In some embodiments, the NVP-antimicrobial protein may contain NVP peptides that are the same or different, and microbe cleavable peptides that are the same or different. In some embodiments, the C-terminus NVP is operably linked at its C-terminus with a cleavable peptide. In some embodiments, the N-terminus NVP is operably linked at its N-terminus with a cleavable peptide.

Other examples of intervening linker peptides can be found in the following references, which are incorporated by reference herein in their entirety: a plant expressed serine proteinase inhibitor precursor was found to contain five homogeneous protein inhibitors separated by six same linker peptides, as disclosed in Heath et al. "Characterization of the protease processing sites in a multidomain proteinase inhibitor precursor from *Nicotiana alata*" European Journal of Biochemistry, 1995; 230: 250-257. A comparison of the folding behavior of green fluorescent proteins through six different linkers is explored in Chang, H. C. et al. "De novo folding of GFP fusion proteins: high efficiency in eukaryotes but not in bacteria" Journal of Molecular Biology, 2005 Oct. 21; 353(2): 397-409. An isoform of the human GalNAc-Ts family, GalNAc-T2, was shown to retain its localization and functionality upon expression in *N. benthamiana* plants by Daskalova, S. M. et al. "Engineering of *N. benthamiana* L. plants for production of N-acetylgalactosamine-glycosylated proteins" BMC Biotechnology, 2010 Aug. 24; 10: 62. The ability of endogenous plastid proteins to travel through stromules was shown in Kwok, E. Y. et al. "GFP-labelled Rubisco and aspartate aminotransferase are present in plastid stromules and traffic between plastids" Journal of Experimental Botany, 2004 March; 55(397): 595-604. Epub 2004 Jan. 30. A report on the engineering of the surface of the tobacco mosaic virus (TMV), virion, with a mosquito decapeptide hormone, trypsin-modulating oostatic factor (TMOF) was made by Borovsky, D. et al. "Expression of Aedes trypsin-modulating oostatic factor on the virion of TMV: A potential larvicide" Proc Natl Acad Sci, 2006 Dec. 12; 103(50): 18963-18968. These references and others teach and disclose the intervening linkers that can be used in the methods, procedures and peptide, protein and nucleotide complexes and constructs described herein.

The NVP ORF and NVP Constructs

"NVP ORF" refers to a nucleotide encoding an NVP, and/or one or more stabilizing proteins, secretory signals, or target directing signals, for example, ERSP or STA, and is defined as the nucleotides in the ORF that has the ability to be translated. Thus, a "NVP ORF diagram" refers to the composition of one or more NVP ORFs, as written out in diagram or equation form. For example, a "NVP ORF diagram" can be written out as using acronyms or short-hand references to the DNA segments contained within the expression ORF. Accordingly, in one example, a "NVP ORF diagram" may describe the polynucleotide segments encoding the ERSP, LINKER, STA, and NVP, by diagramming in equation form the DNA segments as "ersp" (i.e., the polynucleotide sequence that encodes the ERSP polypeptide); "linker" or "L" (i.e., the polynucleotide sequence that encodes the LINKER polypeptide); "sta" (i.e., the polynucleotide sequence that encodes the STA polypeptide), and "nvp" (i.e., the polynucleotide sequence encoding an NVP), respectively. An example of an NVP ORF diagram is "ersp-sta-(linker$_i$-nvp$_j$)$_N$," or "ersp-(nvp$_j$-linker$_i$)$_N$-sta" and/or any combination of the DNA segments thereof.

The following equations describe two examples of an NVP ORF that encodes an ERSP, a STA, a linker, and an NVP:

$$\text{ersp-sta-l-nvp or ersp-nvp-l-sta}$$

In some embodiments, the NVP open reading frame (ORF) described herein is a polynucleotide sequence that will enable the plant to express mRNA, which in turn will be translated into peptides that will folded properly, and/or accumulated to such an extent that said proteins provide a dose sufficient to inhibit and/or kill one or more pathogenic microbes. In one embodiment, an example of a protein NVP ORF can be any NVP described herein (nvp), an "ersp" (i.e., the polynucleotide sequence that encodes the ERSP polypeptide) a "linker" (i.e., the polynucleotide sequence that encodes the LINKER polypeptide), a "sta" (i.e., the polynucleotide sequence that encodes the STA polypeptide), or any combination thereof, and can be described in the following equation format:

ersp-sta-(linker$_i$-nvp$_j$)$_n$, or ersp-(nvp$_j$-linker$_i$)$_n$-sta

The foregoing illustrative embodiment of a polynucleotide equation would result in the following protein complex being expressed: ERSP-STA-(LINKER$_i$-NVP$_j$)$_N$, containing four possible peptide components with dash signs to separate each component. The nucleotide component of ersp is a polynucleotide segment encoding a plant endoplasmic reticulum trafficking signal peptide (ERSP). The component of sta is a polynucleotide segment encoding a translation stabilizing protein (STA), which helps the accumulation of the NVP expressed in plants, however, in some embodiments, the inclusion of sta may not be necessary in the NVP ORF. The component of linker$_i$ is a polynucleotide segment encoding an intervening linker peptide (L OR LINKER) to separate the NVP from other components contained in ORF, and from the translation stabilizing protein. The subscript letter "i" indicates that in some embodiments, different types of linker peptides can be used in the NVP ORF. The component "nvp" indicates the polynucleotide segment encoding the NVP. The subscript "j" indicates different polynucleotides may be included in the NVP ORF. For example, in some embodiments, the polynucleotide sequence can encode an NVP with a different amino acid substitution. The subscript "n" as shown in "(linker$_i$-nvp$_j$)$_n$," indicates that the structure of the nucleotide encoding an intervening linker peptide and an NVP can be repeated "n" times in the same open reading frame in the same NVP ORF, where "n" can be any integrate number from 1 to 10; "n" can be from 1 to 10, specifically "n" can be 1, 2, 3, 4, or 5, and in some embodiments "n" is 6, 7, 8, 9 or 10. The repeats may contain polynucleotide segments encoding different intervening linkers (LINKER) and different NVPs. The different polynucleotide segments including the repeats within the same NVP ORF are all within the same translation frame. In some embodiments, the inclusion of a sta polynucleotide in the NVP ORF may not be required. For example, an ersp polynucleotide sequence can be directly be linked to the polynucleotide encoding an NVP variant polynucleotide without a linker.

In the foregoing exemplary equation, the polynucleotide "nvp" encoding the polypeptide "NVP" can be the polynucleotide sequence that encodes any NVP as described herein, e.g., an NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof.

In some embodiments, the nvp polynucleotide, or polynucleotide operable to encode an NVP, or complementary nucleotide sequence thereof, can encode an NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 4-19, or 66.

In some embodiments, the nvp polynucleotide, or polynucleotide operable to encode an NVP, or complementary nucleotide sequence thereof, can encode an NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 5, 7, 8, 9, 11, 13, 16, and 17.

In some embodiments, a polynucleotide is operable to encode an NVP-antimicrobial protein having the following NVP construct orientation and/or arrangement: ERSP-NVP; ERSP-(NVP)$_N$; ERSP-NVP-L; ERSP-(NVP)$_N$-L; ERSP-(NVP-L)$_N$; ERSP-L-NVP; ERSP-L-(NVP)$_N$; ERSP-(L-NVP)$_N$; ERSP-STA-NVP; ERSP-STA-(NVP)$_N$; ERSP-NVP-STA; ERSP-(NVP)$_N$-STA; ERSP-(STA-NVP)$_N$; ERSP-(NVP-STA)$_N$; ERSP-L-NVP-STA; ERSP-L-STA-NVP; ERSP-L-(NVP-STA)$_N$; ERSP-L-(STA-NVP)$_N$; ERSP-L-(NVP)$_N$-STA; ERSP-(L-NVP)$_N$-STA; ERSP-(L-STA-NVP)$_N$; ERSP-(L-NVP-STA)$_N$; ERSP-(L-STA)$_N$-NVP; ERSP-(L-NVP)$_N$-STA; ERSP-STA-L-NVP; ERSP-STA-NVP-L; ERSP-STA-L-(NVP)$_N$; ERSP-(STA-L)$_N$-NVP; ERSP-STA-(L-NVP)$_N$; ERSP-(STA-L-NVP)$_N$; ERSP-STA-(NVP)$_N$-L; ERSP-STA-(NVP-L)$_N$; ERSP-(STA-NVP)$_N$-L; ERSP-(STA-NVP-L)$_N$; ERSP-NVP-L-STA; ERSP-NVP-STA-L; ERSP-(NVP)$_N$-STA-L ERSP-(NVP-L)$_N$-STA; ERSP-(NVP-STA)$_N$-L; ERSP-(NVP-L-STA)$_N$; or ERSP-(NVP-STA-L)$_N$; wherein N is an integer ranging from 1 to 200.

Any of the aforementioned methods, and/or any of the methods described herein, can be used to incorporate into a plant or a plant part thereof, one or more polynucleotides operable to express any one or more of the NVPs or NVP-antimicrobial proteins as described herein; e.g., one or more NVPs or NVP-antimicrobial protein having the amino acid sequence of SEQ ID NOs: 4-19, or 66, which are likewise described herein.

The present disclosure may be used for transformation of any plant species, including, but not limited to, monocots and dicots. Crops for which a transgenic approach or PEP would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

Transforming Plants with Polynucleotides

In some embodiments, the NVP ORFs and NVP constructs described above and herein can be cloned into any plant expression vector for NVP to be expressed in plants, either transiently or stably.

Transient plant expression systems can be used to promptly optimize the structure of the NVP ORF for some specific NVP expression in plants, including the necessity of some components, codon optimization of some components, optimization of the order of each component, etc. A transient plant expression vector is often derived from a plant virus genome. Plant virus vectors provide advantages in quick and high level of foreign gene expression in plant due to the infection nature of plant viruses. The full length of the plant viral genome can be used as a vector, but often a viral component is deleted, for example the coat protein, and transgenic ORFs are subcloned in that place. The NVP ORF can be subcloned into such a site to create a viral vector. These viral vectors can be introduced into plant mechanically since they are infectious themselves, for example through plant wound, spray-on etc. They can also be transfected into plants via agroinfection, by cloning the virus vector into the T-DNA of the crown gall bacterium, *Agrobacterium tumefaciens*, or the hairy root bacterium, *Agrobacterium rhizogenes*. The expression of the NVP in this vector is controlled by the replication of the RNA virus, and the virus translation to mRNA for replication is controlled by a strong viral promoter, for example, 35S promoter from Cauliflower mosaic virus. Viral vectors with NVP ORF are usually cloned into T-DNA region in a binary vector that can replicate itself in both *E. coli* strains and *Agrobacterium* strains. The transient transfection of a plant can be done by infiltration of the plant leaves with the *Agrobacterium* cells which contain the viral vector for NVP expression. In the transient transformed plant, it is common for the foreign protein expression to be ceased in a short period of time due to the post-transcriptional gene silencing (PTGS). Sometimes a PTGS suppressing protein gene is necessary to be co-transformed into the plant transiently with the same type of viral vector that drives the expression of with the NVP ORF. This improves and extends the expression of the NVP in the plant. The most commonly used PTGS suppressing protein is P19 protein discovered from tomato bushy stunt virus (TBSV).

In some embodiments, transient transfection of plants can be achieved by recombining a polynucleotide encoding a NVP with any one of the readily available vectors (see above and described herein), and confirmed, using a marker or signal (e.g., GFP emission). In some embodiments, a transiently transfected plant can be created by recombining a polynucleotide encoding a NVP with a DNA encoding a GFP-Hybrid fusion protein in a vector, and transfection said vector into a plant (e.g., tobacco) using different FECT vectors designed for targeted expression. In some embodiments, a polynucleotide encoding a NVP can be recombined with a pFECT vector for APO (apoplast localization) accumulation; a pFECT vector for CYTO (cytoplasm localization) accumulation; or pFECT with ersp vector for ER (endoplasm reticulum localization) accumulation.

An exemplary transient plant transformation strategy is agroinfection using a plant viral vector due to its high efficiency, ease, and low cost. In some embodiments, a tobacco mosaic virus overexpression system can be used to transiently transform plants with NVP. See TRBO, Lindbo J A, Plant Physiology, 2007, V145: 1232-1240, the disclosure of which is incorporated herein by reference in its entirety.

The TRBO DNA vector has a T-DNA region for agroinfection, which contains a CaMV 35S promoter that drives expression of the tobacco mosaic virus RNA without the gene encoding the viral coating protein. Moreover, this system uses the "disarmed" virus genome, therefore viral plant to plant transmission can be effectively prevented.

In another embodiment, the FECT viral transient plant expression system can be used to transiently transform plants with NVP. See Liu Z & Kearney C M, BMC Biotechnology, 2010, 10:88, the disclosure of which is incorporated herein by reference in its entirety. The FECT vector contains a T-DNA region for agroinfection, which contains a CaMV 35S promoter that drives the expression of the foxtail mosaic virus RNA without the genes encoding the viral coating protein and the triple gene block. Moreover, this system uses the "disarmed" virus genome, therefore viral plant to plant transmission can be effectively prevented. To efficiently express the introduced heterologous gene, the FECT expression system additionally needs to co-express P19, a RNA silencing suppressor protein from tomato bushy stunt virus, to prevent the post-transcriptional gene silencing (PTGS) of the introduced T-DNA (the TRBO expression system does not need co-expression of P19).

In some embodiments, the NVP ORF can be designed to encode a series of translationally fused structural motifs that can be described as follows: N'-ERSP-STA-L-NVP-C' wherein the "N'" and "C'" indicating the N-terminal and C-terminal amino acids, respectively, and the ERSP motif can be the Barley Alpha-Amylase Signal peptide (BAAS) (SEQ ID NO:52); the stabilizing protein (STA) can be GFP (SEQ ID NO:57); the linker peptide "L" can be IGER (SEQ ID NO:39) In some embodiments, the ersp-sta-l-nvp ORF can chemically synthesized to include restrictions sites, for example a Pac I restriction site at its 5'-end, and an Avr II restriction site at its 3'-end. In some embodiments, the NVP ORF can be cloned into the Pac I and Avr II restriction sites of a FECT expression vector (pFECT) to create an NVP expression vector for the FECT transient plant expression system (pFECT-NVP). To maximize expression in the FECT expression system, some embodiments may have a FECT vector expressing the RNA silencing suppressor protein P19 (pFECT-P19) generated for co-transformation.

In some embodiments, a vector can be recombined for use in a TRBO transient plant expression system, for example, by performing a routine PCR procedure and adding a Not I restriction site to the 3'-end of the NVP ORF described above, and then cloning the NVP ORF into Pac I and Not I restriction sites of the TRBO expression vector (pTRBO-NVP).

In some embodiments, an *Agrobacterium tumefaciens* strain, for example, commercially available GV3101 cells, can be used for the transient expression of a NVP ORF in a plant tissue (e.g., tobacco leaves) using one or more transient expression systems, for example, the FECT and TRBO expression systems. An exemplary illustration of such a transient transfection protocol includes the following: an overnight culture of GV3101 can be used to inoculate 200 mL Luria-Bertani (LB) medium; the cells can be allowed to grow to log phase with OD600 between 0.5 and 0.8; the cells can then be pelleted by centrifugation at 5000 rpm for 10 minutes at 4° C.; cells can then be washed once with 10 mL prechilled TE buffer (Tris-HCl 10 mM, EDTA 1 mM, pH8.0), and then resuspended into 20 mL LB medium; GV3101 cell resuspension can then be aliquoted in 250 µL fractions into 1.5 mL microtubes; aliquots can then be snap-frozen in liquid nitrogen and stored at −80° C. freezer for future transformation. The pFECT-NVP and pTRBO-NVP vectors can then transformed into the competent GV3101 cells using a freeze-thaw method as follows: the stored competent GV3101 cells are thawed on ice and mixed with 1 to 5 µg pure DNA (pFECT-NVP or pTRBO-NVP vector). The cell-DNA mixture is kept on ice for 5 minutes, transferred to −80° C. for 5 minutes, and incubated in a 37° C. water bath for 5 minutes. The freeze-thaw treated cells are then diluted into 1 mL LB medium and shaken on a rocking table for 2 to 4 hours at room temperature. A 200 µL aliquot of the cell-DNA mixture is then spread onto LB agar plates with the appropriate antibiotics (10 µg/mL rifampicin, 25 µg/mL gentamycin, and 50 µg/mL kanamycin can be used for both pFECT-NVP transformation and pTRBO-NVP transformation) and incubated at 28° C. for two days. Resulting transformed colonies are then picked and cultured in 6 mL aliquots of LB medium with the appropriate antibiotics for transformed DNA analysis and making glycerol stocks of the transformed GV3101 cells.

In some embodiments, the transient transformation of plant tissues, for example, tobacco leaves, can be performed using leaf injection with a 3-mL syringe without needle. In one illustrative example, the transformed GV3101 cells are streaked onto an LB plate with the appropriate antibiotics (as described above) and incubated at 28° C. for two days. A colony of transformed GV3101 cells are inoculated to 5 ml of LB-MESA medium (LB media supplemented with 10 mM MES, and 20 µM acetosyringone) and the same antibiotics described above, and grown overnight at 28° C. The cells of the overnight culture are collected by centrifugation at 5000 rpm for 10 minutes and resuspended in the induction medium (10 mM MES, 10 mM MgCl$_2$, 100 µM acetosyringone) at a final OD600 of 1.0. The cells are then incubated in the induction medium for 2 hours to overnight at room temperature and are then ready for transient transformation of tobacco leaves. The treated cells can be infiltrated into the underside of attached leaves of *Nicotiana benthamiana* plants by injection, using a 3-mL syringe without a needle attached.

In some embodiments, the transient transformation can be accomplished by transfecting one population of GV3101 cells with pFECT-NVP or pTRBO-NVP and another population with pFECT-P19, mixing the two cell populations together in equal amounts for infiltration of tobacco leaves by injection with a 3-mL syringe.

Stable integration of polynucleotide operable to encode NVP is also possible with the present disclosure, for example, the NVP ORF can also be integrated into plant genome using stable plant transformation technology, and therefore NVPs can be stably expressed in plants and protect the transformed plants from generation to generation. For the stable transformation of plants, the NVP expression vector can be circular or linear. The NVP ORF, the NVP expression cassette, and/or the vector with polynucleotide encoding an NVP for stable plant transformation should be carefully designed for optimal expression in plants based on what is known to those having ordinary skill in the art, and/or by using predictive vector design tools such as Gene Designer 2.0 (Atum Bio); VectorBuilder (Cyagen); Snap-Gene® viewer; GeneArt™ Plasmid Construction Service (Thermo-Fisher Scientific); and/or other commercially available plasmid design services. See Tolmachov, Designing plasmid vectors. Methods Mol Biol. 2009; 542:117-29. The expression of NVP is usually controlled by a promoter that promotes transcription in some, or all the cells of the transgenic plant. The promoter can be a strong plant viral promoter, for example, the constitutive 35S promoter from Cauliflower Mosaic Virus (CaMV); it also can be a strong plant promoter, for example, the hydroperoxide lyase promoter (pHPL) from *Arabidopsis thaliana*; the *Glycine max* polyubiquitin (Gmubi) promoter from soybean; the ubiquitin promoters from different plant species (rice, corn, potato, etc.), etc. A plant transcriptional terminator often occurs after the stop codon of the ORF to halt the RNA polymerase and transcription of the mRNA. To evaluate the NVPs expression, a reporter gene can be included in the NVP expression vector, for example, beta-glucuronidase gene (GUS) for GUS straining assay, green fluorescent protein (GFP) gene for green fluorescence detection under UV light, etc. For selection of transformed plants, a selection marker gene is usually included in the NVP expression vector. In some embodiments, the marker gene expression product can provide the transformed plant with resistance to specific antibiotics, for example, kanamycin, hygromycin, etc., or specific herbicide, for example, glyphosate etc. If agroinfection technology is adopted for plant transformation, T-DNA left border and right border sequences are also included in the NVP expression vector to transport the T-DNA portion into the plant.

The constructed NVP expression vector can be transfected into plant cells or tissues using many transfection technologies. Agroinfection is a very popular way to transform a plant using an *Agrobacterium tumefaciens* strain or an *Agrobacterium rhizogenes* strain. Particle bombardment (also called Gene Gun, or Biolistics) technology is also very common method of plant transfection. Other less common transfection methods include tissue electroporation, silicon carbide whiskers, direct injection of DNA, etc. After transfection, the transfected plant cells or tissues placed on plant regeneration media to regenerate successfully transfected plant cells or tissues into transgenic plants.

Evaluation of a transformed plant can be accomplished at the DNA level, RNA level and protein level. A stably transformed plant can be evaluated at all of these levels and a transiently transformed plant is usually only evaluated at protein level. To ensure that the NVP ORF integrates into the genome of a stably transformed plant, the genomic DNA can be extracted from the stably transformed plant tissues for and analyzed using PCR or Southern blot. The expression of the NVP in the stably transformed plant can be evaluated at the RNA level, for example, by analyzing total mRNA extracted from the transformed plant tissues using northern blot or RT-PCR. The expression of the NVP in the transformed plant can also be evaluated in protein level directly.

There are many ways to evaluate expression of NVP in a transformed plant. If a reporter gene included in the NVP ORF, a reporter gene assay can be performed, for example, in some embodiments a GUS straining assay for GUS reporter gene expression, a green fluorescence detection assay for GFP reporter gene expression, a luciferase assay for luciferase reporter gene expression, and/or other reporter techniques may be employed.

In some embodiments total protein can be extracted from the transformed plant tissues for the direct evaluation of the expression of the NVP using a Bradford assay to evaluate the total protein level in the sample.

In some embodiments, analytical HPLC chromatography technology, Western blot technique, or iELISA assay can be adopted to qualitatively or quantitatively evaluate the NVP in the extracted total protein sample from the transformed plant tissues. NVP expression can also be evaluated by using the extracted total protein sample from the transformed plant tissues in an microbe bioassay, for example, in some embodiments, the transformed plant tissue or the whole transformed plant itself can be used in microbe bioassays to evaluate NVP expression and its ability to provide protection for the plant.

In some embodiments, a plant, plant tissue, plant cell, plant seed, or part thereof of the present disclosure, can comprise one or more NVPs, or a polynucleotide encoding the same, said NVP comprising an amino acid sequence that is at least Confirming Successful Transformation Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformed plant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformed plant, fractionated in a formaldehyde agarose gel, and blotted onto a nylon filter according to standard procedures that are routinely used in the art (Sambrook and Russell, 2001, supra). Expression of RNA encoded by the polynucleotide encoding a NVP is then tested by hybridizing the filter to a radioactive probe derived from a NVP, by methods known in the art (Sambrook and Russell, 2001, supra).

Western blot, biochemical assays and the like may be carried out on the transgenic plants to confirm the presence of protein encoded by the NVP gene by standard procedures (Sambrook and Russell, 2001, supra) using antibodies that bind to one or more epitopes present on the NVP.

A number of markers have been developed to determine the success of plant transformation, for example, resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) J. Biol. Chem. 263:6310-6314 (bromoxynil resistance nitrilase gene); and Sathasivan et al. (1990) Nucl. Acids Res. 18:2188 (AHAS imidazolinone resistance gene). Additionally, the genes disclosed herein are useful as markers to assess transformation of bacterial, yeast, or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pathogenic microbe activity.

Fertile plants expressing a NVP and/or a polynucleotide encoding the same may be tested for pathogenic microbe activity, and the plants showing optimal activity selected for further breeding. Methods are available in the art to assay for pathogenic microbe activity. Generally, the protein is mixed and used in feeding assays. See, for example Marrone et al. (1985) J. of Economic Entomology 78:290-293.

In some embodiments, evaluating the success of a transient transfection procedure can be determined based on the expression of a reporter gene, for example, GFP. In some embodiments, GFP can be detected under UV light in tobacco leaves transformed with the FECT and/or TRBO vectors.

In some embodiments, NVP expression can be quantitatively evaluated in a plant (e.g., tobacco). An exemplary procedure that illustrates NVP quantification in a tobacco plant is as follows: 100 mg disks of transformed leaf tissue is collected by punching leaves with the large opening of a 1000 μL pipette tip. The collected leaf tissue is place into a 2 mL microtube with 5/32" diameter stainless steel grinding balls, and frozen in −80° C. for 1 hour, and then homogenized using a Troemner-Talboys High Throughput Homogenizer. Next, 750 μL ice-cold TSP-SE1 extraction solutions (sodium phosphate solution 50 mM, 1:100 diluted protease inhibitor cocktail, EDTA 1 mM, DIECA 10 mM, PVPP 8%, pH 7.0) is added into the tube and vortexed. The microtube is then left still at room temperature for 15 minutes and then centrifuged at 16,000 g for 15 minutes at 4° C.; 100 μL of the resulting supernatant is taken and loaded into pre-Sephadex G-50-packed column in 0.45 μm Millipore MultiScreen filter microtiter plate with empty receiving Costar microtiter plate on bottom. The microtiter plates are then centrifuged at 800 g for 2 minutes at 4° C. The resulting filtrate solution, herein called total soluble protein extract (TSP extract) of the tobacco leaves, is then ready for the quantitative analysis.

In some embodiments, the total soluble protein concentration of the TSP extract can be estimated using Pierce Coomassie Plus protein assay. BSA protein standards with known concentrations can be used to generate a protein quantification standard curve. For example, 2 μL of each TSP extract can be mixed into 200 μL of the chromogenic reagent (CPPA reagent) of the Coomassie Plus protein assay kits and incubated for 10 minutes. The chromogenic reaction can then be evaluated by reading OD595 using a SpectroMax-M2 plate reader using SoftMax Pro as control software. The concentrations of total soluble proteins can be about 0.788±0.20 μg/μL or about 0.533±0.03 μg/μL in the TSP extract from plants transformed via FECT and TRBO, respectively, and the results can be used to calculate the percentage of the expressed NVP in the TSP (% TSP) for the iELISA assay In some embodiments, an indirect ELISA (iELISA) assay can be used to quantitatively evaluate the NVP content in the tobacco leaves transiently transformed with the FECT and/or TRBO expression systems. An illustrative example of using iELISA to quantify NVP is as follows: 5 μL of the leaf TSP extract is diluted with 95 μL of CB2 solution (Immunochemistry Technologies) in the well of an Immulon 2HD 96-well plate, with serial dilutions performed as necessary; leaf proteins obtained from extract samples are then allowed to coat the well walls for 3 hours in the dark, at room temperature, and the CB2 solution is then subsequently removed; each well is washed twice with 200 μL PBS (Gibco); 150 μL blocking solution (Block BSA in PBS with 5% non-fat dry milk) is added into each well and incubated for 1 hour, in the dark, at room temperature; after the removal of the blocking solution, a PBS wash of the wells, 100 μL of primary antibodies directed against NVP (custom antibodies are commercially available from ProMab Biotechnologies, Inc.; GenScript®; or raised using the knowledge readily available to those having ordinary skill in the art); the antibodies diluted at 1:250 dilution in blocking solution are added to each well and incubated for 1 hour in the dark at room temperature; the primary antibody is removed and each well is washed with PBS 4 times; 100 μL of HRP-conjugated secondary antibody (i.e., antibody directed against host species used to generate primary antibody, used at 1:1000 dilution in the blocking solution) is added into each well and incubated for 1 hour in the dark at room temperature; the secondary antibody is removed and the wells are washed with PBS, 100 μL; substrate solution (a 1:1 mixture of ABTS peroxidase substrate solution A and solution B, KPL) is added to each well, and the chromogenic reaction proceeds until sufficient color development is apparent; 100 μL of peroxidase stop solution is added to each well to stop the reaction; light absorbance of each reaction mixture in the plate is read at 405 nm using a SpectroMax-M2 plate reader, with SoftMax Pro used as control software; serially diluted known concentrations of pure NVPs samples can be treated in the same manner as described above in the iELISA assay to generate a mass-absorbance standard curve for quantities analysis. The expressed NVP can be detected by iELISA at about 3.09±1.83 ng/μL in the leaf TSP extracts from the FECT transformed tobacco; and about 3.56±0.74 ng/μL in the leaf TSP extract from the TRBO transformed tobacco. Alternatively, the expressed NVP can be about 0.40% total soluble protein (% TSP) for FECT transformed plants and about 0.67% TSP in TRBO transformed plants.

Mixtures, Compositions, and Formulations

As used herein, "v/v" or "% v/v" or "volume per volume" refers to the volume concentration of a solution ("v/v" stands for volume per volume). Here, v/v can be used when both components of a solution are liquids. For example, when 50 mL of ingredient X is diluted with 50 mL of water, there will be 50 mL of ingredient X in a total volume of 100 mL; therefore, this can be expressed as "ingredient X 50% v/v." Percent volume per volume (% v/v) is calculated as follows: (volume of solute (mL)/volume of solution (100 mL)); e.g., % v/v=mL of solute/100 mL of solution.

As used herein, "w/w" or "% w/w" or "weight per weight" refers to the weight concentration of a solution, i.e., percent weight in weight ("w/w" stands for weight per weight). Here, w/w expresses the number of grams (g) of a constituent in 100 g of solution or mixture. For example, a mixture consisting of 30 g of ingredient X, and 70 g of water would be expressed as "ingredient X 30% w/w." Percent weight per weight (% w/w) is calculated as follows: (weight of solute (g)/weight of solution (g))×100; or (mass of solute (g)/mass of solution (g))×100.

As used herein, "w/v" or "% w/v" or "weight per volume" refers to the mass concentration of a solution, i.e., percent weight in volume ("w/v" stands for weight per volume). Here, w/v expresses the number of grams (g) of a constituent in 100 mL of solution. For example, if 1 g of ingredient X is used to make up a total volume of 100 mL, then a "1% w/v solution of ingredient X" has been made. Percent weight per volume (% w/v) is calculated as follows: (Mass of solute (g)/Volume of solution (mL))×100.

Any of the NVPs or NVP-antimicrobial proteins described herein (e.g., an NVP having an amino acid sequence as set forth in SEQ ID NOs: 4-19, or 66, or an agriculturally acceptable salt thereof) can be used to create a mixture and/or composition, wherein said mixture and/or composition consists of at least one NVP.

In some embodiments, the present disclosure comprises, consists essentially of, or consists of, a combination, a mixture, or a composition comprising, consisting essentially of, or consisting of, one or more NVPs, one or more NVP-antimicrobial proteins, and/or combinations thereof.

In some embodiments, the invention contemplates a mixture of one or more NVPs, one or more NVP-antimicrobial proteins, and/or combinations thereof. For example, in some embodiments, one or more NVPs, one or more NVP-antimicrobial proteins, and/or combinations thereof, can be blended together in in varying proportions.

In some embodiments, the invention contemplates a combination of one or more NVPs, one or more NVP-antimicrobial proteins, and/or combinations thereof. For example, in some embodiments, one or more NVPs, one or more NVP-antimicrobial proteins, and/or combinations thereof, can be provided as a combination, e.g., in the same container, or in different containers.

In some embodiments, the invention contemplates a composition of one or more NVPs, one or more NVP-antimicrobial proteins, and/or combinations thereof. For example, in some embodiments, one or more NVPs, one or more NVP-antimicrobial proteins, and/or combinations thereof, can be provided as a composition further comprising an excipient.

In some embodiments, the combination, mixture, or composition comprises, consists essentially of, or consists of, an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in Table 1.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or an agriculturally acceptable salt thereof.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is a natural amino acid.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is V, L, I, M, F, W, P, S, T, Y, N, Q, D, E, K, R, or H.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L, M, F, W, S, Y, D, or E.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L or W.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein X₁ is any natural or non-natural amino acid other than glycine or alanine.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): X₁-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein X₁ is a natural amino acid selected from: V, L, I, M, F, W, P, S, T, Y, N, Q, D, E, K, R, or H; or an agriculturally acceptable salt thereof.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): X₁-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein X₁ is a natural amino acid selected from: L, M, F, W, S, Y, D, or E; or an agriculturally acceptable salt thereof.

In some embodiments, the combination, mixture, or composition comprises, consists essentially of, or consists of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): X₁-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein X₁ is a natural amino acid selected from: L or W; or an agriculturally acceptable salt thereof.

In some embodiments, the combination, mixture, or composition comprises, consists essentially of, or consists of, an NVP having an amino sequence as set forth in any one of SEQ ID NOs: 4-19, or 66, or an agriculturally acceptable salt thereof.

In some embodiments, the combination, mixture, or composition comprises, consists essentially of, or consists of, an NVP having an amino sequence as set forth in any one of SEQ ID NOs: 5, 7, 8, 9, 11, 13, 16, and 17, or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "VTKPCQSDKDCKKFACRKPKVPKC-INGFCKCVR" (SEQ ID NO: 4), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "LTKPCQSDKDCKKFACRKPKVPKC-INGFCKCVR" (SEQ ID NO: 5), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ITKPCQSDKDCKKFACRKPKVPKC-INGFCKCVR" (SEQ ID NO: 6), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "MTKPCQSDKDCKKFACRKPKVPKC-INGFCKCVR" (SEQ ID NO: 7), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "FTKPCQSDKDCKKFACRKPKVPKC-INGFCKCVR" (SEQ ID NO: 8), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "WTKPCQSDKDCKKFACRKPKVPKC-INGFCKCVR" (SEQ ID NO: 9), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "PTKPCQSDKDCKKFACRKPKVPKC-INGFCKCVR" (SEQ ID NO: 10), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "STKPCQSDKDCKKFACRKPKVPKC-INGFCKCVR" (SEQ ID NO: 11), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "TTKPCQSDKDCKKFACRKPKVPKC-INGFCKCVR" (SEQ ID NO: 12), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "YTKPCQSDKDCKKFACRKPKVPKC-INGFCKCVR" (SEQ ID NO: 13), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "NTKPCQSDKDCKKFACRKPKVPKC-INGFCKCVR" (SEQ ID NO: 14), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "QTKPCQSDKDCKKFACRKPKVPKC-INGFCKCVR" (SEQ ID NO: 15), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "DTKPCQSDKDCKKFACRKPKVPKC-INGFCKCVR" (SEQ ID NO: 16), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ETKPCQSDKDCKKFACRKPKVPKC-INGFCKCVR" (SEQ ID NO: 17), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KTKPCQSDKDCKKFACRKPKVPKC-INGFCKCVR" (SEQ ID NO: 18), or an agriculturally acceptable salt thereof.

In some embodiments, a combination, mixture, or composition of the present disclosure can comprise, consist essentially of, or consist of, an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "HTKPCQSDKDCKKFACRKPKVPKC-INGFCKCVR" (SEQ ID NO: 19), or an agriculturally acceptable salt thereof.

In some embodiments, a combination, mixture, or composition of the present disclosure can comprise, consist essentially of, or consist of, an NVP, wherein said NVP homopolymer or heteropolymer of two or more NVPs, wherein the amino acid sequence of each NVP is the same or different.

In some embodiments, a combination, mixture, or composition of the present disclosure can comprise, consist essentially of, or consist of, an NVP that is a fused protein comprising two or more NVPs separated by a cleavable or non-cleavable linker, and wherein the amino acid sequence of each NVP may be the same or different.

In some embodiments, a combination, mixture, or composition of the present disclosure can comprise, consist essentially of, or consist of, an NVP having a linker, wherein the linker is a cleavable linker.

In some embodiments, a combination, mixture, or composition of the present disclosure can comprise, consist essentially of, or consist of, an NVP having a linker, wherein the linker has an amino acid sequence as set forth in any one of SEQ ID NOs: 39-51.

In some embodiments, a combination, mixture, or composition of the present disclosure can comprise, consist essentially of, or consist of, an NVP having a linker, wherein the linker is cleavable inside at least one of (i) the gut or hemolymph of an invertebrate, and (ii) cleavable inside the gut of a mammal.

Any of the compositions, products, proteins, polypeptides, peptides, and/or plants transformed with polynucleotides operable to express an NVP, and described herein, can be used to control pathogenic microbes, their growth, and/or the damage caused by their actions, especially their damage to plants.

Compositions comprising an NVP, an NVP-antimicrobial protein, or an agriculturally acceptable salt thereof, for example, agrochemical compositions, can include, but are not limited to, aerosols and/or aerosolized products, e.g., sprays, fumigants, powders, dusts, and/or gases; seed dressings; oral preparations (e.g., microbe food, etc.); transgenic organisms expressing and/or producing an NVP, an NVP-antimicrobial protein, and/or an NVP ORF (either transiently and/or stably), e.g., a plant or an animal.

The composition may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such antimicrobial polypeptide, the polypeptide may be present in a concentration of from about 1% to about 99% by weight.

In some embodiments, the antimicrobial compositions described herein may be made by formulating either the NVP, NVP-antimicrobial protein, or agriculturally acceptable salt thereof, with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the antimicrobial composition with suitable adjuvants using conventional formulation techniques. Suitable formulations and application methods are described in U.S. Pat. No. 6,468,523, the disclosure of which is incorporated by reference herein in its entirety.

In some embodiments, a composition can comprise, consist essentially of, or consist of, an NVP and an excipient.

In some embodiments, a composition can comprise, consist essentially of, or consist of, an NVP-antimicrobial protein and an excipient.

In some embodiments, a composition can comprise, consist essentially of, or consist of, an NVP, an NVP-antimicrobial protein, or an agriculturally acceptable salt thereof, and an excipient.

In some embodiments, a composition of the present disclosure can comprise: an NVP, an NVP-antimicrobial protein, or an agriculturally acceptable salt thereof, and an excipient; wherein the NVP, NVP-antimicrobial protein, or agriculturally acceptable salt thereof is in an amount ranging from about 0.000001% w/w to about 99.99999% w/w of the total composition, or from about 0.01% to about 99.99%; from about 0.02% to about 99.98%; from about 0.03% to about 99.97%; from about 0.04% to about 99.96%; from about 0.05% to about 99.95; from about 0.06% to about 99.94%; from about 0.07% to about 99.93%; from about 0.08% to about 99.92%; from about 0.09% to about 99.91%; from about 1% to about 99%; from about 2% to about 98%; from about 3% to about 97%; from about 4% to about 96%; from about 5% to about 95%; from about 6% to about 94%; from about 7% to about 93%; from about 8% to about 92%; from about 9% to about 91%; from about 10% to about 90%; from about 11% to about 89%; from about 12% to about 88%; from about 13% to about 87%; from about 14% to about 86%; from about 15% to about 85%; from about 16% to about 84%; from about 17% to about 83%; from about 18% to about 82%; from about 19% to about 81%; from about 20% to about 80%; from about 21% to about 79%; from about 22% to about 78%; from about 23% to about 77%; from about 24% to about 76%; from about 25% to about 75%; from about 26% to about 74%; from about 27% to about 73%; from about 28% to about 72%; from about 29% to about 71%; from about 30% to about 70%; from about 31% to about 69%; from about 32% to about 68%; from about 33% to about 67%; from about 34% to about 66%; from about 35% to about 65%; from about 36% to about 64%; from about 37% to about 63%; from about 38% to about 62%; from about 39% to about 61%; from about 40% to about 60%; from about 41% to about 59%; from about 42% to about 58%; from about 43% to about 57%; from about 44% to about 56%; from about 45% to about 55%; from about 46% to about 54%; from about 47% to about 53%; from about 48% to about 52%; from about 49% to about 51%; from about 50% to about 50%; from about 51% to about 49%; from about 52% to about 48%; from about 53% to about 47%; from about 54% to about 46%; from about 55% to about 45%; from about 56% to about 44%; from about 57% to about 43%; from about 58% to about 42%; from about 59% to about 41%; from about 60% to about 40%; from about 61% to about 39%; from about 62% to about 38%; from about 63% to about 37%; from about 64% to about 36%; from about 65% to about 35%; from about 66% to about 34%; from about 67% to about 33%; from about 68% to about 32%; from about 69% to about 31%; from about 70% to about 30%; from about 71% to about 29%; from about 72% to about 28%; from about 73% to about 27%; from about 74% to about 26%; from about 75% to about 25%; from about 76% to about 24%; from about 77% to about 23%; from about 78% to about 22%; from about 79% to about 21%; from about 80% to about 20%; from about 81% to about 19%; from about 82% to about 18%; from about 83% to about 17%; from about 84% to about 16%; from about 85% to about 15%; from about 86% to about 14%; from about 87% to about 13%; from about 88% to about 12%; from about 89% to about 11%; from about 90% to about 10%; from about 91% to about 9%; from about 92% to about 8%; from about 93% to about 7%; from about 94% to about 6%; from about 95% to about 5%; from about 96% to about 4%; from about 97% to about 3%; from about 98% to about 2%; from about 99% to about 1%; from about 99.91 to about 0.09%; from about 99.92 to about 0.08%; from about 99.93 to about 0.07%; from about 99.94 to about 0.06%; from about 99.95 to about 0.05%; from about 99.96 to about 0.04%; from about 99.97 to about 0.03%; from about 99.98 to about 0.02%; or from about 99.99 to about 0.01%, w/w of the total composition.

In some embodiments, a composition of the present disclosure comprises: an NVP, an NVP-antimicrobial protein, or an agriculturally acceptable salt thereof, and an excipient, wherein the concentration of the NVP, NVP-antimicrobial protein, or agriculturally acceptable salt thereof is in an amount of about 0.000001%, 0.00001%, 0.0001%, 0.001%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, 99.9999%, or 99.99999% by weight of the total composition.

In some embodiments, a composition of the present disclosure can comprise: an NVP, an NVP-antimicrobial protein, or an agriculturally acceptable salt thereof, and an excipient; wherein the excipient is in an amount ranging from about 0.000001% w/w to about 99.99999% w/w of the total composition, or from about 0.01% to about 99.99%; from about 0.02% to about 99.98%; from about 0.03% to about 99.97%; from about 0.04% to about 99.96%; from about 0.05% to about 99.95; from about 0.06% to about 99.94%; from about 0.07% to about 99.93%; from about 0.08% to about 99.92%; from about 0.09% to about 99.91%; from about 1% to about 99%; from about 2% to about 98%; from about 3% to about 97%; from about 4% to about 96%; from about 5% to about 95%; from about 6% to about 94%; from about 7% to about 93%; from about 8% to about 92%; from about 9% to about 91%; from about 10% to about 90%; from about 11% to about 89%; from about 12% to about 88%; from about 13% to about 87%; from about 14% to about 86%; from about 15% to about 85%; from about 16% to about 84%; from about 17% to about 83%; from about 18% to about 82%; from about 19% to about 81%; from about 20% to about 80%; from about 21% to about 79%; from about 22% to about 78%; from about 23% to about 77%; from about 24% to about 76%; from about 25% to about 75%; from about 26% to about 74%; from about 27% to about 73%; from about 28% to about 72%; from about 29% to about 71%; from about 30% to about 70%; from about 31% to about 69%; from about 32% to about 68%; from about 33% to about 67%; from about 34% to about 66%; from about 35% to about 65%; from about 36% to about 64%; from about 37% to about 63%; from about 38% to about 62%; from about 39% to about 61%; from about 40% to about 60%; from about 41% to about 59%; from about 42% to about 58%; from about 43% to about 57%; from about 44% to about 56%; from about 45% to about 55%; from about 46% to about 54%; from about 47% to about 53%; from about 48% to about 52%; from about 49% to about 51%; from about 50% to about 50%; from about 51% to about 49%; from about 52% to about 48%; from about 53% to about 47%; from about 54% to about 46%; from about 55% to about 45%; from about 56% to about 44%; from about 57% to about 43%; from about 58% to about 42%; from about 59% to about 41%; from about 60% to about 40%; from about 61% to about 39%; from about 62% to about 38%; from about 63% to about 37%; from about 64% to about 36%; from about 65% to about 35%; from about 66% to about 34%; from about 67% to about 33%; from about 68% to about 32%; from about 69% to about 31%; from about 70% to about 30%; from about 71% to about 29%; from about 72% to about 28%; from about 73% to about 27%; from about 74% to about 26%; from about 75% to about 25%; from about 76% to about 24%; from about 77% to about 23%; from about 78% to about 22%; from about 79% to about 21%; from about 80% to about 20%; from about 81% to about 19%; from about 82% to about 18%; from about 83% to about 17%; from about 84% to about 16%; from about 85% to about 15%; from about 86% to about 14%; from about 87% to about 13%; from about 88% to about 12%; from about 89% to about 11%; from about 90% to about 10%; from about 91% to about 9%; from about 92% to about 8%; from about 93% to about 7%; from about 94% to about 6%; from about 95% to about 5%; from about 96% to about 4%; from about 97% to about 3%; from about 98% to about 2%; from about 99% to about 1%; from about 99.91 to about 0.09%; from about 99.92 to about 0.08%; from about 99.93 to about 0.07%; from about 99.94 to about 0.06%; from about 99.95 to about 0.05%; from about 99.96 to about 0.04%; from about 99.97 to about 0.03%; from about 99.98 to about 0.02%; or from about 99.99 to about 0.01%, w/w of the total composition.

In some embodiments, a composition of the present disclosure comprises: an NVP, an NVP-antimicrobial protein, or an agriculturally acceptable salt thereof, and an excipient, wherein the concentration of the excipient is in an amount of about 0.000001%, 0.00001%, 0.0001%, 0.001%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, %19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999%, 99.9999%, or 99.99999% by weight of the total composition.

Sprayable Compositions

Examples of spray products of the present disclosure can include field sprayable formulations for agricultural usage and indoor sprays for use in interior spaces in a residential or commercial space. In some embodiments, residual sprays or space sprays comprising an NVP, an NVP-antimicrobial protein, or an agriculturally acceptable salt thereof can be used to reduce or eliminate microbe pathogenic microbes in an interior space.

In one embodiment, the composition comprising an NVP, an NVP-antimicrobial protein, or an agriculturally acceptable salt thereof, and an excipient will inhibit microbe pathogenic microbes that come in contact with these surfaces.

In contrast to SSI, which requires that the active NVP or NVP-antimicrobial protein be bound to surfaces of dwellings, such as walls or ceilings, as with a paint, for example, space spray products of the invention rely on the production of a large number of small antimicrobial droplets intended to be distributed through a volume of air over a given period of time. The traditional methods for generating a space-spray include thermal fogging (whereby a dense cloud of a composition comprising an NVP, an NVP-antimicrobial protein, or an agriculturally acceptable salt thereof is produced giving the appearance of a thick fog) and Ultra Low Volume (ULV), whereby droplets are produced by a cold, mechanical aerosol-generating machine. Ready-to-use aerosols such as aerosol cans may also be used.

In some embodiments, a sprayable composition may contain an amount of an NVP, or an agriculturally acceptable salt thereof, ranging from about 0.005 wt % to about 99 wt %.

Foams

The active compositions of the present disclosure comprising an NVP, an NVP-antimicrobial protein, or an agriculturally acceptable salt thereof, and an excipient, may be made available in a spray product as an aerosol-based application, including aerosolized foam applications. Pressurized cans are the typical vehicle for the formation of aerosols. An aerosol propellant that is compatible with the NVP or NVP-antimicrobial protein used. Preferably, a liquefied-gas type propellant is used.

Suitable propellants include compressed air, carbon dioxide, butane and nitrogen. The concentration of the propellant in the active compound composition is from about 5 percent to about 40 percent by weight of the pyridine composition, preferably from about 15 percent to about 30 percent by weight of the comprising an NVP, an NVP-antimicrobial protein, or an agriculturally acceptable salt thereof, and an excipient.

In one embodiment, formulations comprising an NVP, an NVP-antimicrobial protein, or an agriculturally acceptable salt thereof can also include one or more foaming agents. Foaming agents that can be used include sodium laureth sulfate, cocamide DEA, and cocamidopropyl betaine. Preferably, the sodium laureth sulfate, cocamide DEA and cocamidopropyl are used in combination. The concentration of the foaming agent(s) in the active compound composition is from about 10 percent to about 25 percent by weight, more preferably 15 percent to 20 percent by weight of the composition.

When such formulations are used in an aerosol application not containing foaming agents, the active compositions of the present disclosure can be used without the need for mixing directly prior to use. However, aerosol formulations containing the foaming agents do require mixing (i.e., shaking) immediately prior to use. In addition, if the formulations containing foaming agents are used for an extended time, they may require additional mixing at periodic intervals during use.

In some embodiments, an aerosolized foam may contain an amount of an NVP, or an agriculturally acceptable salt thereof, ranging from about 0.005 wt % to about 99 wt %.

Burning Formulations

In some embodiments, a dwelling area may also be treated with an active NVP or NVP-antimicrobial protein composition by using a burning formulation, such as a candle, a smoke coil or a piece of incense containing the composition. For example, the composition may be formulated into household products such as "heated" air fresheners in which antimicrobial compositions are released upon heating, e.g., electrically, or by burning. The active compound compositions of the present disclosure comprising an NVP, an NVP-antimicrobial protein, or an agriculturally acceptable salt thereof may be made available in a spray product as an aerosol, a mosquito coil, and/or a vaporizer or fogger.

In some embodiments, a burning formulation may contain an amount of an NVP, or an agriculturally acceptable salt thereof, ranging from about 0.005 wt % to about 99 wt %.

In some embodiments, a burning formulation may contain an amount of an NVP-antimicrobial protein, or an agriculturally acceptable salt thereof, ranging from about 0.005 wt % to about 99 wt %.

Fabric Treatments

In some embodiments, fabrics and garments may be made containing a antimicrobially effective composition comprising an NVP, an NVP-antimicrobial protein, or an agriculturally acceptable salt thereof, and an excipient. In some embodiments, the concentration of the NVP or NVP-antimicrobial protein in the polymeric material, fiber, yarn, weave, net, or substrate described herein, can be varied within a relatively wide concentration range from, for example, 0.05 to 15 percent by weight, preferably 0.2 to 10 percent by weight, more preferably 0.4 to 8 percent by weight, especially 0.5 to 5, such as 1 to 3, percent by weight.

Similarly, the concentration of the composition comprising an NVP, an NVP-antimicrobial protein, or an agriculturally acceptable salt thereof, and an excipient (whether for treating surfaces or for coating a fiber, yarn, net, weave) can be varied within a relatively wide concentration range from, for example 0.1 to 70 percent by weight, such as 0.5 to 50 percent by weight, preferably 1 to 40 percent by weight, more preferably 5 to 30 percent by weight, especially 10 to 20 percent by weight.

The concentration of the NVP or NVP-antimicrobial protein may be chosen according to the field of application such that the requirements concerning knockdown efficacy, durability and toxicity are met. Adapting the properties of the material can also be accomplished and so custom-tailored textile fabrics are obtainable in this way.

Accordingly, an effective amount of an NVP, an NVP-antimicrobial protein, or an agriculturally acceptable salt thereof can depend on the specific use pattern, the microbe against which control is most desired and the environment in which the NVP or NVP-antimicrobial protein will be used. Therefore, an effective amount of an NVP, an NVP-antimicrobial protein, or an agriculturally acceptable salt thereof is sufficient that control of a microbe is achieved.

In some embodiments, a fabric treatment may contain an amount of an NVP, or an agriculturally acceptable salt thereof, ranging from about 0.005 wt % to about 99 wt %.

In some embodiments, a fabric treatment may contain an amount of an NVP-antimicrobial protein, or an agriculturally acceptable salt thereof, ranging from about 0.005 wt % to about 99 wt %.

Surface-Treatment Compositions

In some embodiments, the present disclosure provides compositions or formulations comprising an NVP and an excipient, or comprising an NVP-antimicrobial protein and an excipient, for coating walls, floors and ceilings inside of buildings, and for coating a substrate or non-living material. The inventive compositions comprising an NVP, an NVP-antimicrobial protein, or an agriculturally acceptable salt thereof, and an excipient, can be prepared using known techniques for the purpose in mind. Preparations of compositions comprising an NVP-antimicrobial protein and an excipient, could be so formulated to also contain a binder to facilitate the binding of the compound to the surface or other substrate. Agents useful for binding are known in the art and tend to be polymeric in form. The type of binder suitable for a compositions to be applied to a wall surface having particular porosities and/or binding characteristics would be different compared to a fiber, yarn, weave or net-thus, a skilled person, based on known teachings, would select a suitable binder based on the desired surface and/or substrate.

Typical binders are poly vinyl alcohol, modified starch, poly vinyl acrylate, polyacrylic, polyvinyl acetate co polymer, polyurethane, and modified vegetable oils. Suitable binders can include latex dispersions derived from a wide variety of polymers and co-polymers and combinations thereof. Suitable latexes for use as binders in the inventive compositions comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes. Also suitable may be a polytetrafluoroethylene (PTFE) polymer for binding the active ingredient to other surfaces.

In some embodiments, a surface-treatment composition may contain an amount of an NVP, or an agriculturally acceptable salt thereof, ranging from about 0.005 wt % to about 99 Wt %.

In some embodiments, a surface-treatment may contain an amount of an NVP-antimicrobial protein, or an agriculturally acceptable salt thereof, ranging from about 0.005 wt % to about 99 wt %.

Dispersants

In some exemplary embodiments, an antimicrobial formulation according to the present disclosure may consist of an NVP, an NVP-antimicrobial protein, or an agriculturally acceptable salt thereof, and an excipient, diluent or carrier (e.g., such as water), a polymeric binder, and/or additional components such as a dispersing agent, a polymerizing agent, an emulsifying agent, a thickener, an alcohol, a fragrance, or any other inert excipients used in the preparation of sprayable compositions known in the art.

In some embodiments, a dispersant may contain an amount of an NVP, or an agriculturally acceptable salt thereof, ranging from about 0.005 wt % to about 99 wt %.

In some embodiments, a dispersant may contain an amount of an NVP-antimicrobial protein, or an agriculturally acceptable salt thereof, ranging from about 0.005 wt % to about 99 wt %.

Suspensions

In some embodiments, a composition comprising an NVP, an NVP-antimicrobial protein, or an agriculturally acceptable salt thereof, and an excipient, can be prepared in a number of different forms or formulation types, such as suspensions or capsules suspensions. And a person skilled in the art can prepare the relevant composition based on the properties of the particular NVP or NVP-antimicrobial protein, its uses, and also its application type. For example, the NVP or NVP-antimicrobial protein used in the methods, embodiments, and other aspects of the present disclosure, may be encapsulated in a suspension or capsule suspension formulation. An encapsulated NVP or NVP-antimicrobial protein can provide improved wash-fastness, and also a longer period of activity. The formulation can be organic based or aqueous based, preferably aqueous based.

In some embodiments, a suspension may contain an amount of an NVP, or an agriculturally acceptable salt thereof, ranging from about 0.005 wt % to about 99 wt %.

In some embodiments, a suspension may contain an amount of an NVP-antimicrobial protein, or an agriculturally acceptable salt thereof, ranging from about 0.005 wt % to about 99 wt %.

Microencapsulation

Microencapsulated NVP or NVP-antimicrobial protein suitable for use in the compositions and methods according to the present disclosure may be prepared with any suitable technique known in the art. For example, various processes for microencapsulating material have been previously developed. These processes can be divided into three categories: physical methods, phase separation, and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the NVP or NVP-antimicrobial protein present in the microcapsules can vary from 0.1 to 60% by weight of the microcapsule.

In some embodiments, a microencapsulation may contain an amount of an NVP, or an agriculturally acceptable salt thereof, ranging from about 0.005 wt % to about 99 wt %.

In some embodiments, a microencapsulation may contain an amount of an NVP-antimicrobial protein, or an agriculturally acceptable salt thereof, ranging from about 0.005 wt % to about 99 wt %.

Formulations, Dispersants, Kits, and the Ingredients Thereof

The formulation used in the compositions (comprising an NVP, an NVP-antimicrobial protein, or an agriculturally acceptable salt thereof, and an excipient), methods, embodiments and other aspects according to the present disclosure, may be formed by mixing all ingredients together with water, and optionally using suitable mixing and/or dispersing aggregates. In general, such a formulation is formed at a temperature of from 10 to 70° C., preferably 15 to 50° C., more preferably 20 to 40° C. Generally, a formulation comprising one or more of (A), (B), (C), and/or (D) is possible, wherein it is possible to use: an NVP, an NVP-antimicrobial protein, or an agriculturally acceptable salt thereof (A); solid polymer (B); optional additional additives (D); and to disperse them in the aqueous component (C). If a binder is present in a composition of the present disclosure (comprising an NVP, an NVP-antimicrobial protein, or an agriculturally acceptable salt thereof, and an excipient), it is preferred to use dispersions of the polymeric binder (B) in water as well as aqueous formulations of the NVP or NVP-antimicrobial protein (A) in water which have been separately prepared before. Such separate formulations may contain additional additives for stabilizing (A) and/or (B) in the respective formulations and are commercially available. In a second process step, such raw formulations and optionally additional water (component (C)) are added. Also, combinations of the abovementioned ingredients based on the foregoing scheme are likewise possible, e.g., using a pre-formed dispersion of (A) and/or (B) and mixing it with solid (A) and/or (B). A dispersion of the polymeric binder (B) may be a pre-manufactured dispersion already made by a chemicals manufacturer.

Moreover, it is also within the scope of the present disclosure to use "hand-made" dispersions, i.e., dispersions made in small-scale by an end-user. Such dispersions may be made by providing a mixture of about 20 percent of the binder (B) in water, heating the mixture to temperature of 90° C. to 100° C. and intensively stirring the mixture for several hours. It is possible to manufacture the formulation as a final product so that it can be readily used by the end-user for the process according to the present disclosure. And, it is of course similarly possible to manufacture a concentrate, which may be diluted by the end-user with additional water (C) to the desired concentration for use.

In an embodiment, a composition (comprising an NVP, an NVP-antimicrobial protein, or an agriculturally acceptable salt thereof, and an excipient) suitable for SSI application or a coating formulation (comprising an NVP, an NVP-antimicrobial protein, or an agriculturally acceptable salt thereof, and an excipient), contains the active ingredient and a carrier, such as water, and may also one or more co-formulants selected from a dispersant, a wetter, an antifreeze, a thickener, a preservative, an emulsifier and a binder or sticker.

In some embodiments, an exemplary solid formulation of an NVP, an NVP-antimicrobial protein, or an agriculturally acceptable salt thereof, is generally milled to a desired particle size, such as the particle size distribution d(0.5) is generally from 3 to 20, preferably 5 to 15, especially 7 to 12 μm.

Furthermore, it may be possible to ship the formulation to the end-user as a kit comprising at least a first component comprising an NVP, an NVP-antimicrobial protein, or an agriculturally acceptable salt thereof (A); and a second component comprising at least one polymeric binder (B). Further additives (D) may be a third separate component of the kit, or may be already mixed with components (A) and/or (B). The end-user may prepare the formulation for use by just adding water (C) to the components of the kit and mixing. The components of the kit may also be formulations in water. Of course it is possible to combine an aqueous formulation of one of the components with a dry formulation of the other component(s). As an example, the kit can consist of one formulation of an NVP, an NVP-antimicrobial protein, or an agriculturally acceptable salt thereof (A) and optionally water (C); and a second, separate formulation of at least one polymeric binder (B), water as component (C) and optionally components (D).

The concentrations of the components (A), (B), (C) and optionally (D) will be selected by the skilled artisan depending of the technique to be used for coating/treating. In general, the amount of an NVP, an NVP-antimicrobial protein, or an agriculturally acceptable salt thereof (A) may be up to 50, preferably 1 to 50, such as 10 to 40, especially 15 to 30, percent by weight, based on weight of the composition. The amount of polymeric binder (B) may be in the range of 0.01 to 30, preferably 0.5 to 15, more preferably 1 to 10, especially 1 to 5, percent by weight, based on weight of the composition. If present, in general the amount of additional components (D) is from 0.1 to 20, preferably 0.5 to 15, percent by weight, based on weight of the composition. If present, suitable amounts of pigments and/or dyestuffs and/or fragrances are in general 0.01 to 5, preferably 0.1 to 3, more preferably 0.2 to 2, percent by weight, based on weight of the composition. A typical formulation ready for use comprises 0.1 to 40, preferably 1 to 30, percent of components (A), (B), and optionally (D), the residual amount being water (C). A typical concentration of a concentrate to be diluted by the end-user may comprise 5 to 70, preferably 10 to 60, percent of components (A), (B), and optionally (D), the residual amount being water (C).

Illustrative Mixtures, Compositions, Products, and Transgenic Organisms

The present disclosure contemplates mixtures, compositions, products, and transgenic organisms that contain—or, in the case of transgenic organisms, express or otherwise produce—one or more NVPs, or one or more NVP-antimicrobial proteins.

In some embodiments, the illustrative mixtures consists of: (1) an NVP, an NVP-antimicrobial proteins, or an agriculturally acceptable salt thereof; and (2) an excipient (e.g., any of the excipients described herein).

In some embodiments, the mixtures of the present disclosure consist of: (1) one or more NVPs, one or more NVP-antimicrobial proteins, or an agriculturally acceptable salt thereof; and (2) one or more excipients (e.g., any of the excipients described herein).

In some embodiments, the mixtures of the present disclosure consist of: (1) one or more NVPs, one or more NVP-antimicrobial proteins, or an agriculturally acceptable salt thereof; and (2) one or more excipients (e.g., any of the excipients described herein); wherein either of the foregoing (1) or (2) can be used concomitantly, or sequentially.

Any of the combinations, mixtures, products, polypeptides and/or plants utilizing an NVP, or an NVP-antimicrobial protein (as described herein), can be used to control pathogenic microbes, their growth, and/or the damage caused by their actions, especially their damage to plants.

Compositions comprising an NVP or an NVP-antimicrobial protein, or an agriculturally acceptable salt thereof, and an excipient, can include agrochemical compositions. For example, in some embodiments, agrochemical compositions can include, but is not limited to, aerosols and/or aerosolized products (e.g., sprays, fumigants, powders, dusts, and/or gases); seed dressings; oral preparations (e.g., microbe food, etc.); or a transgenic organisms (e.g., a cell, a plant, or an animal) expressing and/or producing an NVP or an NVP-antimicrobial protein, either transiently and/or stably.

In some embodiments, the active ingredients of the present disclosure can be applied in the form of compositions and can be applied to the crop area or plant to be treated, simultaneously or in succession, with other non-active compounds. These compounds can be fertilizers, weed killers, cryoprotectants, surfactants, detergents, soaps, dormant oils, polymers, and/or time-release or biodegradable carrier formulations that permit long-term dosing of a target area following a single application of the formulation. One or more of these non-active compounds can be prepared, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Methods of applying an active ingredient of the present disclosure or an agrochemical composition of the present disclosure that consists of an NVP or NVP-antimicrobial protein or an agriculturally acceptable salt thereof, and an excipient, as produced by the methods described herein of the present disclosure, include leaf application, seed coating and soil application. In some embodiments, the number of applications and the rate of application depend on the intensity of infestation by the corresponding pathogenic microbe.

The composition comprising an NVP or an NVP-antimicrobial protein or an agriculturally acceptable salt thereof and an excipient may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such antimicrobial polypeptide, the polypeptide may be present in a concentration of from about 1% to about 99% by weight.

In some embodiments, compositions containing NVPs or NVP-antimicrobial proteins (or an agriculturally acceptable salt thereof) may be prophylactically applied to an environmental area to prevent infestation by a susceptible pathogenic microbe, for example, a lepidopteran and/or coleopteran pathogenic microbe, which may be killed or reduced in numbers in a given area by the methods of the invention. In some embodiments, the pathogenic microbe ingests, or comes into contact with, a antimicrobially-effective amount of the polypeptide.

In some embodiments, the antimicrobial compositions described herein may be made by formulating either the NVP or NVP-antimicrobial-protein or an agriculturally acceptable salt thereof transformed bacterial, yeast, or other cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the antimicrobial composition with suitable adjuvants using conventional formulation techniques. Suitable formulations and application methods are described in U.S. Pat. No. 6,468,523, the disclosure of which is incorporated herein by reference in its entirety.

Methods of Using the Present Disclosure

Any of the methods of using the present disclosure, e.g., methods of protecting plants, plant parts, and seeds; or methods of using an NVP and/or mixtures and/or compositions comprising one or more NVPs; can be implemented using any one or more of the NVPs or NVP-antimicrobial proteins as described herein. For example, any of the methods of using the present disclosure as described herein can be implemented using, e.g., one or more NVP having the amino acid sequence selected from any one of SEQ ID NOs: 4-19, or 66, which are likewise described herein.

In some embodiments, methods of protecting plants, plant parts, and seeds; methods of using an NVP; and/or methods of using mixtures and/or compositions comprising one or more NVPs; can be implemented using an NCR13 variant peptide (NVP) of the present disclosure comprises, consists essentially of, or consists of, an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in the foregoing Table 1, wherein the amino acid added to the N-terminus can be any natural or non-natural amino acid other than glycine or alanine.

In some embodiments, methods of using an NVP of the present disclosure; methods of using mixtures and/or compositions comprising one or more NVPs or one or more NVP-antimicrobial proteins; and/or methods of protecting plants, plant parts, and seeds as described herein; can be implemented using an NCR13 variant peptide (NVP) of the present disclosure comprises, consists essentially of, or consists of, an NCR13 variant peptide (NVP) having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof.

In some embodiments, methods of using an NVP of the present disclosure; methods of using mixtures and/or compositions comprising one or more NVPs or one or more NVP-antimicrobial proteins; and/or methods of protecting plants, plant parts, and seeds as described herein; can be implemented using an NCR13 variant peptide (NVP) having antimicrobial activity against one or more microbe species, comprises, consists essentially of, or consists of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or an agriculturally acceptable salt thereof.

In some embodiments, methods of using an NVP of the present disclosure; methods of using mixtures and/or compositions comprising one or more NVPs or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is a natural amino acid.

In some embodiments, methods of using an NVP of the present disclosure; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is V, L, I, M, F, W, P, S, T, Y, N, Q, D, E, K, R, or H.

In some embodiments, methods of using an NVP of the present disclosure; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L, M, F, W, S, Y, D, or E.

In some embodiments, methods of using an NVP of the present disclosure; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof; wherein the amino acid is L or W.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises at least one mutation relative to a WT-NCR13 amino acid sequence as set forth in SEQ ID NO: 1; wherein $X_1$ is an amino acid addition to the N-terminus of the WT-NCR13 amino acid sequence; and wherein $X_1$ is any natural or non-natural amino acid other than glycine or alanine.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein $X_1$ is an N-terminus addition of an amino acid to a WT-NCR13 amino acid sequence as set forth in SEQ ID NO: 1; and wherein $X_1$ is any natural or non-natural amino acid other than glycine or alanine.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: V, L, I, M, F, W, P, S, T, Y, N, Q, D, E, K, R, or H; or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is a natural amino acid selected from: L, M, F, W, S, Y, D, or E; or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence according to Formula (I): X$_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein X$_1$ is a natural amino acid selected from: L or W; or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "VTKPCQSDKDCKK-FACRKPKVPKCINGFCKCVR" (SEQ ID NO: 4), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "LTKPCQSDKDCKK-FACRKPKVPKCINGFCKCVR" (SEQ ID NO: 5), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ITKPCQSDKDCKK-FACRKPKVPKCINGFCKCVR" (SEQ ID NO: 6), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "MTKPCQSDKDCKK-FACRKPKVPKCINGFCKCVR" (SEQ ID NO: 7), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "FTKPCQSDKDCKK-FACRKPKVPKCINGFCKCVR" (SEQ ID NO: 8), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "WTKPCQSDKDCKK-FACRKPKVPKCINGFCKCVR" (SEQ ID NO: 9), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "PTKPCQSDKDCKK-FACRKPKVPKCINGFCKCVR" (SEQ ID NO: 10), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "STKPCQSDKDCKK-FACRKPKVPKCINGFCKCVR" (SEQ ID NO: 11), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "TTKPCQSDKDCKK-FACRKPKVPKCINGFCKCVR" (SEQ ID NO: 12), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "YTKPCQSDKDCKK-FACRKPKVPKCINGFCKCVR" (SEQ ID NO: 13), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "NTKPCQSDKDCKK-FACRKPKVPKCINGFCKCVR" (SEQ ID NO: 14), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "QTKPCQSDKDCKK-FACRKPKVPKCINGFCKCVR" (SEQ ID NO: 15), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "DTKPCQSDKDCKK-FACRKPKVPKCINGFCKCVR" (SEQ ID NO: 16), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "ETKPCQSDKDCKK-FACRKPKVPKCINGFCKCVR" (SEQ ID NO: 17), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "KTKPCQSDKDCKK-FACRKPKVPKCINGFCKCVR" (SEQ ID NO: 18), or an agriculturally acceptable salt thereof.

In some embodiments, methods of using an NVP; methods of using mixtures and/or compositions comprising one or more NVPs, and/or one or more NVP-antimicrobial proteins; and/or methods of protecting plants, plant parts, and seeds as described herein; can be implemented using an NVP of the present disclosure, wherein the NVP can comprise, consist essentially of, or consist of, an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence: "HTKPCQSDKDCKK-FACRKPKVPKCINGFCKCVR" (SEQ ID NO: 19), or an agriculturally acceptable salt thereof.

Methods for Protecting Plants, Plant Parts, and Seeds

In some embodiments, the present disclosure provides a method for controlling a pathogenic microbe in agronomic and/or nonagronomic applications, comprising contacting the pathogenic microbe or its environment, a solid surface, including a plant surface, or part thereof, with a antimicrobially effective amount of one or more of the NVPs of the invention, one or more NVP-antimicrobial proteins, or an agriculturally acceptable salt thereof.

In some embodiments, the present disclosure provides a method for controlling a pathogenic microbe in agronomic and/or nonagronomic applications, comprising contacting the pathogenic microbe or its environment, a solid surface, including a plant surface or part thereof, with a antimicrobially effective amount of a composition comprising at least one NVP of the invention and an excipient.

Examples of suitable compositions comprising: (1) at least one NVP of the invention; two or more of the NVPs of the present disclosure; an NVP-antimicrobial protein; two or more NVP-antimicrobial proteins; or an agriculturally acceptable salt thereof; and (2) an excipient; include said compositions formulated win inactive ingredients to be delivered in the form of: a liquid solution, an emulsion, a powder, a granule, a nanoparticle, a microparticle, or a combination thereof.

In some embodiments, to achieve contact with a compound, mixture, or composition of the invention to protect a field crop from pathogenic microbes, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising an NVP, an NVP-antimicrobial protein, or an agriculturally acceptable salt thereof, and an excipient, can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present disclosure in the form of a soil drench liquid formulation. Also of note is a method for controlling a pathogenic microbe comprising contacting the pathogenic microbe or its environment with a biologically effective amount of an NVP or NVP-antimicrobial protein. Of further note, in some illustrative embodiments, the illustrative method contemplates a soil environment, wherein the composition is applied to the soil as a soil drench formulation. Of further note is that an NVP, an NVP-antimicrobial protein, or an agriculturally acceptable salt thereof, is also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating microbe control devices (e.g., application onto clothing, and the like).

In some embodiments, an NVP, an NVP-antimicrobial protein, or an agriculturally acceptable salt thereof, is also useful in seed treatments for protecting seeds from pathogenic microbes. In the context of the present disclosure and claims, treating a seed means contacting the seed with a biologically effective amount of an NVP, an NVP-antimicrobial protein, or an agriculturally acceptable salt thereof, which is typically formulated as a composition of the invention. This seed treatment protects the seed from microbes and generally can also protect roots and other plant parts in contact with the soil of the seedling developing from the germinating seed. The seed treatment may also provide protection of foliage by translocation of the NVP or NVP-antimicrobial protein within the developing plant. Seed treatments can be applied to all types of seeds, including those from which plants genetically transformed to express specialized traits will germinate. In addition, an NVP or an NVP-antimicrobial protein can be transformed into a plant or part thereof, for example a plant cell, or plant seed, that is already transformed, e.g., those expressing herbicide resistance such as glyphosate acetyltransferase, which provides resistance to glyphosate.

One method of seed treatment is by spraying or dusting the seed with an NVP, an NVP-antimicrobial protein, or an agriculturally acceptable salt thereof, (i.e. as a formulated composition or a mixture comprising an NVP, an NVP-antimicrobial protein, or an agriculturally acceptable salt thereof and an excipient) before sowing the seeds. Compositions formulated for seed treatment generally consist of an NVP, an NVP-antimicrobial protein, or an agriculturally acceptable salt thereof, and a film former or adhesive agent. Therefore, typically, a seed coating composition of the present disclosure consists of a biologically effective amount of an NVP, an NVP-antimicrobial protein, or an agriculturally acceptable salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., Seed Treatment: Progress and Prospects, 1994 BCPC Monograph No. 57, and references listed therein, the disclosures of which are incorporated herein by reference in their entireties.

The treated seed typically comprises an NVP, an NVP-antimicrobial protein, or an agriculturally acceptable salt thereof, in an amount ranging from about 0.01 g to 1 kg per 100 kg of seed (i.e. from about 0.00001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

In some embodiments, the invention provides a method for controlling microbes comprising, providing to said microbe a transgenic plant that comprises in its genome a stably incorporated expression cassette, wherein said stably incorporated expression cassette comprises a polynucleotide operable to encode an NVP.

In some embodiments, the present disclosure provides a method for controlling microbes and/or for protecting against a pathogenic microbe, wherein the pathogenic microbe is selected from the group consisting of: *Monilinia, Botrytis, Fusarium, Venturia, Wilsonomyces, Botryosphaeria, Penicillium, Rhizopus, Aspergillus, Podosphaera, Erysiphe, Golovinomyces, Leveillula, Peronospora, Pseudoperonospora, Plasmopara, Bremia, Cladosporium, Neofabraea, Microdochium, Marssonina, Sclerotinia, Rhizopus, Didymella, Alternaria, Verticillium, Phytophthora, Colletotrichum, Cercospora, Phakopsora, Rhizoctonia, Sclerotinia, Pythium, Phoma, Gaeumannomces, Leptoshaeria,* or *Puccinia.*

Methods of Using Mixtures and Compositions

In some embodiments, the invention provides a method of combating, controlling, or inhibiting a pathogenic microbe comprising, applying a antimicrobially effective amount of the combination, mixture, or composition comprising, consisting essentially of, or consisting of an NVP, an NVP-antimicrobial protein, and/or combinations thereof, to (i) the pathogenic microbe, a locus of the pathogenic microbe, a food supply of the pathogenic microbe, a habitat of the pathogenic microbe, or a breeding ground of the pathogenic microbe; (ii) a plant, a seed, a plant part, a locus of a plant, or an environment of a plant that is susceptible to an attack by the pathogenic microbe; (iii) an animal, a locus of an animal, or an environment of an animal susceptible to an attack by the pathogenic microbe; or (iv) a combination of any one of (i)-(iii).

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence having an N-terminus addition of an amino acid to a WT-NCR13 amino acid sequence as set forth in SEQ ID NO:1, wherein the amino acid is any natural or non-natural amino acid other than glycine or alanine; or an agriculturally acceptable salt thereof; and wherein said method comprises, preparing the mixture and then applying said mixture to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination of any one of (i)-(iii).

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; and wherein said method comprises, preparing the mixture and then applying said mixture to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination of any one of (i)-(iii).

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is V, L, I, M, F, W, P, S, T, Y, N, Q, D, E, K, R, or H; and wherein said method comprises, preparing the mixture and then applying said mixture to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination of any one of (i)-(iii).

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is L, M, F, W, S, Y, D, or E; and wherein said method comprises, preparing the mixture and then applying said mixture to (i) the microbe, a locus of the microbe, a food supply of the microbe, a habitat of the microbe, or a breeding ground of the microbe; (ii) a plant, a seed, a plant part, a locus of a plant, or an environment of a plant that is susceptible to an attack by the microbe; (iii) an animal, a locus of an animal, or an environment of an animal susceptible to an attack by the microbe; or (iv) a combination of any one of (i)-(iii).

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 4-19, or 66; or an agriculturally acceptable salt thereof, and wherein said method comprises, preparing the mixture and then applying said mixture to the locus of an microbe.

In some embodiments, the present disclosure provides a method of using a mixture comprising: (1) an NVP, an NVP-antimicrobial protein, or an agriculturally acceptable salt thereof; and (2) an excipient; to control microbes, wherein the NVP is selected from one or any combination of the NVPs described herein, e.g., an NVP having antimicrobial activity against one or more microbe species, said NVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 5, 7, 8, 9, 11, 13, 16, and 17; or an agriculturally acceptable salt thereof; and wherein said method comprises, preparing the mixture and then applying said mixture to the locus of an microbe.

In some embodiments, the present disclosure provides a method of protecting a plant from microbes comprising, providing a plant that expresses an NVP, or polynucleotide encoding the same, wherein the NVP has an amino acid sequence as set forth in any one of SEQ ID NOs: 4-19, or 66, or a complementary nucleotide sequence thereof.

In some embodiments, the present disclosure provides a method of protecting a plant from microbes comprising, providing a plant that expresses an NVP, or polynucleotide encoding the same, wherein the NVP has an amino acid sequence as set forth in any one of SEQ ID NOs: 5, 7, 8, 9, 11, 13, 16, and 17, or a complementary nucleotide sequence thereof.

In some embodiments, the present disclosure provides a method of protecting a plant from microbes comprising, providing a plant that expresses an NVP, or polynucleotide encoding the same, wherein the NVP further comprises a homopolymer or heteropolymer of two or more NVPs, wherein the amino acid sequence of each NVP is the same or different.

In some embodiments, the present disclosure provides a method of protecting a plant from microbes comprising, providing a plant that expresses an NVP, or polynucleotide encoding the same, wherein the NVP is a fused protein comprising two or more NVPs separated by a cleavable or non-cleavable linker, and wherein the amino acid sequence of each NVP may be the same or different.

In some embodiments, the present disclosure provides a method of protecting a plant from microbes comprising, providing a plant that expresses an NVP, or polynucleotide encoding the same, wherein the NVP is a fused protein comprising two or more NVPs separated by a cleavable linker. In some embodiments, the linker has an amino acid sequence as set forth in any one of SEQ ID NOs: 39-51.

In some embodiments, the present disclosure provides a method of protecting a plant from microbes comprising, providing a plant that expresses an NVP, or polynucleotide encoding the same, wherein the NVP is a fused protein comprising two or more NVPs separated by a linker, wherein the linker is cleavable inside at least one of (i) the gut or hemolymph of an invertebrate, and (ii) cleavable inside the gut of a mammal.

In some embodiments, the present disclosure provides a method for controlling microbes comprising, providing to said microbe a transgenic plant that comprises in its genome a stably incorporated expression cassette, wherein said stably incorporated expression cassette comprises polynucleotide operable to encode an NVP.

In some embodiments, the present disclosure provides a method of combating, controlling, or inhibiting a pathogenic microbe comprising, applying a antimicrobially effective amount of a mixture comprising: (1) an NVP, an NVP-antimicrobial protein, or an agriculturally acceptable salt thereof; and (2) an excipient; wherein the NVP is selected from one or any combination of the NVPs described herein, e.g., an NVP having an amino acid sequence set forth in any one of SEQ ID NOs: 4-19, or 66, or an agriculturally acceptable salt thereof; wherein the mixture is applied to (i) the pathogenic microbe, a locus of the pathogenic microbe, a food supply of the pathogenic microbe, a habitat of the pathogenic microbe, or a breeding ground of the pathogenic microbe; (ii) a plant, a seed, a plant part, a locus of a plant, or an environment of a plant that is susceptible to an attack by the pathogenic microbe; (iii) an animal, a locus of an animal, or an environment of an animal susceptible to an attack by the pathogenic microbe; or (iv) a combination of any one of (i)-(iii).

In some embodiments, the present disclosure provides a method of combating, controlling, or inhibiting a pathogenic microbe comprising, applying a antimicrobially effective amount of a mixture comprising: (1) an NVP, an NVP-antimicrobial protein, or an agriculturally acceptable salt thereof; and (2) an excipient; wherein the NVP is selected from one or any combination of the NVPs described herein, e.g., an NVP having an amino acid sequence set forth in any one of SEQ ID NOs: 5, 7, 8, 9, 11, 13, 16, and 17, or an agriculturally acceptable salt thereof; wherein the mixture is applied to (i) the pathogenic microbe, a locus of the pathogenic microbe, a food supply of the pathogenic microbe, a habitat of the pathogenic microbe, or a breeding ground of the pathogenic microbe; (ii) a plant, a seed, a plant part, a locus of a plant, or an environment of a plant that is susceptible to an attack by the pathogenic microbe; (iii) an animal, a locus of an animal, or an environment of an animal susceptible to an attack by the pathogenic microbe; or (iv) a combination of any one of (i)-(iii).

Pathogenic Microbes

"Pathogenic microbe" refers to any microbe that is deleterious or pathogenic to an organism; e.g., any microbe that causes or exacerbates an infection or disease in a living organism. For example, in some embodiments, a pathogenic microbe of the present disclosure can be a pathogen to plants, e.g., a phytopathogen, such as a bacterium, a protozoan, or a fungus; in other embodiments, a pathogenic microbe can be a pathogen to animals. As used herein, a "plant pathogenic microbe" or "plant pathogen" can refer to a microbe that can cause disease into whole plants, plant tissues, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

In some embodiments, the present disclosure provides a method for combating, controlling, or inhibiting microbes, e.g., pathogenic microbes.

In some embodiments, the pathogenic microbe is a phytopathogenic microbe.

In some embodiments, the phytopathogenic microbe is phytopathogenic fungus.

In some embodiments, the phytopathogenic fungus is a fungus belonging to the genera: *Monilinia, Botrytis, Fusarium, Venturia, Wilsonomyces, Botryosphaeria, Penicillium, Rhizopus, Aspergillus, Podosphaera, Erysiphe, Golovinomyces, Leveillula, Peronospora, Pseudoperonospora, Plasmopara, Bremia, Cladosporium, Neofabraea, Microdochium, Marssonina, Sclerotinia, Rhizopus, Didymella, Alternaria, Verticillium, Phytophthora, Colletotrichum, Cercospora, Phakopsora, Rhizoctonia, Sclerotinia, Pythium, Phoma, Gaeumannomces, Leptoshaeria*, or *Puccinia*.

In some embodiments, the present disclosure provides a method for combating, controlling, or inhibiting microbes, e.g., pathogenic microbes, wherein the pathogenic microbe is a *Fusarium* sp., *Alternaria* sp., *Verticillium* sp., *Phytophthora* sp., *Colletotrichum* sp., *Botrytis* sp., *Cercospora* sp., *Phakopsora* sp. *Rhizoctonia* sp., *Sclerotinia* sp., *Pythium* sp., *Phoma* sp., *Gaeumannomces* sp. *Leptoshaeria* sp., *Puccinia* sp., *Ascochyta* sp., *Diplodia* sp., *Erysiphe* sp., *Gaeumanomyces* sp., *Helminthosporium* sp., *Macrophomina* sp., *Nectria* sp., *Peronospora* sp., *Phymatotrichum* sp., *Plasmopara* sp., *Podosphaera* sp., *Pyrenophora* sp., *Pyricularia* sp., *Scerotium* sp., *Septoria* sp., *Thielaviopsis* sp., *Uncinula* sp., or *Venturia* sp.

In some embodiments, the pathogenic microbe is a pathogenic fungus. In some embodiments, the pathogenic fungus is a dermatophyte. In some embodiments, the dermatophyte is selected from the group consisting of *Trichophyton ruhrum, Trichophyton interdigitale, Trichophyton violaceum, Trichophyton tonsurans, Trichophyton soudanense, Trichophyton mentagrophytes, Microsporum flavum, Epidermophyton floccosum*, and *Microsporum gypseum*.

In some embodiments, the pathogenic microbe is derived from organisms belonging to the *Aspergillus, Cryptococcus, Penicillium, Rhizopus, Apophysomyces, Cunninghamella, Saksenaea, Rhizomucor, Syncephalostrum, Cokeromyces, Actinomucor, Pythium, Fusarium, Histoplasmosis*, or *Blastomyces* genus.

In some embodiments, the pathogenic microbe is derived from organisms belonging to *Candida* genus. In some embodiments, the pathogenic microbes derived from the *Candida* genus are from the species *Candida albicans, C. glabrata, C parasilosis, C. tropicalis*, or *C. krusei*.

Any of the pathogenic microbes described herein can combatted, controlled, or inhibited using an engineered, non-naturally occurring antimicrobial peptide, or an agriculturally acceptable salt thereof consisting of an amino acid sequence set forth in SEQ ID NO: 1, and any of the excipients described herein.

ILLUSTRATIVE EMBODIMENTS

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is any natural or non-natural amino acid other than glycine or alanine; or an agriculturally acceptable salt thereof.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is a natural amino acid other than glycine or alanine; or an agriculturally acceptable salt thereof.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is wherein the amino acid is V, L, I, M, F, W, P, S, T, Y, N, Q, D, E, K, R, or H; or an agriculturally acceptable salt thereof.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is wherein the amino acid is L, M, F, W, S, Y, D, or E; or an agriculturally acceptable salt thereof.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is wherein the amino acid is L or W; or an agriculturally acceptable salt thereof.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 4-19, or 66.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 5, 7, 8, 9, 11, 13, 16, or 17.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence set forth in SEQ ID NOs: 5 or 9.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino sequence as set forth in any one of SEQ ID NOs: 4-19, or 66.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino acid sequence as set forth in any one of SEQ ID NOs: 5, 7, 8, 9, 11, 13, 16, or 17.

In some embodiments, the present disclosure provides an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino acid sequence set forth in SEQ ID NOs: 5 or 9.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is any natural or non-natural amino acid other than glycine or alanine; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is a natural amino acid other than glycine or alanine; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is V, L, I, M, F, W, P, S, T, Y, N, Q, D, E, K, R, or H; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is L, M, F, W, S, Y, D, or E; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the amino acid is L or W; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 4-19, or 66; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 5, 7, 8, 9, 11, 13, 16, or 17; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 5 or 9; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino sequence as set forth in any one of SEQ ID NOs: 4-19, or 66; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino acid sequence as set forth in any one of SEQ ID NOs: 5, 7, 8, 9, 11, 13, 16, or 17; or a complementary nucleotide sequence thereof.

In some embodiments, the present disclosure provides a polynucleotide operable to encode an antimicrobial NCR13 variant peptide (NVP) having antimicrobial activity against one or more microbes, said NVP comprising an N-terminus addition of an amino acid to a WT-NCR13 amino acid sequence as set forth in SEQ ID NO: 1, wherein the NVP consists of an amino acid sequence as set forth in any one of SEQ ID NOs: 5 or 9; or a complementary nucleotide sequence thereof.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; and an excipient.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural amino acid other than glycine or alanine; and an excipient.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid V, L, I, M, F, W, P, S, T, Y, N, Q, D, E, K, R, or H; and an excipient.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid L, M, F, W, S, Y, D, or E; and an excipient.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid L or W; and an excipient.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 4-19, or 66.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 5, 7, 8, 9, 11, 13, 16, or 17.

In some embodiments, the present disclosure provides a composition comprising an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the NVP comprises an amino sequence that is at least 95%, 96%, 97%, 97%, 98%, 99% or 100% identical to an amino acid sequence as set forth in any one of SEQ ID NOs: 5 or 9.

In some embodiments, the present disclosure provides a composition comprising an antimicrobial NCR13 variant peptide (NVP) having antimicrobial activity against one or more microbes, or an agriculturally acceptable salt thereof, said NVP consisting of an N-terminus addition of an amino acid to a WT-NCR13 amino acid sequence as set forth in SEQ ID NO: 1, wherein the NVP consists of an amino sequence that is set forth in any one of SEQ ID NOs: 4-19, or 66.

In some embodiments, the present disclosure provides a composition comprising an antimicrobial NCR13 variant peptide (NVP) having antimicrobial activity against one or more microbes, or an agriculturally acceptable salt thereof, said NVP consisting of an N-terminus addition of an amino acid to a WT-NCR13 amino acid sequence as set forth in SEQ ID NO: 1, wherein the NVP consists of an amino sequence as set forth in any one of SEQ ID NOs: 5, 7, 8, 9, 11, 13, 16, or 17.

In some embodiments, the present disclosure provides a composition comprising an antimicrobial NCR13 variant peptide (NVP) having antimicrobial activity against one or more microbes, or an agriculturally acceptable salt thereof, said NVP consisting of an N-terminus addition of an amino acid to a WT-NCR13 amino acid sequence as set forth in SEQ ID NO: 1, wherein the NVP consists of an amino sequence as set forth in any one of SEQ ID NOs: 5 or 9.

In some embodiments, the present disclosure provides a method of combating, controlling, or inhibiting a microbe comprising applying a antimicrobially effective amount of: (1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof.

In some embodiments, the present disclosure provides a method of combating, controlling, or inhibiting a microbe comprising applying a antimicrobially effective amount of: (1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the amino acid is a natural amino acid.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the amino acid is V, L, I, M, F, W, P, S, T, Y, N, Q, D, E, K, R, or H.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the amino acid is L, M, F, W, S, Y, D, or E.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the NVP comprises an amino sequence that is at least 95%, 96%, 97%, 97%, 98%, 99% or 100% identical to an amino acid sequence as set forth in any one of SEQ ID NOs: 4-19, or 66.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the NVP comprises an amino sequence that is at least 95%, 96%, 97%, 97%, 98%, 99% or 100% identical to an amino acid sequence as set forth in any one of SEQ ID NOs: 5, 7, 8, 9, 11, 13, 16, or 17.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a pathogenic fungus.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the pathogenic fungus is a plant-specific pathogenic fungus, or a phytopathogenic fungus.

In some embodiments, the present disclosure provides a method of combating, controlling, or inhibiting a microbe comprising applying a antimicrobially effective amount of:
(1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the phytopathogenic fungus is a phytopathogenic fungus belonging to the genera: *Monilinia, Botrytis, Fusarium, Venturia, Wilsonomyces, Botryosphaeria, Penicillium, Rhizopus, Aspergillus, Podosphaera, Erysiphe, Golovinomyces, Leveillula, Peronospora, Pseudoperonospora, Plasmopara, Bremia, Cladosporium, Neofabraea, Microdochium, Marssonina, Sclerotinia, Rhizopus, Didymella, Alternaria, Verticillium, Phytophthora, Colletotrichum, Cercospora, Phakopsora, Rhizoctonia, Sclerotinia, Pythium, Phoma, Gaeumannomces, Leptoshaeria,* or *Puccinia.*

In some embodiments, the present disclosure provides a method of combating, controlling, or inhibiting a microbe comprising applying a antimicrobially effective amount of: (1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a microbe belonging to the genera: *Monilinia* or *Botrytis.*

In some embodiments, the present disclosure provides a method of combating, controlling, or inhibiting a microbe comprising applying a antimicrobially effective amount of: (1) an antimicrobial NCR13 variant peptide (NVP) having antimicrobial activity against one or more microbes, or an agriculturally acceptable salt thereof, said NVP comprising an N-terminus addition of an amino acid to a WT-NCR13 amino acid sequence as set forth in SEQ ID NO: 1, wherein the amino acid is any natural or non-natural amino acid other than glycine or alanine; or
(2) a composition comprising the NVP and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a *Monilinia fructicola* or a *Botrytis cinerea.*

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "VTKPCQSDKDCKKFACRKPKVPKCINGFCKCVR" (SEQ ID NO: 4).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "LTKPCQSDKDCKKFACRKPKVPKCINGFCKCVR" (SEQ ID NO: 5).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "ITKPCQSDKDCKKFACRKPKVPKCINGFCKCVR" (SEQ ID NO: 6).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "MTKPCQSDKDCKKFACRKPKVPKCINGFCKCVR" (SEQ ID NO: 7).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "FTKPCQSDKDCKKFACRKPKVPKCINGFCKCVR" (SEQ ID NO: 8).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "WTKPCQSDKDCKKFACRKPKVPKCINGFCKCVR" (SEQ ID NO: 9).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "PTKPCQSDKDCKKFACRKPKVPKCINGFCKCVR" (SEQ ID NO: 10).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino sequence that is at least 95%, 96%, 97%, 97%, 98%, 99% or 100% identical to the amino acid sequence: "STKPCQSDKDCKKFACRKPKVPKCINGFCKCVR" (SEQ ID NO: 11).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "TTKPCQSDKDCKKFACRKPKVPKCINGFCKCVR" (SEQ ID NO: 12).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "YTKPCQSDKDCKKFACRKPKVPKCINGFCKCVR" (SEQ ID NO: 13).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "NTKPCQSDKDCKKFACRKPKVPKCINGFCKCVR" (SEQ ID NO: 14).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "QTKPCQSDKDCKKFACRKPKVPKCINGFCKCVR" (SEQ ID NO: 15).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "DTKPCQSDKDCKKFACRKPKVPKCINGFCKCVR" (SEQ ID NO: 16).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "ETKPCQSDKDCKKFACRKPKVPKCINGFCKCVR" (SEQ ID NO: 17).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "KTKPCQSDKDCKKFACRKPKVPKCINGFCKCVR" (SEQ ID NO: 18).

In some embodiments, the present disclosure provides an antimicrobial NCR13 variant peptide (NVP) having antimicrobial activity against one or more microbes, or an agriculturally acceptable salt thereof, said NVP comprising, consisting essentially of, or consisting of, an amino acid sequence that is at least 95%, 96%, 97%, 97%, 98%, 99% or 100% identical to the amino acid sequence: "HTKPCQSDKDCKKFACRKPKVPKCINGFCKCVR" (SEQ ID NO: 19).

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to an amino sequence as set forth in any one of SEQ ID NOs: 5, 7, 8, 9, 11, 13, 16, or 17, or an agriculturally acceptable salt thereof.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is V, L, I, M, F, W, P, S, T, Y, N, Q, D, E, K, R, or H; or an agriculturally acceptable salt thereof.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is L, M, F, W, S, Y, D, or E; or an agriculturally acceptable salt thereof, wherein the NVP is a homopolymer or heteropolymer of two or more NVPs, wherein the amino acid sequence of each NVP is the same or different.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof, wherein the NVP is a fused protein comprising two or more NVPs separated by a cleavable or non-cleavable linker, and wherein the amino acid sequence of each NVP may be the same or different.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof, wherein the NVP is a fused protein comprising two or more NVPs separated by a cleavable or non-cleavable linker, and wherein the amino acid sequence of each NVP may be the same or different; wherein the linker is a cleavable linker.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof, wherein the NVP is a fused protein comprising two or more NVPs separated by a cleavable or non-cleavable linker, and wherein the amino acid sequence of each NVP may be the same or different; wherein the linker is a cleavable linker; and wherein the linker has an amino acid sequence as set forth in any one of SEQ ID NOs: 39-51.

In some embodiments, the present disclosure provides an antimicrobial NCR13 variant peptide (NVP) having antimicrobial activity against one or more microbe species, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof, wherein the NVP is a fused protein comprising two or more NVPs separated by a cleavable or non-cleavable linker, and wherein the amino acid sequence of each NVP may be the same or different; wherein the linker is a cleavable linker; and wherein the linker is cleavable.

In some embodiments, the present disclosure provides an antimicrobial combination comprising, consisting essentially of, or consisting of, two or more NVPs, said NVPs comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof.

In some embodiments, the present disclosure provides an antimicrobial composition comprising, consisting essentially of, or consisting of, one or more NVPs, said NVP comprising an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or an agriculturally acceptable salt thereof, and an excipient.

In some embodiments, the present disclosure provides a polynucleotide operable to encode an NVP, said NVP comprising, consisting essentially of, or consisting of, an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary polynucleotide sequence thereof.

In some embodiments, the present disclosure provides a polynucleotide operable to encode an NVP, said NVP comprising, consisting essentially of, or consisting of, an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary polynucleotide sequence thereof; wherein the polynucleotide encodes an NVP comprising, consisting essentially of, or consisting of, an amino sequence as set forth in any one of SEQ ID NOs: 5, 7, 8, 9, 11, 13, 16, or 17.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-

C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17; wherein the NVP is a homopolymer or heteropolymer of two or more NVPs, wherein the amino acid sequence of each NVP is the same or different.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17; wherein the NVP is a homopolymer or heteropolymer of two or more NVPs, wherein the amino acid sequence of each NVP is the same or different; wherein the NVP is a fused protein comprising two or more NVPs separated by a cleavable or non-cleavable linker, and wherein the amino acid sequence of each NVP may be the same or different.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17; wherein the NVP is a homopolymer or heteropolymer of two or more NVPs, wherein the amino acid sequence of each NVP is the same or different; wherein the NVP is a fused protein comprising two or more NVPs separated by a cleavable or non-cleavable linker, and wherein the amino acid sequence of each NVP may be the same or different; wherein the linker is a cleavable linker.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17; wherein the NVP is a homopolymer or heteropolymer of two or more NVPs, wherein the amino acid sequence of each NVP is the same or different; wherein the NVP is a fused protein comprising two or more NVPs separated by a cleavable or non-cleavable linker, and wherein the amino acid sequence of each NVP may be the same or different; and wherein the linker has an amino acid sequence as set forth in any one of SEQ ID NOs: 39-51.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the NVP comprises, consists essentially of, or consists of, an amino sequence as set forth in any one of SEQ ID NOs: 5, 7, 8, 9, 11, 13, 16, or 17; wherein the NVP is a homopolymer or heteropolymer of two or more NVPs, wherein the amino acid sequence of each NVP is the same or different; wherein the NVP is a fused protein comprising two or more NVPs separated by a cleavable or non-cleavable linker, and wherein the amino acid sequence of each NVP may be the same or different; and wherein the linker is cleavable.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the vector is a plasmid comprising an alpha-MF signal.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the host cell is a yeast strain.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the host cell is a yeast strain is selected from any species belonging to the genera *Saccharomyces*, *Pichia*, *Kluyveromyces*, *Hansenula*, *Yarrowia*, or *Schizosaccharomyces*.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the host cell is a yeast strain is selected from the group consisting of *Kluyveromyces lactis*, *Kluyveromyces marxianus*, *Saccharomyces cerevisiae*, and *Pichia pastoris*.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the host cell is *Kluyveromyces lactis*.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein expression of the NVP provides a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L, at least 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of NVP per liter of yeast culture medium.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein expression of the NVP in the medium results in the expression of a single NVP in the medium.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein expression of the NVP in the medium results in the expression of an NVP polymer comprising two or more NVP peptides in the medium.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the vector comprises two or three expression cassettes, each expression cassette operable to encode the NVP of the first expression cassette.

In some embodiments, the present disclosure provides a method of producing an NVP, the method comprising: (a) preparing a vector comprising a first expression cassette comprising, consisting essentially of, or consisting of, a polynucleotide operable to encode an NVP, or a complementary nucleotide sequence thereof, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; (b) introducing the vector into a host cell; and (c) growing the host cell in a growth medium under conditions operable to enable expression of the NVP and secretion into the growth medium; wherein the vector comprises two or three expression cassettes, each expression cassette operable to encode the NVP of the first expression cassette, or an NVP of a different expression cassette.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a pathogenic fungus.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a plant-specific pathogenic fungus, or a phytopathogenic fungus.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a phytopathogenic fungus belonging to the genera: *Monilinia, Botrytis, Fusarium, Venturia, Wilsonomyces, Botryosphaeria, Penicillium, Rhizopus, Aspergillus, Podosphaera, Erysiphe, Golovinomyces, Leveillula, Peronospora, Pseudoperonospora, Plasmopara, Bremia, Cladosporium, Neofabraea, Microdochium, Marssonina, Sclerotinia, Rhizopus, Didymella, Alternaria, Verticillium, Phytophthora, Colletotrichum, Cercospora, Phakopsora, Rhizoctonia, Sclerotinia, Pythium, Phoma, Gaeumannomces, Leptoshaeria*, or *Puccinia*.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is a phytopathogenic fungus belonging to the genera: *Monilinia* or *Botrytis*.

In some embodiments, the present disclosure provides a method of combating, controlling, or inhibiting a microbe comprising, applying an antimicrobially effective amount of an NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; a combination comprising two or more NVPs; or a composition comprising one or more NVPs and an excipient to: the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof; wherein the microbe is *Monilinia* fructicola or a *Botrytis cinerea*.

In some embodiments, the present disclosure provides a vector comprising a polynucleotide operable to encode an NVP having an amino acid sequence that is at least 95% identical to an amino acid sequence as set forth in any one of SEQ ID NOs: 5, 7, 8, 9, 11, 13, 16, or 17.

In some embodiments, the present disclosure provides a yeast strain comprising: a first expression cassette comprising a polynucleotide operable to encode an NVP, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof.

In some embodiments, the present disclosure provides a yeast strain comprising: a first expression cassette comprising a polynucleotide operable to encode an NVP, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof, wherein the NVP comprises an amino sequence as set forth in any one of SEQ ID NOs: 5, 7, 8, 9, 11, 13, 16, or 17.

In some embodiments, the present disclosure provides a yeast strain comprising: a first expression cassette comprising a polynucleotide operable to encode an NVP, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof; wherein the yeast cell is selected from any species belonging to the genera *Saccharomyces, Pichia, Kluyveromyces, Hansenula, Yarrowia* or *Schizosaccharomyces*.

In some embodiments, the present disclosure provides a yeast strain comprising: a first expression cassette comprising a polynucleotide operable to encode an NVP, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof; wherein the yeast cell is selected from the group consisting of *Kluyveromyces lactis*, *Kluyveromyces marxianus*, *Saccharomyces cerevisiae*, and *Pichia pastoris*.

In some embodiments, the present disclosure provides a yeast strain comprising: a first expression cassette comprising a polynucleotide operable to encode an NVP, said NVP comprising an amino acid sequence that is at least 95% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary nucleotide sequence thereof; wherein the yeast cell is *Kluyveromyces lactis* or *Kluyveromyces marxianus*.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in any one of SEQ ID NOs: 5, 7, 8, 9, 11, 13, 16, or 17.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 5.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 7.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 8.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 9.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 11.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 13.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 16.

In some embodiments, the present disclosure provides an antimicrobial NCR13 variant peptide (NVP) having antimicrobial activity against one or more microbe species, said NVP comprising, consisting essentially of, or consisting of, an amino acid sequence set forth in SEQ ID NO: 17.

In some embodiments, the present disclosure provides a polynucleotide operable to hybridize under stringent hybridization conditions with a polynucleotide segment encoding an NVP, said NVP comprising, consisting essentially of, or consisting of, an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary polynucleotide sequence thereof.

In some embodiments, the present disclosure provides a polynucleotide operable to hybridize under stringent hybridization conditions with a polynucleotide segment encoding an NVP, said NVP comprising, consisting essentially of, or consisting of, an amino acid sequence that is at least 95%, 96%, 97%, 97%, 98%, 99% or 100% identical to the amino acid sequence according to Formula (I): $X_1$-T-K-P-C-Q-S-D-K-D-C-K-K-F-A-C-R-K-P-K-V-P-K-C-I-N-G-F-C-K-C-V-R, wherein the NVP comprises an amino acid addition to the N-terminus of a WT-NCR13 amino acid sequence as set forth in SEQ ID NO:1, and wherein $X_1$ is any natural or non-natural amino acid other than glycine or alanine; or a complementary polynucleotide sequence thereof; wherein the polynucleotide segment encodes an NVP comprising, consisting essentially of, or consisting of, an amino sequence as set forth in any one of SEQ ID NOs: 5, 7, 8, 9, 11, 13, 16, or 17.

EXAMPLES

Example 1. Design of NCR13 Variant Peptides (NVPs)

Polynucleotides operable to encode the peptides shown in Table 2 were cloned into a yeast expression vector, pKLAC1, resulting in the expression vector pLB602 (operable to encode NCR13a), pLB603 (operable to encode WT-NCR13), and the expression vectors pLB602M1-M17 (operable to encode the NVPs of the present disclosure). A representative expression vector is shown in FIG. 1.

TABLE 2

Mutation design strategy.
The NVP mutation design strategy is shown. SEQ ID NO: 1 shows WT-NCR13. SEQ ID NOs: 2-3 show two additional mutant peptides. SEQ ID NOs: 4-19 and 66 are the NVPs of the present disclosure. The column labeled "M" shows the mutation of a given NVP. In Table 2, M represents the amino acid added to the N-terminus of SEQ ID NO: 1, i.e. an amino acid $X_1$ appended to the N-terminal threonine of SEQ ID NO: 1. The plasmid column shows the name of the plasmid used.

| SEQ ID NO | Name | M | Plasmid | Sequence |
|---|---|---|---|---|
| 1 | WTNCR13 | — | pLB603 | TKPCQSDKDCKKFACRKPKVPKCINGFCKCVR |
| 2 | NCR13a | +G | pLB602 | GTKPCQSDKDCKKFACRKPKVPKCINGFCKCVR |

TABLE 2-continued

Mutation design strategy.
The NVP mutation design strategy is shown. SEQ ID NO: 1 shows WT-NCR13. SEQ ID NOs: 2-3 show two additional mutant peptides. SEQ ID NOs: 4-19 and 66 are the NVPs of the present disclosure. The column labeled "M" shows the mutation of a given NVP. In Table 2, M represents the amino acid added to the N-terminus of SEQ ID NO: 1, i.e. an amino acid $X_1$ appended to the N-terminal threonine of SEQ ID NO: 1. The plasmid column shows the name of the plasmid used.

| SEQ ID NO | Name | M | Plasmid | Sequence |
|---|---|---|---|---|
| 3 | NCR13M1 | +A | pLB602M1 | ATKPCQSDKDCKKFACRKPKVPKCINGFCKCVR |
| 4 | NCR13M2 | +V | pLB602M2 | VTKPCQSDKDCKKFACRKPKVPKCINGFCKCVR |
| 5 | NCR13M3 | +L | pLB602M3 | LTKPCQSDKDCKKFACRKPKVPKCINGFCKCVR |
| 6 | NCR13M4 | +I | pLB602M4 | ITKPCQSDKDCKKFACRKPKVPKCINGFCKCVR |
| 7 | NCR13M5 | +M | pLB602M5 | MTKPCQSDKDCKKFACRKPKVPKCINGFCKCVR |
| 8 | NCR13M6 | +F | pLB602M6 | FTKPCQSDKDCKKFACRKPKVPKCINGFCKCVR |
| 9 | NCR13M7 | +W | pLB602M7 | WTKPCQSDKDCKKFACRKPKVPKCINGFCKCVR |
| 10 | NCR13M8 | +P | pLB602M8 | PTKPCQSDKDCKKFACRKPKVPKCINGFCKCVR |
| 11 | NCR13M9 | +S | pLB602M9 | STKPCQSDKDCKKFACRKPKVPKCINGFCKCVR |
| 12 | NCR13M10 | +T | pLB602M10 | TTKPCQSDKDCKKFACRKPKVPKCINGFCKCVR |
| 13 | NCR13M11 | +Y | pLB602M11 | YTKPCQSDKDCKKFACRKPKVPKCINGFCKCVR |
| 14 | NCR13M12 | +N | pLB602M12 | NTKPCQSDKDCKKFACRKPKVPKCINGFCKCVR |
| 15 | NCR13M13 | +Q | pLB602M13 | QTKPCQSDKDCKKFACRKPKVPKCINGFCKCVR |
| 16 | NCR13M14 | +D | pLB602M14 | DTKPCQSDKDCKKFACRKPKVPKCINGFCKCVR |
| 17 | NCR13M15 | +E | pLB602M15 | ETKPCQSDKDCKKFACRKPKVPKCINGFCKCVR |
| 18 | NCR13M16 | +K | pLB602M16 | KTKPCQSDKDCKKFACRKPKVPKCINGFCKCVR |
| 19 | NCR13M17 | +H | pLB602M17 | HTKPCQSDKDCKKFACRKPKVPKCINGFCKCVR |
| 66 | NCR13M18 | +R | pLB602M18 | RTKPCQSDKDCKKFACRKPKVPKCINGFCKCVR |

As shown in FIG. 1, transcription of the peptide expression cassette is controlled by a yeast promoter, pLAC4, and expresses a fusion protein comprising a yeast α-mating factor prepropeptide fusion to the N-terminus of the peptide, which directs the final mature peptide secretion out of the cells. Each vector only contained one expression cassette. Here, NCR13a (SEQ ID NO: 2) was used as a comparator peptide, with which yield and activity of NVPs were compared.

In addition, the vectors comprised the following elements: a Kex2 cleavage site; a multiple cloning site; a LAC4 terminator; and ADH1 promoter; a β-lactamase (bla) gene; and an origin of replication site.

Example 2. Deep-Well Expression Comparison

The vectors described in Example 1, i.e., pLB602 (operable to encode NCR13a, SEQ ID NO: 2), pLB603 (operable to encode WT-NCR13, SEQ ID NO: 1), and pLB602M1-M17 (encoding SEQ ID NOs: 3-19), were then linearized, and transformed into electrocompetent *Kluyveromyces lactis* host cells, for stable integration of the linearized vectors into the *Kluyveromyces lactis* host genome at the pLAC4 loci. The transformed *Kluyveromyces lactis* were then plated on selection agar containing acetamide as the sole nitrogen source to identify strains containing insertions of the expression cassette and its acetamidase selection.

Next, positively identified transformants were used to inoculate the culture wells of a 48-well deep-well culture plate. The deep-well culture plate was sealed with a sterile breathable seal and culture at 23.5° C., 250 rpm for 6 days. After six days in culture, the deep-well culture plate was spun at 4000 rpm for 10 minute to collect the cell pellets and supernatants, the cell pellets were resuspended into 1 mL of 20% glycerol for long-term storage of the strain at −80° C. freezer. The supernatants containing the peptides were subsequently subjected to rpHPLC evaluation to determine peptide yield.

Briefly, to run HPLC, the supernatants were filtered through 0.2 μm filter membrane; then, 300 μL of filtered supernatant was then transferred to a 500 μL 96-well plate for rpHPLC analysis using Ultramate 3000 HPLC system (ThermoFisher®) controlled by Chromeleon 7 software. The HPLC was performed using monolithic C18 columns using water with 0.1% Trifloroacetic acid, and acetonitrile as the mobile phase. An elution protocol using 16-30% acetonitrile was used for peptide purification, in which the peptides were eluted between a range of 22-26% acetonitrile. The corresponding peptide peak area from the HPLC chromatograph was used to calculate the peptide yield. Yield comparisons were based on peak area (mAU) per 20 μL of fermentation beer.

The peaks observed in the HPLC analysis were purified by rpHPLC and subjected to LC/MS identification using a Waters/Micromass ESI-TOF mass spectrometer on-line with an Agilent HPLC system. The LC/MS results confirmed the correct amino acid sequences.

Figure 2:
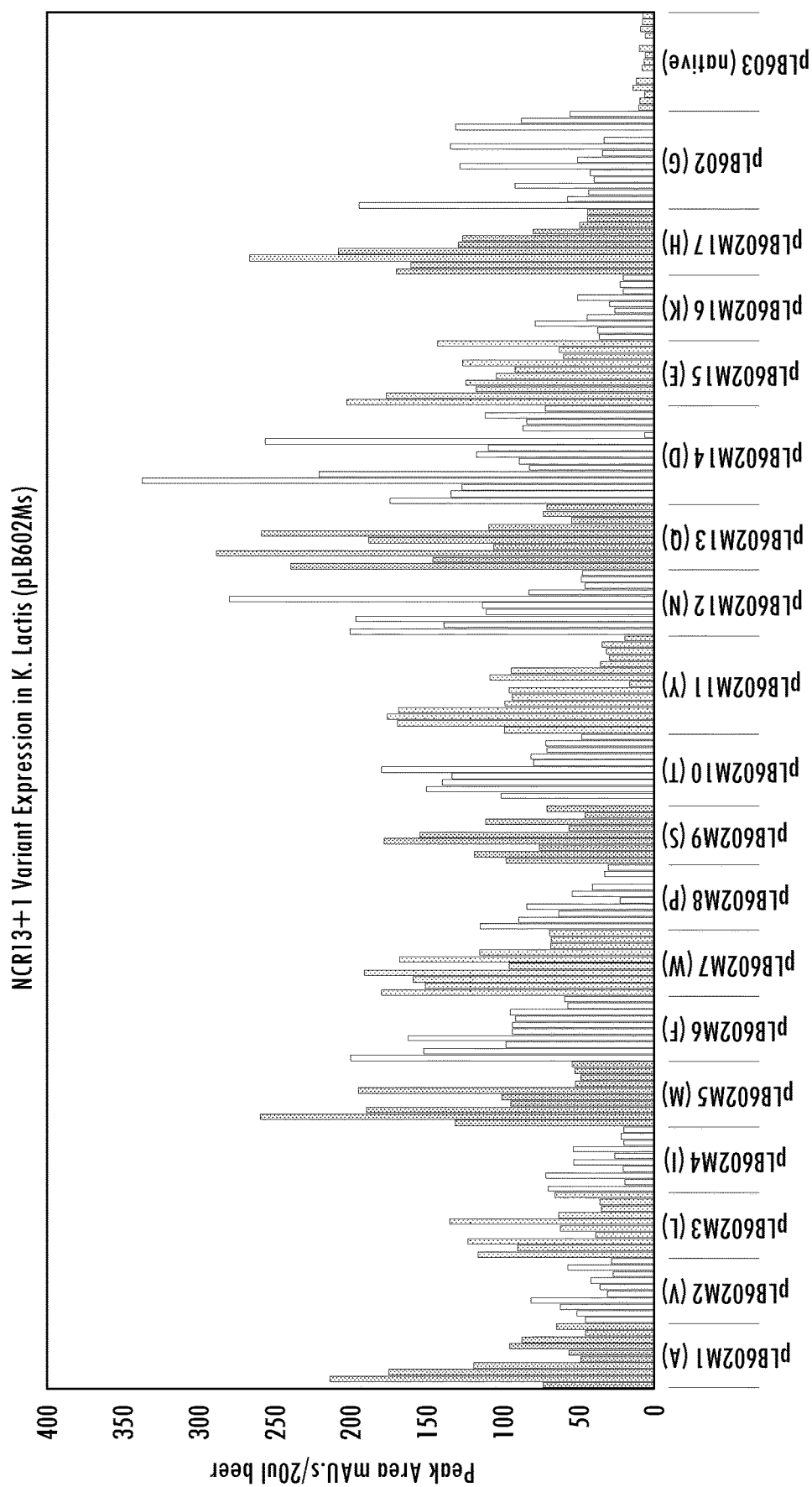
FIG. 2 shows the results of the deep-well expression assay. The vectors pLB602 (operable to encode NCR13a, SEQ ID NO: 2), pLB603 (operable to encode WT-NCR13, SEQ ID NO: 1), and pLB602M1-M17 (encoding the NCR13M1 having SEQ ID NO: 3, and NVPs having SEQ ID NOs: 4-19), were then linearized, and transformed into electrocompetent Kluyveromyces lactis host cells, and the expression of the peptides were analyzed. The vector names are shown below, with the N-terminus addition for a given NVP shown in parenthesis.
Figure 3:
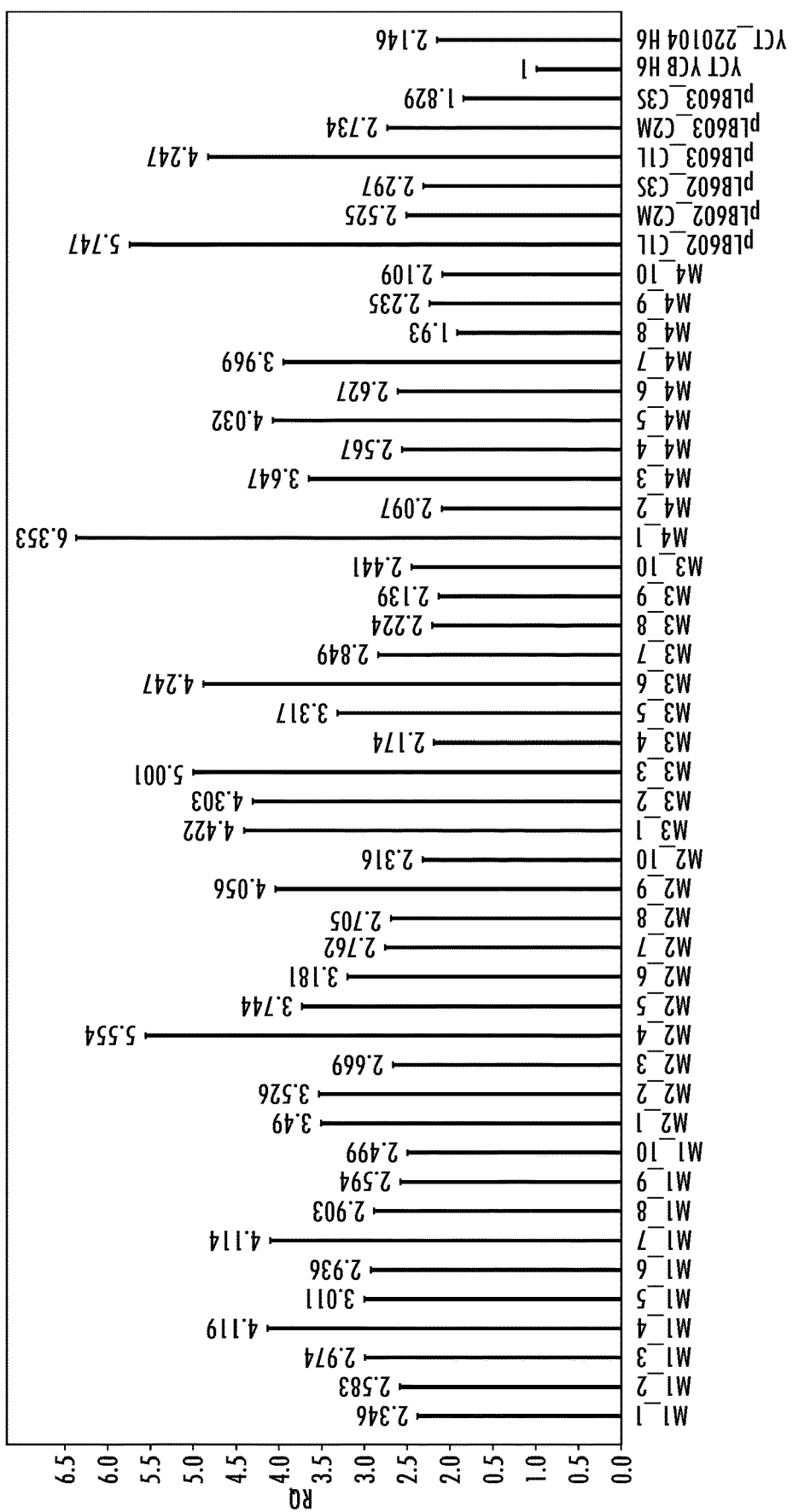
FIG. 3 shows the results of a qPCR assay evaluating yield-per-copy number. Here, the relationship between copy number and yield was evaluated in recombinant yeast cell strains transformed with the following vectors: pLB602 (operable to encode NCR13a, SEQ ID NO: 2), pLB603 (operable to encode WT-NCR13, SEQ ID NO: 1), and pLB602M1-M4 (encoding SEQ ID NOs: 3-6) (N=10). The Y-axis shows relative quantification ("RQ"). The numbers above each bar shows the number of integrated gene copies. YCT YCT H12 and YCT_220104 are untransformed control strains. URA3 was used as the endogenous control gene. Error bars show minimum and maximum number of copies.
Figure 4:
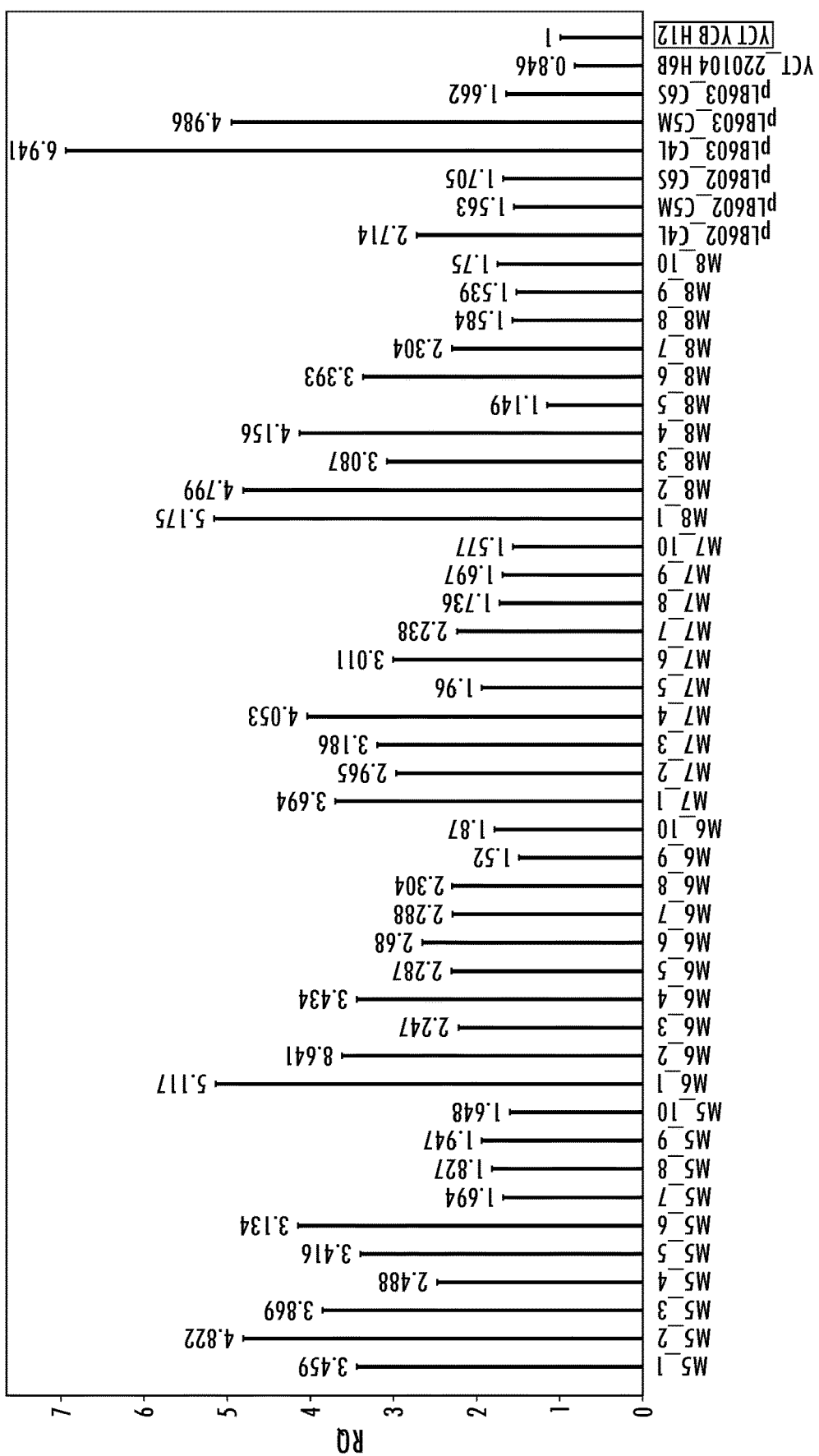
FIG. 4 shows the results of a qPCR assay evaluating yield-per-copy number. Here, the relationship between copy number and yield was evaluated in recombinant yeast cell strains transformed with the following vectors: pLB602 (operable to encode NCR13a, SEQ ID NO: 2), pLB603 (operable to encode WT-NCR13, SEQ ID NO: 1), and pLB602M5-M8 (encoding the NVPs, SEQ ID NOs: 7-10) (N=10). The Y-axis shows relative quantification ("RQ"). The numbers above each bar shows the number of integrated gene copies. YCT YCT H12 and YCT_220104 are untransformed control strains. YCT YCT H12 (shown in a box) was the calibration strain. URA3 was used as the endogenous control gene. Error bars show minimum and maximum number of copies.
Figure 5:
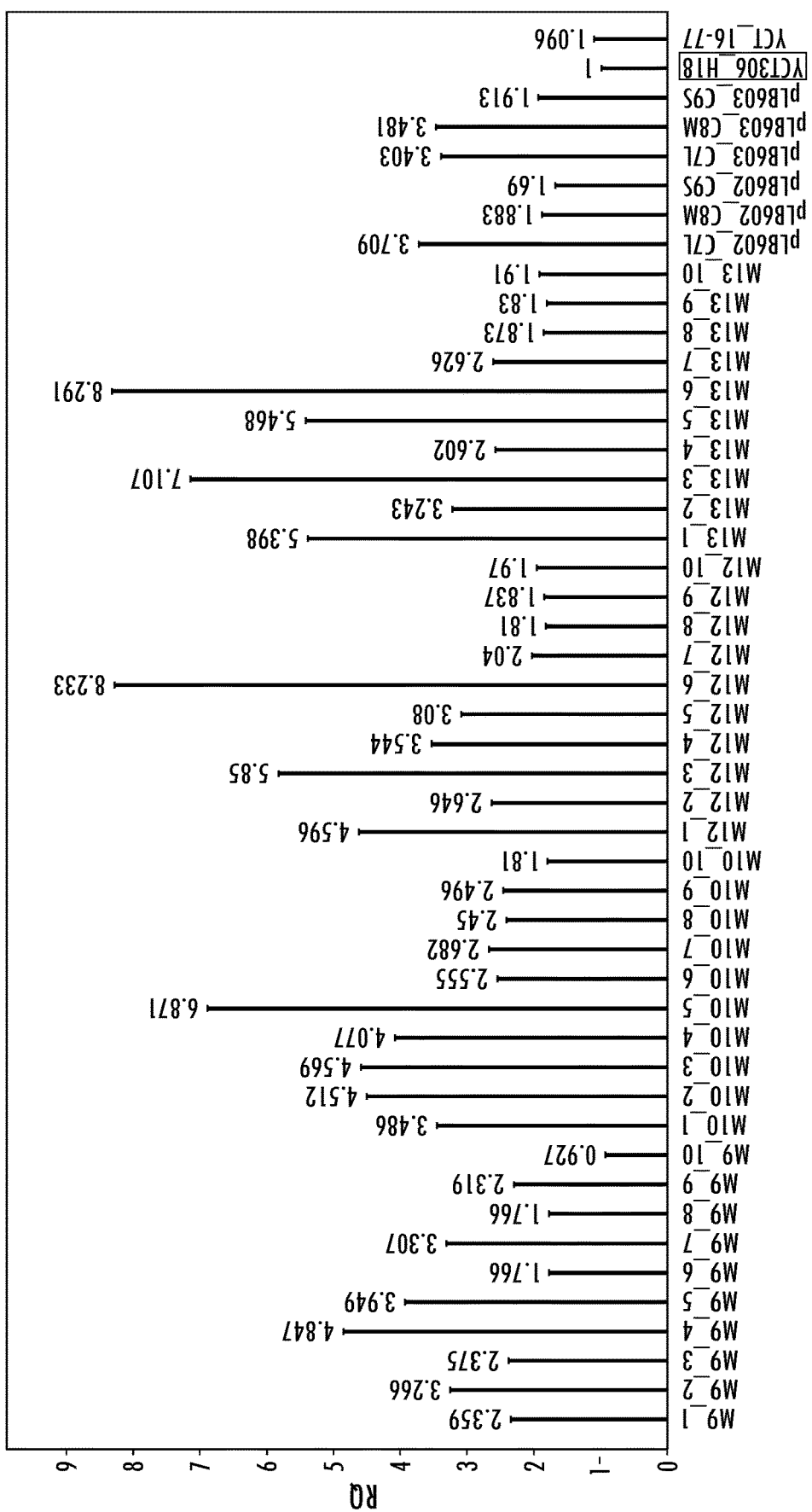
FIG. 5 shows the results of a qPCR assay evaluating yield-per-copy number. Here, the relationship between copy number and yield was evaluated in recombinant yeast cell strains transformed with the following vectors: pLB602 (operable to encode NCR13a, SEQ ID NO: 2), pLB603 (operable to encode WT-NCR13, SEQ ID NO: 1), and pLB602M9-10, and M12-M13 (encoding the NVPs, SEQ ID NOs: 11-12, and 14-15) (N=10). The Y-axis shows relative quantification ("RQ"). The numbers above each bar shows the number of integrated gene copies. YCT306 H18 and YCT_16-77 are untransformed control strains. YCT306 H18 (shown in the box) was the calibration strain. URA3 was used as the endogenous control gene. Error bars show minimum and maximum number of copies.
Figure 6:
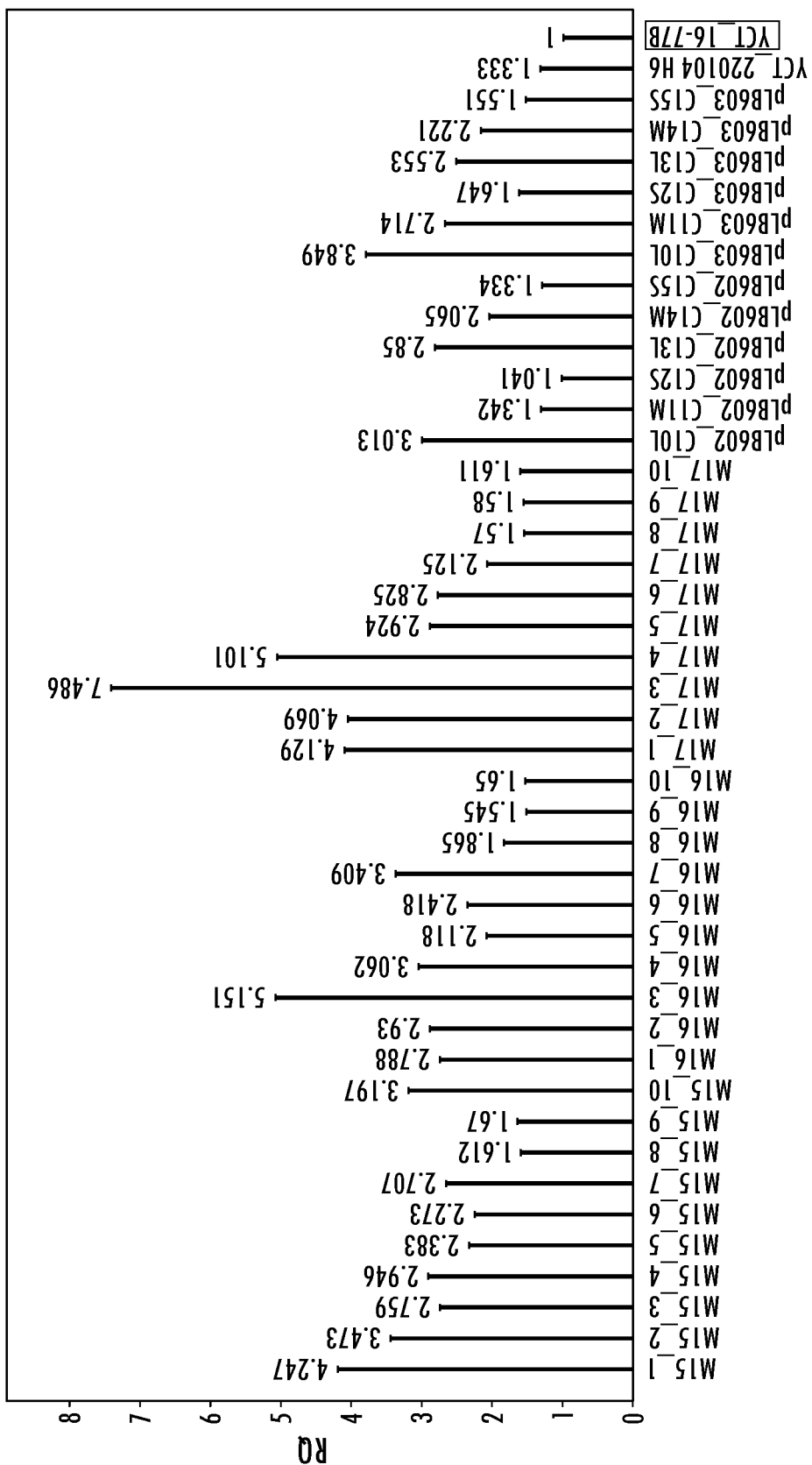
FIG. 6 shows the results of a qPCR assay evaluating yield-per-copy number. Here, the relationship between copy number and yield was evaluated in recombinant yeast cell strains transformed with the following vectors: pLB602 (operable to encode NCR13a, SEQ ID NO: 2), pLB603 (operable to encode WT-NCR13, SEQ ID NO: 1), and pLB602M15-M17 (encoding the NVPs, SEQ ID NOs: 17-19) (N=10). The Y-axis shows relative quantification ("RQ"). The numbers above each bar shows the number of integrated gene copies. YCT_220104 H6 and YCT_16-778 are untransformed control strains. YCT_16-778 (shown in the box) was the calibration strain. URA3 was used as the endogenous control gene. Error bars show minimum and maximum number of copies.
Figure 7:
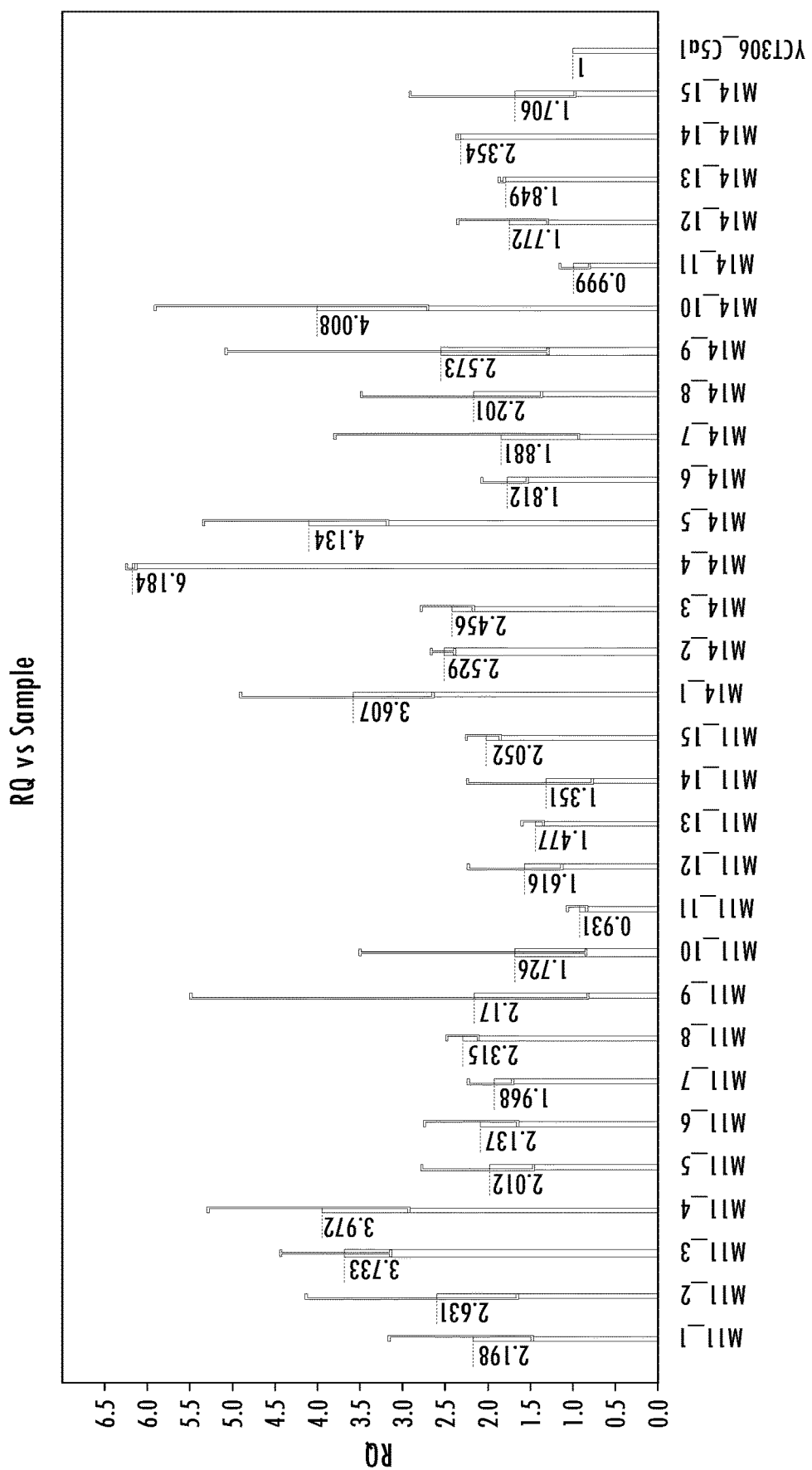
FIG. 7 shows the results of a qPCR assay evaluating yield-per-copy number. Here, the relationship between copy number and yield was evaluated in recombinant yeast cell strains transformed with the following vectors: pLB602 (operable to encode NCR13a, SEQ ID NO: 2), pLB603 (operable to encode WT-NCR13, SEQ ID NO: 1), and pLB602M11 and M14 (encoding the NVPs, SEQ ID NOs: 13 and 16) (N=10). The Y-axis shows relative quantification ("RQ"). The numbers above each bar shows the number of integrated gene copies. YCT_220104 and YCT_16-77 are untransformed control strains. URA3 was used as the endogenous control gene. Error bars show minimum and maximum number of copies.

As shown in FIG. 2, all of the NVPs had much better yield profile than the WT-NCR13, perhaps owing to the addition of a single amino acid spacer at the N-terminus, which could help the secretion of the expressed peptides via improvement of Kex2 cleavage by additional spacing from disulfide bonds.

Example 3. Yield-Per-Copy Number and Productivity

To evaluate the relationship between copy number and yield, the recombinant yeast cell strains transformed with vectors described in Example 1, i.e., pLB602 (operable to encode NCR13a, SEQ ID NO: 2), pLB603 (operable to encode WT-NCR13, SEQ ID NO: 1), and pLB602M1-M17 (encoding the SEQ ID NOs: 3-19), were picked for gDNA extraction and yield-per-copy number relation study.

The gDNA from 10 replicates of each of the recombinant yeast strains (N=10) was extracted using Chelex 100 glass beads. The qPCR reactions were set up for all gDNAs extracted from the recombinant yeast strains to identify the number of integrated target gene copies (i.e., WT-NCR13, NCR13a, or NVPs) contained in the recombinant yeast strain genomes, using Luna universal qPCR master mix reagent (New England Biolabs) and QuanStudio 3 Real-time PCR system (Thermo-Fisher). Here, qPCR primers for URA3 were used as an endogenous control (SEQ ID NOs: 60-62), and the LAC4 promoter (pLAC4) was used as the target integrated gene region to determine the integration copy number (SEQ ID NOs: 63-65). Various non-transformed yeast strains were used as the control yeast strain. FIGS. 3-7.

Figure 8:
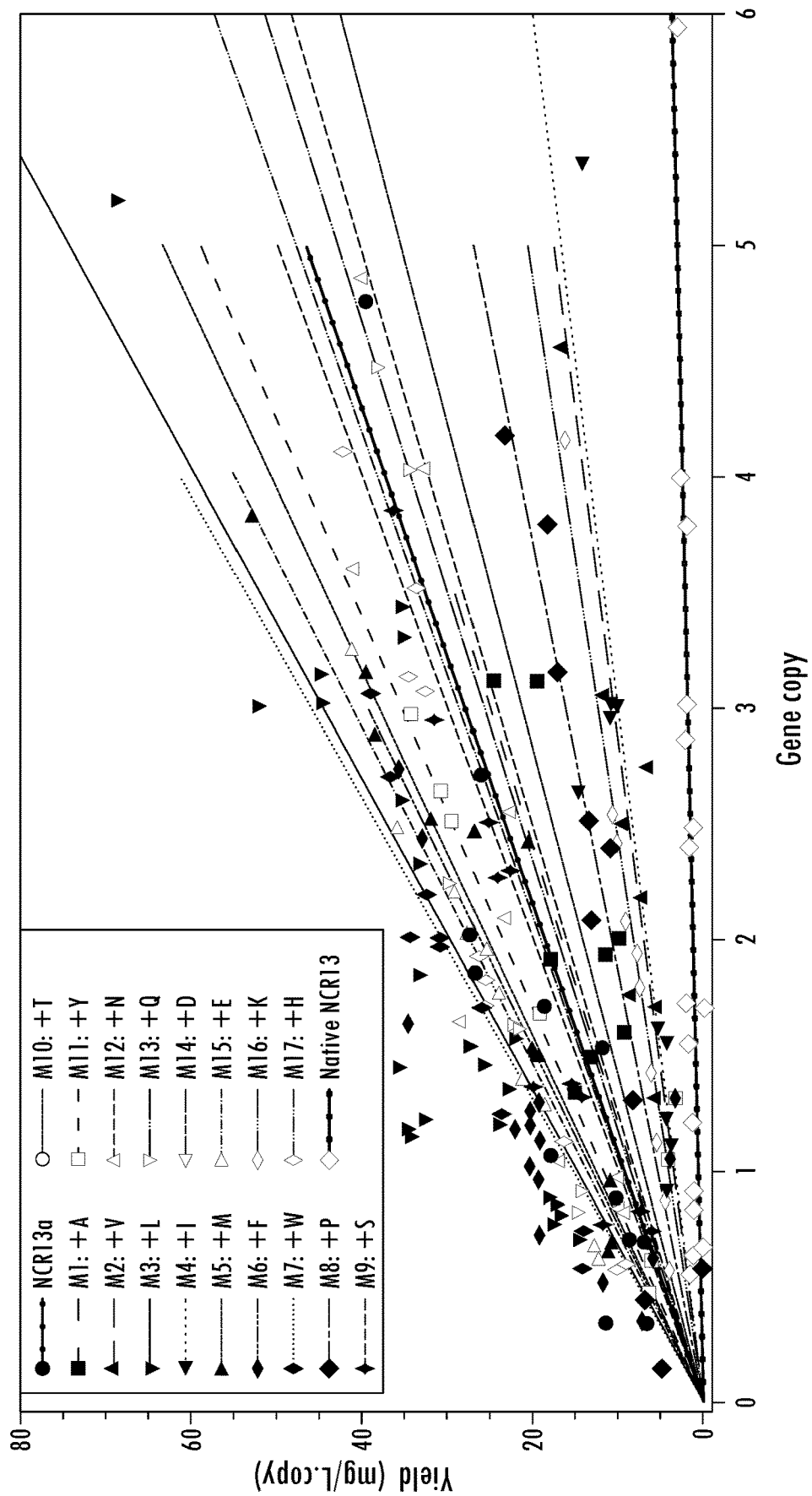
FIG. 8 shows a graph depicting the liner relationship between peptide yield and numbers of integrated gene copies. The slope of lines is defined as gene productivity, which indicates the yield of a given peptide per integrated gene copy.
Figure 9:
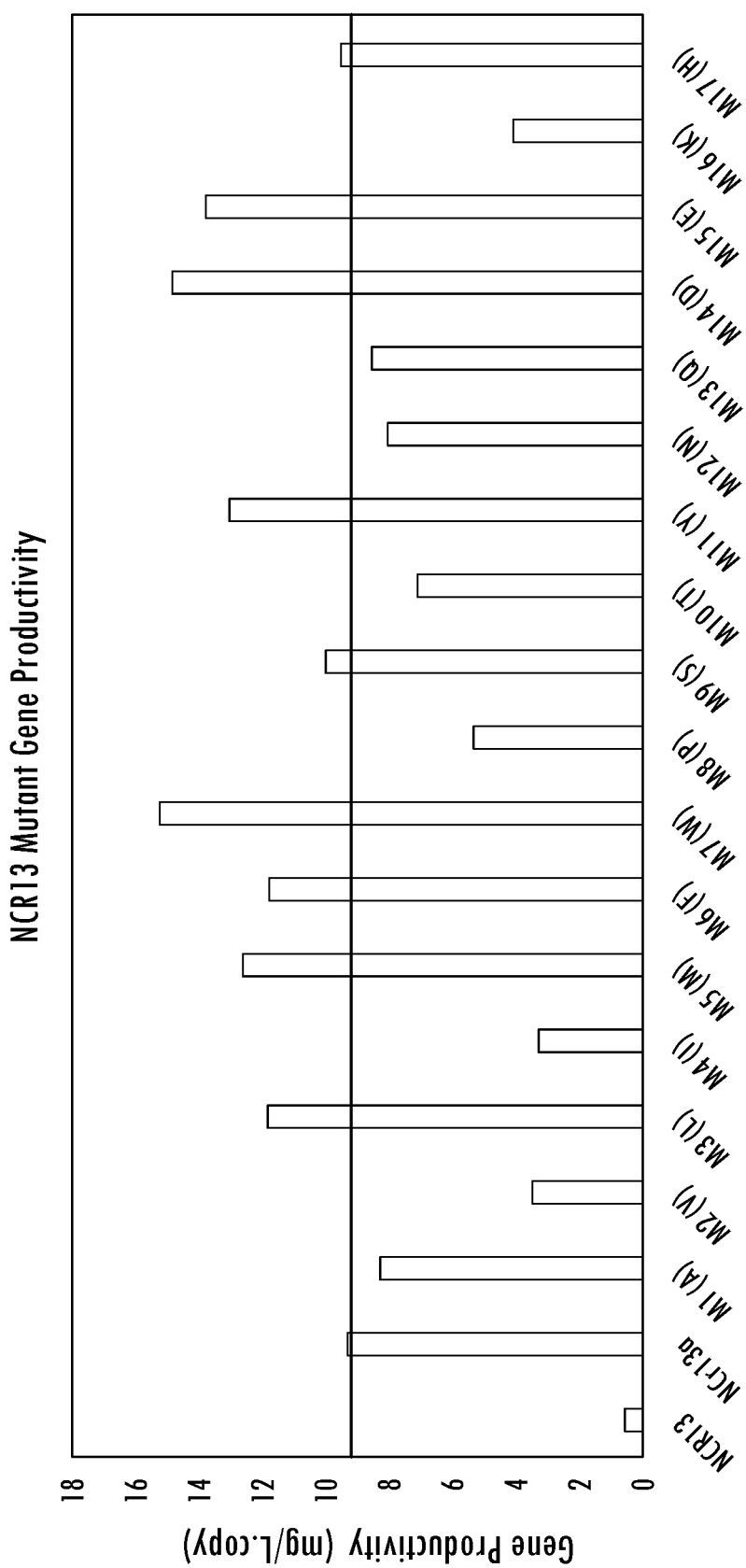

The deep-well culture peptide yields of the recombinant yeast strains determined in Example 2, were plotted against the corresponding qPCR results described above showing the number of integrated-target-gene copies. As shown in FIG. 8, the slopes of the plots indicate peptide yield from a recombinant yeast strain per integrated target gene copy, in the strain genome (gene productivity). As shown in FIG. 9, all of the NVPs showed much higher yield and gene productivity than the WT-NCR13; however, the following peptides showed higher gene productivity relative to NCR13a, and were therefore selected for further evaluation: NVPM1 (+A) (SEQ ID NO: 3); NVPM3 (+L) (SEQ ID NO: 5); NVPM5 (+M) (SEQ ID NO: 7); NVPM6 (+F) (SEQ ID NO: 8); NVPM7 (+W) (SEQ ID NO: 9); NVPM9 (+S) (SEQ ID NO: 11); NVPM11 (+Y) (SEQ ID NO: 13); NVPM14 (+D) (SEQ ID NO: 16); and NVPM15 (+E) (SEQ ID NO: 17).

The peptide yields of the foregoing peptides were purified by cation exchange chromatography using Nuvia HR-S resin (Bio-Rad Laboratories). Briefly, supernatant was bound to resin and eluted with increasing concentrations of sodium chloride. Elutions were dialyzed, lyophilized, and resuspended in water, and concentration (mg/mL) was determined. A summary of the peptide yields are shown in the table below.

TABLE 3

Ion exchange purification summary. With the exception of NVPM1 (SEQ ID NO: 3), all of the peptides shown here had a yield improvement relative to NCR13a.

| SEQ ID NO | Name | M | Conc. (mg/mL) | Total Vol. (mL) |
|---|---|---|---|---|
| 3 | NVPM1 | +A | 5.42 | 1.3348 |
| 5 | NVPM3 | +L | 5.09 | 0.4699 |
| 7 | NVPM5 | +M | 4.29 | 1.1815 |
| 8 | NVPM6 | +F | 6.91 | 0.6564 |
| 9 | NVPM7 | +W | 6.61 | 0.9445 |
| 11 | NVPM9 | +S | 6.8 | 1.0912 |
| 13 | NVPM11 | +Y | 5.3 | 0.8483 |
| 16 | NVPM14 | +D | 11.2 | 0.6638 |
| 17 | NVPM15 | +E | 10.5 | 0.6648 |

Example 4. Antimicrobial Bioassay (*Botrytis cinerea*)

The antimicrobial effect of the NCR13 variant peptides (NVPs) of the present disclosure were evaluated against the fungal species, *Botrytis cinerea*. Briefly, NVPs showing superior yield relative to NCR13a (i.e., NVPs having an amino acid sequence as set forth in SEQ ID NOs: 5, 7, 8, 9, 11, 13, 16, and 17), were incubated at varying concentrations with *Botrytis cinerea*. The growth of *Botrytis cinerea* was then assessed via OD600 nm after incubation with a given NVP at room temperature after 96 hours.

The NVPs assessed were as follows: NVPM3 (+L) (SEQ ID NO: 5); NVPM5 (+M) (SEQ ID NO: 7); NVPM6 (+F) (SEQ ID NO: 8); NVPM7 (+W) (SEQ ID NO: 9); NVPM9 (+S) (SEQ ID NO: 11); NVPM11 (+Y) (SEQ ID NO: 13); NVPM14 (+D) (SEQ ID NO: 16); and NVPM15 (+E) (SEQ ID NO: 17).

NVPs having an amino acid sequence of SEQ ID NOs: 5, 7, 8, 9, 11, 13, 16, and 17 were generated as described above in Example 1. The peptide, NCR13a, having an amino acid sequence of: GTKPCQSDKDCKKFACRKPKVPKC-INGFCKCVR (SEQ ID NO: 2) was selected as a comparator peptide, with which the antifungal activity of the foregoing NVPs was compared.

The fungal species was *Botrytis cinerea* was cultured in potato dextrose agar plates. Fungal spores were collected from the agar plates and suspended into de-ionized water, followed by enumeration in a Petroff-Hausser counting chamber (VWR). The enumerated spores were then inoculated into 100 μL synthetic fungal medium (SFM) ($K_2HPO_4$ 2.5 mM, $MgSO_4$ 50 μM, $CaCl_2$) 50 μM, $FeSO_4$ 5 μM, $CoCl_2$ 0.1 μM, $CuSO_4$ 0.1 μM, $Na_2MoO_4$ 2 μM, $H_3BO_3$ 0.5 μM, KI 0.1 μM, $ZnSO_4$ 0.5 μM, $MnSO_4$ 0.1 μM, glucose 10 g/L, asparagine 1 g/L, methionine 20 mg/L, myo-inositol 2 mg/L, biotin 0.2 mg/L, thiamine-HCl 1 mg/L, and pyridoxine-HCl 0.2 mg/L) in sterile Corning 96-well tissue culture plates—each of which contained a 2-fold serial dilution of either a purified NVP, or NCR13a peptide, to achieve the final desired cell density of approximately $2.5 \times 10^4$ CFU/mL.

The 96-well plates were incubated at room temperature for 96 hours without shaking. The OD600 of the culture plate was determined using SpectraMax plate reader. Relative OD600 was determined by normalizing cell growth to control wells containing neither NVPs nor NCR13a. The OD600 was used to determine $IC_{50}$.

Results

Figure 10:
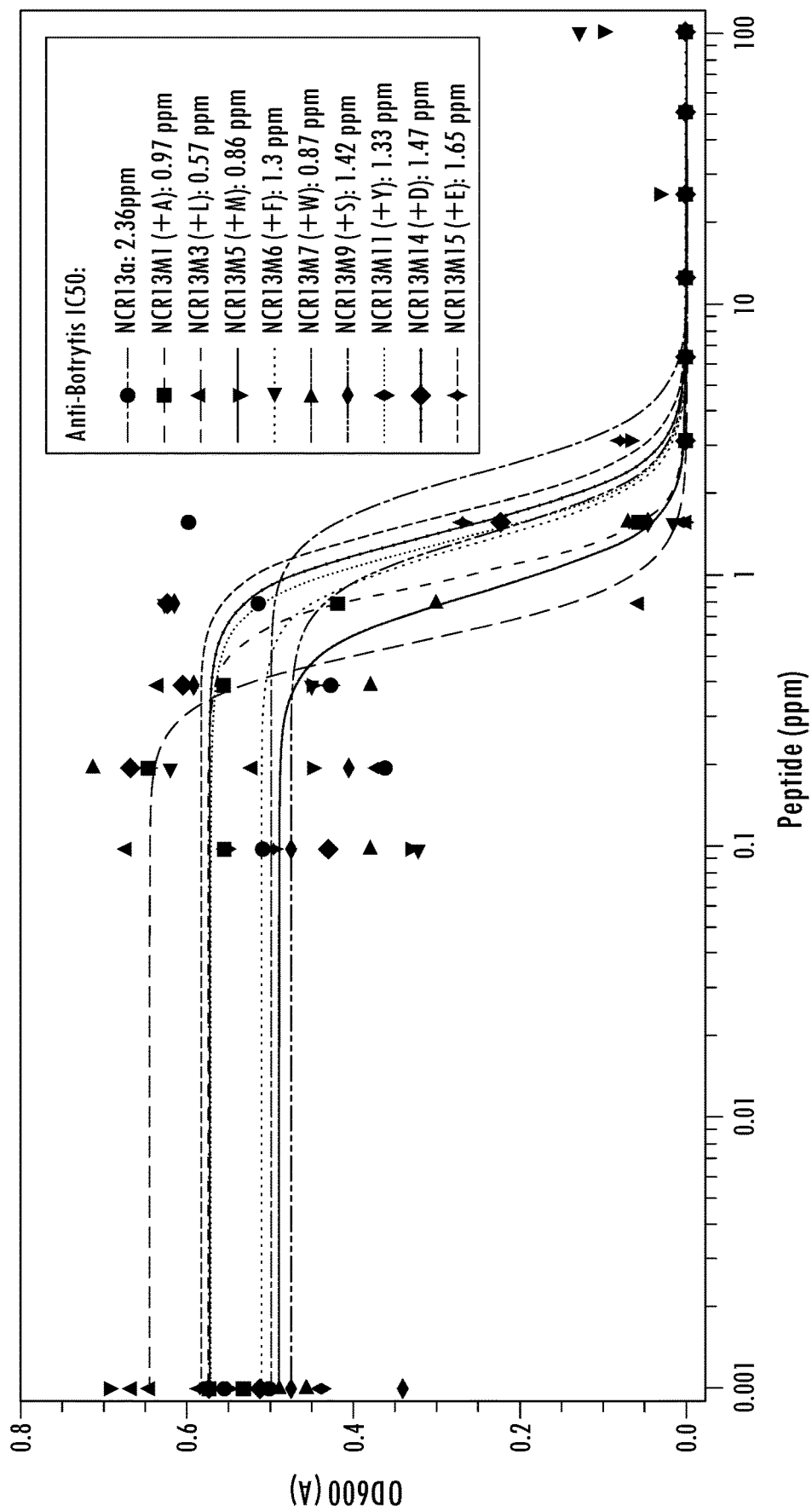
FIG. 10 shows the results of the antimicrobial bioassay. The antimicrobial effect of the NCR13 variant peptides (NVPs) of the present disclosure were evaluated against the fungal species, *Botrytis cinerea*. Briefly, NVPs showing superior yield relative to NCR13a (i.e., NVPs having an amino acid sequence as set forth in SEQ ID NOs: 5, 7, 8, 9, 11, 13, 16, and 17), were incubated at varying concentrations with *Botrytis cinerea*. The growth of *Botrytis cinerea* was then assessed via OD600 nm after incubation with a given NVP at room temperature after 96 hours. The $IC_{50}$ of each peptide analyzed is shown in ppm.

NCR13a inhibition of *Botrytis* growth was observed with $IC_{50}$ at 2.36 ppm. FIG. 10. However, as shown in FIG. 10 and the table below, the NVPs evaluated were shown to have improved anti-*Botrytis* activities relative to NCR13a.

TABLE 4

Antimicrobial effect of NCR13a and NVPs against *Botrytis cinerea*. Here, the amount shown below is the amount required to achieve $IC_{50}$ in *Botrytis cinerea* cells.

| SEQ ID NO | Name | Addition | $IC_{50}$ (ppm) |
| --- | --- | --- | --- |
| 1 | NCR13a | — | 2.36 |
| 3 | NVPM1 | +A | 0.97 |
| 5 | NVPM3 | +L | 0.57 |
| 7 | NVPM5 | +M | 0.86 |
| 8 | NVPM6 | +F | 1.3 |
| 9 | NVPM7 | +W | 0.87 |
| 11 | NVPM9 | +S | 1.42 |
| 13 | NVPM11 | +Y | 1.33 |
| 16 | NVPM14 | +D | 1.47 |
| 17 | NVPM15 | +E | 1.65 |

Example 5. Summary of Yield and Activity Improvements

Figure 11:
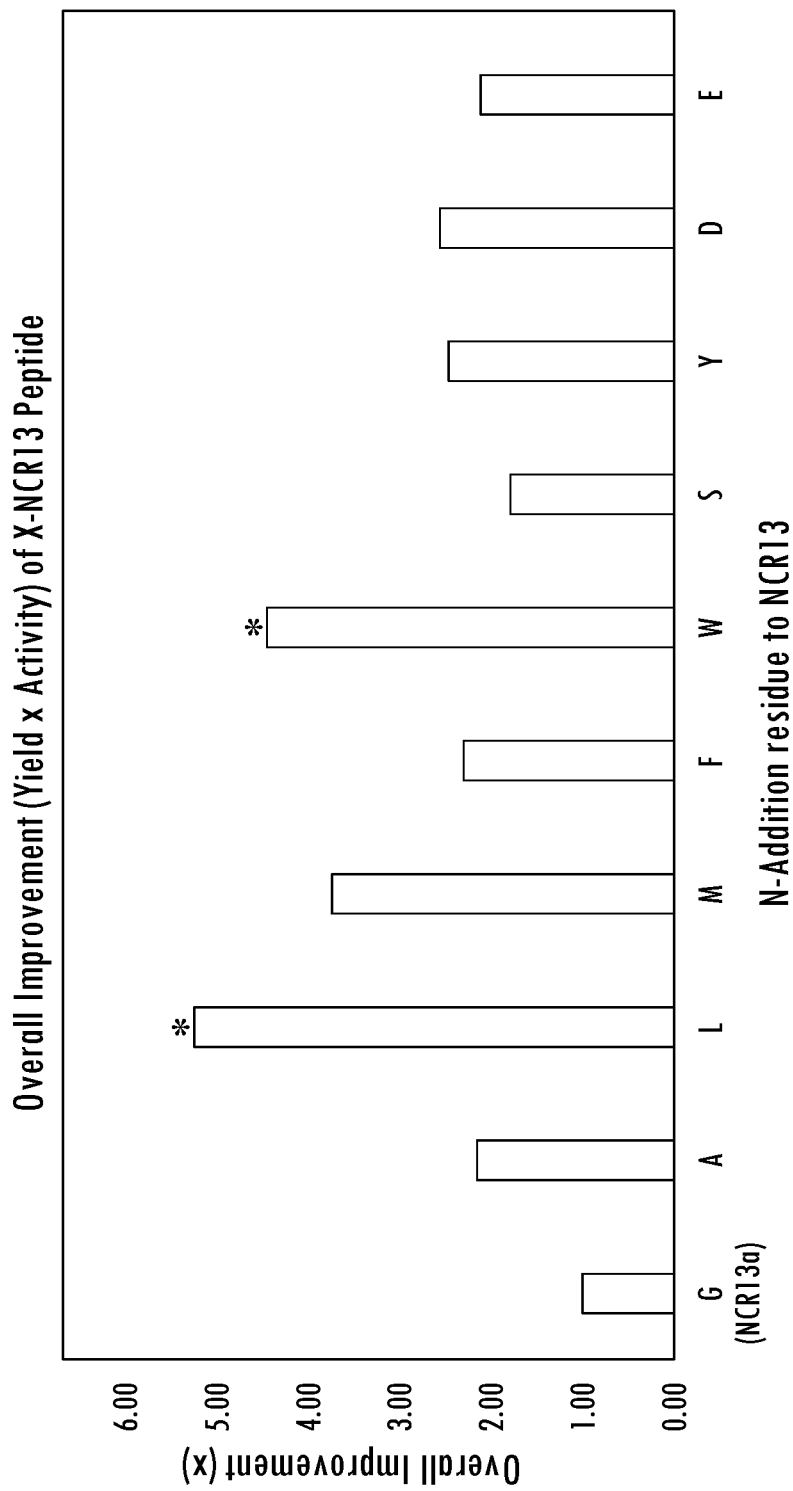
FIG. 11 shows a graph depicting the overall improvement of a given NVP as determined by yield improvement times the activity improvement. The N-terminus amino acid addition of each NVP is shown on the X-axis. Asterisks show the NVP with the greatest improvement.

A summary of the NVPs having improved yield and/or activity is shown in the table below, and summarized in FIG. 11.

TABLE 5

Summary of yield and activity improvements. COG = "Cost of goods," which is yield improvement times the activity improvement.

| Name | +1 Mutation | Yield ratio to NCR13a | Activity ratio to NCR13a | COG Improvement | SEQ ID NO |
| --- | --- | --- | --- | --- | --- |
| NCR13a | Q | 1 | 1 | 1 | 1 |
| NVPM1 | A | 0.89 | 2.43 | 2.16 | 3 |
| NVPM3 | L | 1.27 | 4.14 | 5.27 | 5 |
| NVPM5 | M | 1.36 | 2.74 | 3.73 | 7 |
| NVPM6 | F | 1.27 | 1.82 | 2.3 | 8 |
| NVPM7 | W | 1.64 | 2.71 | 4.46 | 9 |
| NVPM9 | S | 1.07 | 1.66 | 1.78 | 11 |
| NVPM11 | Y | 1.41 | 1.77 | 2.5 | 13 |
| NVPM14 | D | 1.6 | 1.61 | 2.57 | 16 |
| NVPM15 | E | 1.48 | 1.43 | 2.11 | 17 |

All of the NVPs having an amino acid sequence as set forth in SEQ ID NOs: 5, 7, 8, 9, 11, 13, 16, and 17 showed improved anti-*Botrytis* activities relative to NCR13a. Combining the yield improvement and activity improvement, the two NVPs that produced the most overall improvement were NVPM3 (+L) (SEQ ID NO: 5) which had a 5.3-fold overall improvement, and NVPM7 (+W) (SEQ ID NO: 9), which had a 4.5-fold overall improvement. FIG. 11.

The invention claimed is:

1. An antimicrobial NCR13 variant peptide (NVP) having antimicrobial activity against one or more microbes, said NVP consisting of an amino acid sequence as set forth in Formula (I): $X_1$-T-K-P-C-Q-S-D-K-D-C-K-K-F-A-C-R-K-P-K-V-P-K-C-I-N-G-F-C-K-C-V-R, wherein $X_1$ represents the amino acid added to the N-terminus of SEQ ID NO: 1, wherein $X_1$ is the amino acid: V, L, I, M, F, W, P, S, T, Y, N, Q, D, E, K, R, or H or an agriculturally acceptable salt thereof.

2. The NVP of claim 1, wherein $X_1$ is the amino acid: L, M, F, W, S, Y, D, or E.

3. A composition comprising an antimicrobial NCR13 variant peptide (NVP) according to claim 1 and an excipient.

4. A method of combating, controlling, or inhibiting a microbe comprising applying a antimicrobially effective amount of: (1) an antimicrobial NCR13 variant peptide (NVP), or an agriculturally acceptable salt thereof according to claim 1, or (2) a composition comprising the NVP according to claim 1, and an excipient; to the microbe, a locus of the microbe, a food supply of the microbe, a habitat of the microbe, or a breeding ground of the microbe; a plant, a seed, a plant part, a locus of a plant, or an environment of a plant that is susceptible to an attack by the microbe; an animal, a locus of an animal, or an environment of an animal susceptible to an attack by the microbe; or a combination thereof.

5. The method of claim 4, wherein $X_1$ is the amino acid: L, M, F, W, S, Y, D, or E.

6. The method of claim 4, wherein the microbe is a pathogenic fungus.

7. The method of claim 6, wherein the pathogenic fungus is a plant-specific pathogenic fungus, or a phytopathogenic fungus.

8. The method of claim 7, wherein the phytopathogenic fungus is a phytopathogenic fungus belonging to the genera: *Monilinia, Botrytis, Fusarium, Venturia, Wilsonomyces, Botryosphaeria, Penicillium, Rhizopus, Aspergillus, Podosphaera, Erysiphe, Golovinomyces, Leveillula, Peronospora, Pseudoperonospora, Plasmopara, Bremia, Cladosporium, Neofabraea, Microdochium, Marssonina, Sclerotinia, Rhizopus, Didymella, Alternaria, Verticillium, Phytophthora, Colletotrichum, Cercospora, Phakopsora, Rhizoctonia, Sclerotinia, Pythium, Phoma, Gaeumannomces, Leptoshaeria,* or *Puccinia*.

9. The method of claim 8, wherein the microbe is a microbe belonging to the genera: *Monilinia* or *Botrytis*.

10. The method of claim 9, wherein the microbe is a *Monilinia fructicola* or a *Botrytis cinerea*.

* * * * *